(12) United States Patent
Nemet et al.

(10) Patent No.: US 10,037,507 B2
(45) Date of Patent: Jul. 31, 2018

(54) SYSTEM AND METHOD FOR IMPROVED QUALITY MANAGEMENT IN A PRODUCT LOGISTIC CHAIN

(71) Applicant: Varcode Ltd., Rosh Haain (IL)

(72) Inventors: Yaron Nemet, Kedumim (IL); Ephraim Brand, Givataim (IL)

(73) Assignee: Varcode Ltd., Rosh Ha'ayin (IL)

( * ) Notice: Subject to any disclaimer, the term of this patent is extended or adjusted under 35 U.S.C. 154(b) by 0 days.

(21) Appl. No.: 15/488,943

(22) Filed: Apr. 17, 2017

(65) Prior Publication Data

US 2017/0262782 A1 Sep. 14, 2017

Related U.S. Application Data

(63) Continuation of application No. 15/137,316, filed on Apr. 25, 2016, now Pat. No. 9,646,277, which is a
(Continued)

(51) Int. Cl.
| | |
|---|---|
| *G06K 7/10* | (2006.01) |
| *G06K 19/06* | (2006.01) |
| *G06Q 10/06* | (2012.01) |
| *G06K 7/14* | (2006.01) |
| *G01N 33/84* | (2006.01) |

(Continued)

(52) U.S. Cl.
CPC ....... *G06Q 10/06395* (2013.01); *G01K 13/00* (2013.01); *G01N 31/221* (2013.01); *G01N 33/02* (2013.01); *G01N 33/84* (2013.01); *G06K 7/1408* (2013.01); *G06K 19/06028* (2013.01); *G06K 19/06037* (2013.01); *G06K 19/06046* (2013.01); *G06K 19/10* (2013.01); *G06Q 10/087* (2013.01); *G06Q 30/02* (2013.01)

(58) Field of Classification Search
CPC .................................. G06K 19/06; G06K 7/14
USPC .......... 235/383, 385, 462.01, 462.07, 462.13
See application file for complete search history.

(56) References Cited

U.S. PATENT DOCUMENTS

| | | | |
|---|---|---|---|
| 4,057,029 A | 11/1977 | Seiter | |
| 4,059,407 A | 11/1977 | Hochstrasser | |

(Continued)

FOREIGN PATENT DOCUMENTS

| | | |
|---|---|---|
| CN | 1720180 | 1/2006 |
| CN | 1914621 | 2/2007 |

(Continued)

OTHER PUBLICATIONS

An Office Action dated Nov. 4, 2013, which issued during the prosecution of U.S. Appl. No. 13/323,906.
(Continued)

*Primary Examiner* — Daniel Hess
(74) *Attorney, Agent, or Firm* — Fish & Richardson P.C.

(57) ABSTRACT

A quality management system for products including a multiplicity of product unit specific indicators, each operative to provide a machine-readable indication of exceedence of at least one threshold by at least one product quality determining parameter, an indicator reader operative to read the product unit specific indicators and to provide output indications and a product type specific indication interpreter operative to receive the output indications and to provide human sensible, product unit specific, product quality status outputs.

5 Claims, 27 Drawing Sheets

Related U.S. Application Data continuation of application No. 14/595,395, filed on Jan. 13, 2015, now Pat. No. 9,349,086, which is a continuation of application No. 13/490,705, filed on Jun. 7, 2012, now Pat. No. 8,967,467, which is a continuation of application No. 12/471,798, filed on May 26, 2009, now Pat. No. 8,196,821, which is a continuation of application No. 11/852,911, filed on Sep. 10, 2007, now Pat. No. 7,562,811, which is a continuation of application No. 11/624,492, filed on Jan. 18, 2007, now abandoned.

(60) Provisional application No. 60/804,072, filed on Jun. 6, 2006, provisional application No. 60/746,646, filed on May 7, 2006.

(51) Int. Cl.
*G01N 31/22* (2006.01)
*G01K 13/00* (2006.01)
*G06Q 30/02* (2012.01)
*G06Q 10/08* (2012.01)
*G06K 19/10* (2006.01)
*G01N 33/02* (2006.01)

(56) References Cited

U.S. PATENT DOCUMENTS

| | | |
|---|---|---|
| RE31,586 E | 5/1984 | Magnussen |
| 4,674,065 A | 6/1987 | Lange et al. |
| 5,053,339 A | 10/1991 | Patel |
| 5,084,143 A | 1/1992 | Smith |
| 5,085,802 A | 2/1992 | Jalinski |
| 5,146,405 A | 9/1992 | Church et al. |
| 5,202,677 A | 4/1993 | Parker et al. |
| 5,254,473 A | 10/1993 | Patel |
| 5,369,577 A | 11/1994 | Kadashevich et al. |
| 5,451,932 A | 9/1995 | Wunderlich et al. |
| 5,485,372 A | 1/1996 | Golding et al. |
| 5,499,597 A | 3/1996 | Kronberg |
| 5,591,952 A | 1/1997 | Krichever |
| 5,600,119 A | 2/1997 | Dvorkis |
| 5,617,488 A | 4/1997 | Hong et al. |
| 5,634,195 A | 5/1997 | Sawyer |
| 5,659,771 A | 8/1997 | Golding |
| 5,752,227 A | 5/1998 | Lyberg |
| 5,805,245 A | 9/1998 | Davis |
| 5,822,728 A | 10/1998 | Applebaum et al. |
| 5,828,991 A | 10/1998 | Skiena et al. |
| 5,841,285 A | 11/1998 | Bailey |
| 5,882,116 A | 3/1999 | Backus |
| 5,895,075 A | 4/1999 | Edwards |
| 5,899,973 A | 5/1999 | Bandara et al. |
| 5,902,982 A | 5/1999 | Lappe |
| 5,907,839 A | 5/1999 | Roth |
| 5,936,508 A | 8/1999 | Parker |
| 5,956,739 A | 9/1999 | Golding et al. |
| 6,006,221 A | 12/1999 | Liddy et al. |
| 6,009,400 A | 12/1999 | Blackman |
| 6,036,092 A | 3/2000 | Lappe |
| 6,085,206 A | 7/2000 | Domini et al. |
| 6,098,034 A | 8/2000 | Razin et al. |
| 6,154,722 A | 11/2000 | Bellegarda |
| 6,173,261 B1 | 1/2001 | Arai et al. |
| 6,190,610 B1 | 2/2001 | Goldsmith et al. |
| 6,214,623 B1 | 4/2001 | Simons et al. |
| 6,272,242 B1 | 8/2001 | Saitoh et al. |
| 6,314,400 B1 | 11/2001 | Klakow |
| 6,335,922 B1 | 1/2002 | Tiedemann et al. |
| 6,366,759 B1 | 4/2002 | Burstein et al. |
| 6,424,983 B1 | 7/2002 | Schabes et al. |
| 6,456,972 B1 | 9/2002 | Gladstein et al. |
| 6,479,016 B1 | 11/2002 | Goldsmith |
| 6,495,368 B1 | 12/2002 | Wallach |
| 6,544,925 B1 | 4/2003 | Prusik et al. |
| 6,685,094 B2 | 2/2004 | Cameron |
| 6,751,584 B2 | 6/2004 | Bangalore |
| 6,758,397 B2 | 7/2004 | Catan |
| 6,920,420 B2 | 7/2005 | Lin |
| 6,982,640 B2 | 1/2006 | Lindsay |
| 7,017,806 B2 | 3/2006 | Peterson |
| 7,020,338 B1 | 3/2006 | Cumbee |
| 7,030,863 B2 | 4/2006 | Longe et al. |
| 7,053,777 B2 | 5/2006 | Allen |
| 7,054,293 B2 | 5/2006 | Tiedemann et al. |
| 7,057,495 B2 | 6/2006 | Debord |
| RE39,226 E | 8/2006 | Lappe |
| 7,092,567 B2 | 8/2006 | Ma et al. |
| RE39,266 E | 9/2006 | Lohray et al. |
| 7,117,144 B2 | 10/2006 | Goodman et al. |
| 7,156,597 B2 * | 1/2007 | Goldsmith ............ G01N 33/02 116/206 |
| 7,157,048 B2 | 1/2007 | Goldsmith et al. |
| 7,165,019 B1 | 1/2007 | Lee et al. |
| 7,166,345 B2 | 1/2007 | Myers |
| 7,184,950 B2 | 2/2007 | Weise |
| 7,224,346 B2 | 5/2007 | Sheng |
| 7,262,792 B2 | 8/2007 | Shniberg |
| 7,277,088 B2 | 10/2007 | Robinson et al. |
| 7,295,965 B2 | 11/2007 | Haigh et al. |
| 7,295,968 B2 | 11/2007 | Bietrix et al. |
| 7,296,019 B1 | 11/2007 | Chandrasekar et al. |
| 7,340,388 B2 | 3/2008 | Soricut |
| 7,386,442 B2 | 6/2008 | Dehlinger et al. |
| 7,457,808 B2 | 11/2008 | Gaussier |
| 7,475,015 B2 | 1/2009 | Epstein et al. |
| 7,558,725 B2 | 7/2009 | Greenwald et al. |
| 7,562,811 B2 | 7/2009 | Nemet et al. |
| 7,584,093 B2 | 9/2009 | Potter et al. |
| 7,587,217 B1 | 9/2009 | Laakso et al. |
| 7,590,626 B2 | 9/2009 | Li et al. |
| 7,702,680 B2 | 4/2010 | Yih et al. |
| 7,747,427 B2 | 6/2010 | Lee et al. |
| 7,813,916 B2 | 10/2010 | Bean |
| 7,917,355 B2 | 3/2011 | Wu et al. |
| 8,005,664 B2 | 8/2011 | Hanumanthappa |
| 8,091,776 B2 | 1/2012 | Nemet |
| 8,196,821 B2 | 6/2012 | Nemet |
| 8,271,266 B2 | 9/2012 | Gallagher et al. |
| 8,321,786 B2 | 11/2012 | Lunati |
| 8,341,520 B2 | 12/2012 | Iakobashvili et al. |
| 8,365,070 B2 | 1/2013 | Song et al. |
| 8,473,278 B2 | 6/2013 | Futagi et al. |
| 8,500,014 B2 | 8/2013 | Nemet et al. |
| 8,528,808 B2 | 9/2013 | Nemet |
| 8,540,156 B2 | 9/2013 | Nemet |
| 8,579,193 B2 | 11/2013 | Nemet |
| 8,626,786 B2 | 1/2014 | Halcrow et al. |
| 8,807,422 B2 | 8/2014 | Nemet |
| 8,950,664 B2 | 2/2015 | Nemet et al. |
| 8,960,534 B2 | 2/2015 | Nemet et al. |
| 8,967,467 B2 | 3/2015 | Nemet et al. |
| 9,122,963 B2 | 9/2015 | Nemet |
| 9,135,544 B2 | 9/2015 | Nemet et al. |
| 9,317,794 B2 | 4/2016 | Nemet et al. |
| 9,349,086 B2 | 5/2016 | Nemet et al. |
| 9,373,100 B2 | 6/2016 | Nemet et al. |
| 9,384,435 B2 | 7/2016 | Nemet et al. |
| 9,396,423 B2 | 7/2016 | Nemet et al. |
| 9,400,952 B2 | 7/2016 | Nemet |
| 9,558,439 B2 | 1/2017 | Nemet et al. |
| 9,626,610 B2 | 4/2017 | Nemet et al. |
| 9,633,296 B2 | 4/2017 | Nemet |
| 9,646,237 B2 | 5/2017 | Nemet et al. |
| 9,646,277 B2 | 5/2017 | Nemet et al. |
| 9,710,743 B2 | 7/2017 | Nemet et al. |
| 2002/0012332 A1 | 1/2002 | Tiedemann et al. |
| 2002/0032564 A1 | 3/2002 | Eshani et al. |
| 2002/0056756 A1 | 5/2002 | Cameron et al. |
| 2002/0128821 A1 | 9/2002 | Ehsani |

(56) References Cited

U.S. PATENT DOCUMENTS

| | | |
|---|---|---|
| 2002/0169595 A1 | 11/2002 | Agichtein et al. |
| 2003/0187632 A1 | 10/2003 | Menich |
| 2003/0204569 A1 | 10/2003 | Andrews et al. |
| 2003/0210249 A1 | 11/2003 | Simske |
| 2003/0227392 A1 | 12/2003 | Ebert |
| 2003/0233222 A1 | 12/2003 | Soricut et al. |
| 2004/0002849 A1 | 1/2004 | Zhou |
| 2004/0018641 A1 | 1/2004 | Goldsmith et al. |
| 2004/0030540 A1 | 2/2004 | Ovil et al. |
| 2004/0093567 A1 | 5/2004 | Schabes et al. |
| 2004/0138869 A1 | 7/2004 | Heinecke |
| 2004/0215514 A1 | 10/2004 | Devlin |
| 2004/0260543 A1 | 12/2004 | Horowitz |
| 2005/0043940 A1 | 2/2005 | Elder |
| 2005/0044495 A1 | 2/2005 | Lee et al. |
| 2005/0053900 A1 | 3/2005 | Kaufmann |
| 2005/0083413 A1 | 4/2005 | Reed et al. |
| 2005/0091030 A1 | 4/2005 | Jessee et al. |
| 2005/0091088 A1 | 4/2005 | Peterson |
| 2005/0108001 A1 | 5/2005 | Aarskog |
| 2005/0120002 A1 | 6/2005 | Behbehani |
| 2005/0139686 A1 | 6/2005 | Helmer et al. |
| 2005/0143971 A1 | 6/2005 | Burstein |
| 2005/0162274 A1 | 7/2005 | Shniberg et al. |
| 2005/0209844 A1 | 9/2005 | Wu et al. |
| 2005/0257146 A1 | 11/2005 | Ashcraft et al. |
| 2006/0003297 A1 | 1/2006 | Wiig et al. |
| 2006/0032427 A1 | 2/2006 | Ishii et al. |
| 2006/0048055 A1 | 3/2006 | Wu et al. |
| 2006/0057022 A1 | 3/2006 | Williams |
| 2006/0074655 A1 | 4/2006 | Bejar et al. |
| 2006/0081711 A1 | 4/2006 | Zhao et al. |
| 2006/0110714 A1 | 5/2006 | Symmes |
| 2006/0129381 A1 | 6/2006 | Wakita |
| 2006/0247914 A1 | 11/2006 | Brener et al. |
| 2006/0260958 A1 | 11/2006 | Brunner |
| 2007/0067177 A1 | 3/2007 | Martin |
| 2007/0094024 A1 | 4/2007 | Kristensson et al. |
| 2007/0106937 A1 | 5/2007 | Cucerzan et al. |
| 2007/0141544 A1 | 6/2007 | Nakane |
| 2007/0238084 A1 | 10/2007 | Maguire et al. |
| 2007/0265831 A1 | 11/2007 | Dinur et al. |
| 2007/0271089 A1 | 11/2007 | Bates et al. |
| 2008/0059151 A1 | 3/2008 | Chen |
| 2008/0077859 A1 | 3/2008 | Schabes et al. |
| 2008/0154600 A1 | 6/2008 | Tian et al. |
| 2008/0167858 A1 | 7/2008 | Christie et al. |
| 2008/0173712 A1 | 7/2008 | Nemet |
| 2008/0189106 A1 | 8/2008 | Low et al. |
| 2008/0195940 A1 | 8/2008 | Gail et al. |
| 2008/0208567 A1 | 8/2008 | Brockett et al. |
| 2008/0208582 A1 | 8/2008 | Gallino |
| 2008/0249773 A1 | 10/2008 | Bejar et al. |
| 2008/0270897 A1 | 10/2008 | Jawerth et al. |
| 2009/0083028 A1 | 3/2009 | Davtchev et al. |
| 2009/0198671 A1 | 8/2009 | Zhang |
| 2009/0228467 A1 | 9/2009 | Asanuma |
| 2009/0230182 A1 | 9/2009 | Nemet et al. |
| 2009/0302102 A1 | 12/2009 | Nemet et al. |
| 2009/0319257 A1 | 12/2009 | Blume et al. |
| 2009/0320742 A1 | 12/2009 | Leute et al. |
| 2010/0020970 A1 | 1/2010 | Liu |
| 2010/0050074 A1 | 2/2010 | Nachmani et al. |
| 2010/0219235 A1 | 9/2010 | Nemet et al. |
| 2010/0269454 A1 | 10/2010 | Reddersen et al. |
| 2010/0275118 A1 | 10/2010 | Iakobashvili et al. |
| 2010/0286979 A1 | 11/2010 | Zangvil et al. |
| 2011/0006109 A1 | 1/2011 | Nemet |
| 2011/0006115 A1 | 1/2011 | Nemet |
| 2011/0093268 A1 | 4/2011 | Gorin et al. |
| 2011/0184720 A1 | 7/2011 | Zangvil |
| 2012/0104105 A1 | 5/2012 | Nemet |
| 2012/0104106 A1 | 5/2012 | Nemet |
| 2012/0145781 A1 | 6/2012 | Nemet |
| 2012/0305637 A1 | 12/2012 | Nemet |
| 2013/0024185 A1 | 1/2013 | Parikh |
| 2013/0074248 A1 | 3/2013 | Evans et al. |
| 2013/0138641 A1 | 5/2013 | Korolev et al. |
| 2013/0334301 A1 | 12/2013 | Nemet et al. |
| 2014/0001256 A1 | 1/2014 | Nemet et al. |
| 2014/0110486 A1 | 4/2014 | Nemet |
| 2014/0252096 A1 | 9/2014 | Nemet et al. |
| 2014/0353385 A1 | 12/2014 | Nemet |
| 2014/0360269 A1 | 12/2014 | Burghardt et al. |
| 2015/0047552 A1 | 2/2015 | Ortais |
| 2015/0053776 A1 | 2/2015 | Nemet et al. |
| 2015/0100105 A1 | 4/2015 | Kiani et al. |
| 2015/0122880 A1 | 5/2015 | Nemet et al. |
| 2015/0168223 A1 | 6/2015 | Hammond et al. |
| 2015/0193677 A1 | 7/2015 | Nemet et al. |
| 2015/0220877 A1 | 8/2015 | Nemet et al. |
| 2016/0042260 A1 | 2/2016 | Nemet |
| 2016/0071000 A1 | 3/2016 | Nemet et al. |
| 2016/0239781 A1 | 8/2016 | Nemet et al. |
| 2016/0275390 A1 | 9/2016 | Nemet et al. |
| 2016/0292554 A1 | 10/2016 | Nemet et al. |
| 2016/0371576 A1 | 12/2016 | Nemet et al. |
| 2016/0371577 A1 | 12/2016 | Nemet |
| 2016/0371635 A1 | 12/2016 | Nemet et al. |
| 2017/0177987 A1 | 6/2017 | Nemet et al. |

FOREIGN PATENT DOCUMENTS

| | | |
|---|---|---|
| CN | 101365934 | 2/2009 |
| CN | 204176727 | 2/2015 |
| EP | 936753 | 8/1999 |
| JP | S57-59293 | 4/1982 |
| JP | 63094383 | 4/1988 |
| JP | 63-118894 | 5/1988 |
| JP | 3-53281 | 3/1991 |
| JP | 5-6470 | 1/1993 |
| JP | 5-19695 | 1/1993 |
| JP | 5-67253 | 3/1993 |
| JP | 9-504858 | 11/1994 |
| JP | 2006-522933 | 5/1997 |
| JP | 2001-502794 | 2/2001 |
| JP | 2001-194248 | 7/2001 |
| JP | 2002-040012 | 2/2002 |
| JP | 2002/504684 | 2/2002 |
| JP | 2003-203210 | 7/2003 |
| JP | 2003/525464 | 8/2003 |
| JP | 2005-518320 | 6/2005 |
| JP | 2006-18782 | 1/2006 |
| JP | 2007121017 | 5/2007 |
| JP | 2004-184920 | 7/2007 |
| JP | 2008/089673 | 4/2008 |
| WO | 1994/27144 | 11/1994 |
| WO | 1994/27155 | 11/1994 |
| WO | 1997/011535 | 3/1997 |
| WO | 1998/14777 | 4/1998 |
| WO | 1998/035514 | 12/1998 |
| WO | 1999/042822 | 8/1999 |
| WO | 2001/048680 | 7/2001 |
| WO | 2001/064430 | 9/2001 |
| WO | 2003/060626 | 7/2003 |
| WO | 2004/038353 | 5/2004 |
| WO | 2004/038535 | 5/2004 |
| WO | 2004/092697 | 10/2004 |
| WO | 2006-086053 | 8/2006 |
| WO | 2007-049792 | 5/2007 |
| WO | 2008/022140 | 2/2008 |
| WO | 09/016631 | 2/2009 |
| WO | 2007/129316 | 4/2009 |
| WO | 2008/135962 | 4/2009 |
| WO | 2009/063464 | 5/2009 |
| WO | 2009/063465 | 5/2009 |
| WO | 2009-144701 | 12/2009 |
| WO | 2009/150641 | 12/2009 |
| WO | 10/013228 | 2/2010 |
| WO | 2010/134061 | 11/2010 |
| WO | 2010/134062 | 11/2010 |

(56) References Cited

FOREIGN PATENT DOCUMENTS

| WO | 2016/185474 | 11/2016 |
|---|---|---|
| WO | 2006/134795 | 12/2016 |
| WO | 2017/006326 | 1/2017 |

OTHER PUBLICATIONS

An Office Action dated Oct. 11, 2016, which issued during the prosecution of U.S. Appl. No. 15/184,483.
A Notice of Allowance dated Nov. 18, 2014, which issued during the prosecution of U.S. Appl. No. 13/323,906.
A Notice of Allowance dated Apr. 23, 2014, which issued during the prosecution of U.S. Appl. No. 13/323,906.
An Office Action dated May 5, 2016, which issued during the prosecution of Canadian Patent Application No. 2,762,894.
A Notice of Allowance dated Apr. 25, 2014, which issued during the prosecution of U.S. Appl. No. 13/490,705.
A Notice of Allowance dated Nov. 7, 2014, which issued during the prosecution of U.S. Appl. No. 13/490,705.
An English translation of an Office Action dated Feb. 3, 2014 which issued during the prosecution of Japanese Patent Application No. 2012-511407.
An English translation of an Office Action dated Aug. 26, 2014 which issued during the prosecution of Japanese Patent Application No. 2012-511407.
An Office Action dated Mar. 6, 2015, which issued during the prosecution of U.S. Appl. No. 14/055,422.
An English translation of an Office Action dated Jun. 25, 2013 which issued during the prosecution of Janese Patent Application No. 2012-511406.
An Office Action dated Nov. 7, 2012, which issued during the prosecution of U.S. Appl. No. 12/743,209.
An English Translation of an Office Action dated Dec. 24, 2013 which issued during the prosecution of Chinese Patent Application No. 200980160387.4.
An Office Action dated Mar. 9, 2012, which issued during the prosecution of U.S. Appl. No. 12/743,209.
Notice of Allowance dated Apr. 14, 2014, which issued during the prosecution of U.S. Appl. No. 13/657,185.
An Office Action dated Jan. 16, 2013, which issued during the prosecution of U.S. Appl. No. 12/598,979.
An Office Action dated Dec. 19, 2012, which issued during the prosecution of U.S. Appl. No. 12/742,650.
An Office Action dated Mar. 20, 2012, which issued during the prosecution of U.S. Appl. No. 13/321,477.
An Office Action dated Aug. 14, 2015, which issued during the prosecution of U.S. Appl. No. 14/055,422.
An English Translation of an Office Action dated Feb. 26, 2013 which issued during the prosecution of Japanese Patent Application No. JP2009-508663.
An English Translation of an Office Action dated Jan. 15, 2013 which issued during the prosecution of Japanese Patent Application No. JP2010-507054.
An Extended European Search Report dated Feb. 11, 2013, which issued during the prosecution of European Patent Application No. 08848845.
An Extended European Search Report dated Feb. 18, 2013, which issued during the prosecution of European Application No. 09762166.
An Office Action dated Nov. 7, 2011, which issued during the prosecution of U.S. Appl. No. 12/598,979.
An International Preliminary Report on Patentability dated Nov. 22, 2011 which issued during the prosecution of Applicant's PCT/IL10/00205.
U.S. Appl. No. 60/746,646, filed May 7, 2006.
U.S. Appl. No. 60/804,072, filed Jun. 6, 2006.
U.S. Appl. No. 61/231,799, filed Aug. 6, 2009.
U.S. Appl. No. 61/131,644, filed Jun. 10, 2008.

An Office Action dated Oct. 28, 2013, which issued during the prosecution of U.S. Appl. No. 14/017,545.
An Office Action dated Jun. 20, 2008, which issued during the prosecution of U.S. Appl. No. 11/852,911.
An International Search Report and a Written Opinion both dated Jul. 17, 2008, which issued during the prosecution of Applicant's PCTIL2007000547.
An International Preliminary Report on Patentability dated Mar. 10, 2009, which issued during the prosecution of Applicant's PCTIL2007000547.
An International Search Report and a Written Opinion both dated Jan. 9, 2009, which issued during the prosecution of Applicant's PCT/IL2007/001411.
An International Preliminary Report on Patentability dated Nov. 10, 2009, which issued during the prosecution of Applicant's PCT/IL2007/001411.
A Notice of Allowance dated Feb. 15, 2012, which issued during the prosecution of U.S. Appl. No. 12/471,798.
European Search Report dated Aug. 18, 2011, which issued during the prosecution of European Patent Application No. 0 773 6287.
An Office Action dated Apr. 19, 2011, which issued during the prosecution of U.S. Appl. No. 12/469,309.
A Notice of Allowance dated Sep. 9, 2011, which issued during the prosecution of U.S. Appl. No. 12/469,309.
An Office Action dated May 3, 2011, which issued during the prosecution of U.S. Appl. No. 12/471,798.
An International Search Report and a Written Opinion both dated Aug. 31, 2009, which issued during the prosecution of Applicant's PCT/IL2009/000503.
An International Preliminary Report on Patentability dated Dec. 13, 2010, which issued during the prosecution of Applicant's PCT/IL2009/000503.
An International Search Report and a Written Opinion both dated Apr. 5, 2010, which issued during the prosecution of Applicant's PCT/IL2009/001167.
An International Preliminary Report on Patentability dated Nov. 22, 2011, which issued during the prosecution of Applicant's PCT/IL2009/001167.
A Notice of Allowance dated Apr. 2, 2013, which issued during the prosecution of U.S. Appl. No. 12/743,209.
An English Translation of an Office Action dated May 22, 2015 which issued during the prosecution of Chinese Patent Application No. 200980160387.4.
An Office Action dated Sep. 10, 2013, which issued during the prosecution of U.S. Appl. No. 13/657,185.
An English translation of an Office Action dated Sep. 10, 2013 which issued during the prosecution of Japanese Patent Application No. 2011-513110.
An English translation of an Office Action dated Aug. 27, 2013 which issued during the prosecution of Japanese Patent Application No. 2010-507054.
An Examiner Interview Summary Report dated Nov. 7, 2008, which issued during the prosecution of U.S. Appl. No. 11/852,911.
A Notice of Allowance dated Feb. 25, 2009, which issued during the prosecution of U.S. Appl. No. 11/852,911.
An Office Action dated Mar. 15, 2013, which issued during the prosecution of U.S. Appl. No. 13/321,467.
A Notice of Allowance dated Jul. 11, 2013, which issued during the prosecution of U.S. Appl. No. 13/321,477.
An Office Action dated Jul. 12, 2013, which issued during the prosecution of European Patent Application No. 07736287.9.
A Notice of Allowance dated May 16, 2013, which issued during the prosecution of U.S. Appl. No. 12/742,650.
An Office Action dated Sep. 18, 2014, which issued during the prosecution of U.S. Appl. No. 14/143,827.
A Notice of Allowance dated Oct. 15, 2014, which issued during the prosecution of U.S. Appl. No. 14/017,545.
A Notice of Allowance dated Apr. 17, 2009, which issued during the prosecution of U.S. Appl. No. 11/852,911.
An Office Action dated Sep. 9, 2011, which issued during the prosecution of U.S. Appl. No. 12/471,798.
An Office Action dated Oct. 12, 2012, which issued during the prosecution of U.S. Appl. No. 12/669,175.

(56) References Cited

OTHER PUBLICATIONS

An Office Action dated Aug. 5, 2013, which issued during the prosecution of U.S. Appl. No. 12/669,175.
An Office Action dated Feb. 5, 2013, which issued during the prosecution of U.S. Appl. No. 12/669,175.
An Office Action dated Mar. 7, 2014, which issued during the prosecution of U.S. Appl. No. 12/669,175.
A Notice of Allowance dated Aug. 4, 2014, which issued during the prosecution of U.S. Appl. No. 12/669,175.
An English Translation of an Office Action dated Apr. 22, 2014 which issued during the prosecution of Israeli Patent Application No. 205687.
An English Translation of an Office Action dated Oct. 27, 2014 which issued during the prosecution of Israeli Patent Application No. 209901.
A Notice of Allowance dated Dec. 14, 2016, which issued during the prosecution of U.S. Appl. No. 15/189,127.
An Office Action dated Jul. 1, 2014, which issued during the prosecution of U.S. Appl. No. 13/576,330.
An International Search Report and a Written Opinion both dated Oct. 3, 2016, which issued during the prosecution of Applicant's PCT/IL2016/050526.
An English Translation of an Office Action dated Jun. 13, 2014 which issued during the prosecution of Chinese Patent Application No. 200880101405.7.
An Office Action dated Nov. 23, 2016, which issued during the prosecution of U.S. Appl. No. 15/063,804.
Letter submitted on Jul. 17, 2009 in U.S. Appl. No. 11/852,911.
A Notice of Allowance dated Oct. 26 2016, which issued during the prosecution of U.S. Appl. No. 15/189,127.
An Office Action dated May 9, 2013, which issued during the prosecution of U.S. Appl. No. 12/937,618.
An English Translation of an Office Action dated Jan. 25, 2013 which issued during the prosecution of Chinese Patent Application No. 200880101405.7.
Notice of Allowance dated Jan. 5, 2017, which issued during the prosecution of U.S. Appl. No. 15/183,465.
An English Translation of an Office Action dated Apr. 28, 2012 which issued during the prosecution of Chinese Patent Application No. 200880101405.7.
Notice of Allowance dated May 13, 2015, which issued during the prosecution of U.S. Appl. No. 14/461,778.
A Notice of Allowance dated Jun. 27, 2014, which issued during the prosecution of U.S. Appl. No. 14/017,545.
A Supplementary European Search Report dated Jul. 5, 2012, which issued during the prosecution of European Patent Application No. 08789727.
An English Translation of an Office Action dated Jun. 23, 2011 which issued during the prosecution of Chinese Patent Application No. 200880101405.7.
An International Search Report and a Written Opinion both dated May 25, 2011, which issued during the prosecution of Applicant's PCT/IL2011/00088.
An International Search Report dated May 11, 2009, which issued during the prosecution of Applicant's PCT/IL2009/00130.
An International Search Report dated Jun. 26, 2009, which issued during the prosecution of Applicant's PCT/IL2009/00317.
An International Preliminary Examination Report dated Oct. 19, 2010, which issued during the prosecution of Applicant's PCT/IL2009/00317.
Bick, E., "A Constraint Grammar Based Spellchecker for Danish with a Special Focus on Dyslexics" SKY Journal of Linguistics, vol. 19:2006 (ISSN 1796-279X), pp. 387-396 (retrieved Jan. 12, 2009 from the internet). <URL http://www.ling.helsinki.fi/sky/julkaisut/SKY2006_1/1.6.1%20BICK.pdf>.
An International Search Report and Written Opinion both dated Feb. 3, 2009 which issued during the prosecution of Applicant's PCT/IL08/01051.
An Office Action dated Jan. 10, 2014, which issued during the prosecution of European Patent Application No. 08848845.

An Office Action dated Jun. 5, 2014, which issued during the prosecution of U.S. Appl. No. 14/017,545.
A Notice of Allowance dated Apr. 26, 2013, which issued during the prosecution of U.S. Appl. No. 12/598,979.
A Supplementary European Search Report dated Apr. 13, 2011, which issued during the prosecution of European Patent Application No. 07827384.
An English Translation of an Office Action dated Feb. 7, 2012 which issued during the prosecution of Japanese Patent Application No. JP2009-508663.
A Supplementary European Search Report dated Aug. 23, 2012, which issued during the prosecution of European Patent Application No. 08849330.9.
An International Preliminary Report on Patentability dated May 18, 2010, which issued during the prosecution of Applicant's PCT/IL2008/001495.
An International Preliminary Report on Patentability dated May 18, 2010, which issued during the prosecution of Applicant's PCT/IL2008/001494.
An International Search Report and a Written Opinion both dated Jun. 3, 2009, which issued during the prosecution of Applicant's PCT/IL2008/001494.
An International Search Report and a Written Opinion both dated Jun. 8, 2010, which issued during the prosecution of Applicant's PCT/IL2010/000205.
An International Search Report and a Written Opinion both dated Mar. 9, 2009, which issued during the prosecution of Applicant's PCT/IL2008/001495.
An Office Action dated Apr. 25, 2012, which issued during the prosecution of U.S. Appl. No. 12/598,979.
An English Translation of an Office Action dated Oct. 25, 2012 which issued during the prosecution of Israeli Patent Application No. 201958.
An Office Action dated Jan. 21, 2015, which issued during the prosecution of U.S. Appl. No. 14/461,778.
An Office Action dated Feb. 11, 2015, which issued during the prosecution of U.S. Appl. No. 13/958,893.
An English Translation of an Office Action dated Feb. 18, 2014 which issued during the prosecution of Japanese Patent Application No. JP2009-508663.
U.S. Appl. No. 60/963,956, filed Aug. 6, 2007.
U.S. Appl. No. 60/959,120, filed Jul. 10, 2007.
An Office Action dated Sep. 25, 2014, which issued during the prosecution of U.S. Appl. No. 14/461,778.
An English Translation of an Office Action dated Nov. 4, 2014 which issued during the prosecution of Chinese Patent Application No. 201080030956.6.
An English Translation of an Office Action dated Apr. 19, 2015 which issued during the prosecution of Israeli Patent Application No. 216396.
An English Translation of an Office Action dated Nov. 15, 2014 which issued during the prosecution of Chinese Patent Application No. 200980160387.4.
An English Translation of an Office Action dated Jan. 6, 2014 which issued during the prosecution of Chinese Patent Application No. 201080030956.6.
An English translation of an Office Action dated Jul. 28, 2015 which issued during the prosecution of Japanses Patent Application No. 2014-125707.
Notice of Allowance dated May 29, 2015, which issued during the prosecution of U.S. Appl. No. 13/958,893.
An Office Action dated Jul. 28, 2015, which issued during the prosecution of U.S. Appl. No. 14/595,412.
U.S. Appl. No. 62/163,193, filed May 18, 2015.
U.S. Appl. No. 62/189,367, filed Jul. 7, 2015.
An English translation of an Office Action dated Aug. 27, 2015 which issued during the prosecution of Japanese Patent Application No. 2014-218223.
An English Translation of an Office Action dated Dec. 31, 2015 which issued during the prosecution of Israeli Patent Application No. 209901.

(56) References Cited

OTHER PUBLICATIONS

An English Translation of an Office Action dated Apr. 20, 2015 which issued during the prosecution of Israeli Patent Application No. 216397.
A Supplementary European Search Report dated Sep. 23, 2015, which issued during the prosecution of European Patent Application No. 10777451.5.
European Search Report dated Sep. 16, 2015, which issued during the prosecution of European Patent Application No. 09844849.
A Notice of Allowance dated Dec. 8, 2015, which issued during the prosecution of U.S. Appl. No. 14/055,422.
A Notice of Allowance dated Jan. 18, 2017, which issued during the prosecution of U.S. Appl. No. 15/137,316.
An Office Action dated Nov. 19, 2013, which issued during the prosecution of European Application No. 07827384.4.
A Notice of Allowance dated Mar. 23, 2016, which issued during the prosecution of U.S. Appl. No. 14/823,758.
A Notice of Allowance dated Feb. 4, 2016, which issued during the prosecution of U.S. Appl. No. 14/595,395.
An Office Action dated Dec. 4, 2015, which issued during the prosecution of U.S. Appl. No. 14/823,758.
A Notice of Allowance dated Feb. 2, 2016, which issued during the prosecution of U.S. Appl. No. 14/595,412.
A Notice of Allowance dated Mar. 16, 2016, which issued during the prosecution of U.S. Appl. No. 14/595,954.
A Notice of Allowance dated Mar. 3, 2016, which issued during the prosecution of U.S. Appl. No. 14/528,186.
A Notice of Allowance dated Oct. 11, 2016, which issued during the prosecution of U.S. Appl. No. 14/823,702.
An English translation of an Office Action dated Jun. 14, 2016 which issued during the prosecution of Japanese Patent Application No. 2014-125707.
An English translation of an Office Action dated Mar. 15, 2016, which issued during the prosecution of Japanese Patent Application No. 2014-218223.
An Office Action dated Jan. 29, 2016, which issued during the prosecution of U.S. Appl. No. 14/595,954.
An Office Action dated Sep. 27, 2016, which issued during the prosecution of U.S. Appl. No. 15/189,127.
An Office Action dated Jun. 27, 2016, which issued during the prosecution of U.S. Appl. No. 14/823,702.
An Office Action dated Jan. 29, 2016, which issued during the prosecution of U.S. Appl. No. 14/528,186.
An Office Action dated Jan. 26, 2016, which issued during the prosecution of Canadian Patent Application No. 2762891.
An International Search Report and a Written Opinion both dated Dec. 12, 2016, which issued during the prosecution of Applicant's PCT/IL2016/050727.
An Office Action dated Jan. 24, 2017, which issued during the prosecution of Canadian Patent Application No. 2,762,894.
An Office Action dated Dec. 13, 2016, which issued during the prosecution of U.S. Appl. No. 15/169,851.
An Office Action dated Jun. 29, 2017, which issued during the prosecution of U.S. Appl. No. 15/169,851.
An English translation of an Office Action dated Nov. 2, 2016, which issued during the prosecution of Japanese Patent Application No. 2014-125707.
Notice of Allowance dated Mar. 23, 2017, which issued during the prosecution of U.S. Appl. No. 15/169,851.
Notice of Allowance dated Mar. 20, 2017, which issued during the prosecution of U.S. Appl. No. 15/063,804.
Notice of Allowance dated Aug. 3, 2017, which issued during the prosecution of U.S. Appl. No. 15/398,951.
An Office Action dated Jun. 28, 2017, which issued during the prosecution of U.S. Appl. No. 15/495,022.
An Office Action dated Jul. 27, 2017, which issued during the prosecution of U.S. Appl. No. 15/184,483.
An Office Action dated Jul. 26, 2017, which issued during the prosecution of U.S. Appl. No. 15/486,906.
An Office Action together with the English translation dated Sep. 5, 2017, which issued during the prosecution of Japanese Patent Application No. 2016-200656.
An English translation of an Office Action dated Dec. 7, 2017 which issued during the prosecution of Japanese Patent Application No. 2014-125707.
An Office Action dated Jan. 2, 2018, which issued during the prosecution of U.S. Appl. No. 15/184,483.

* cited by examiner

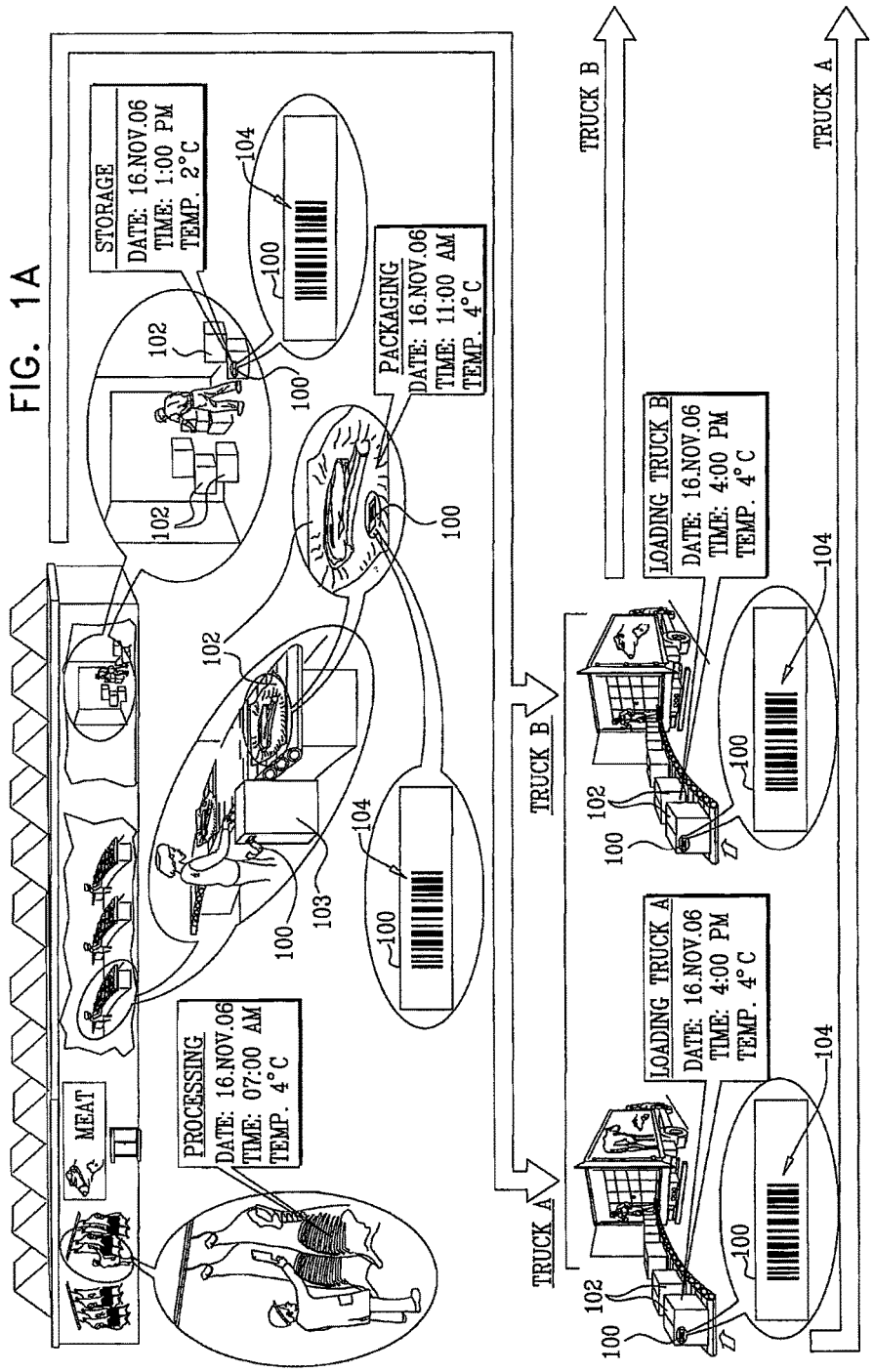

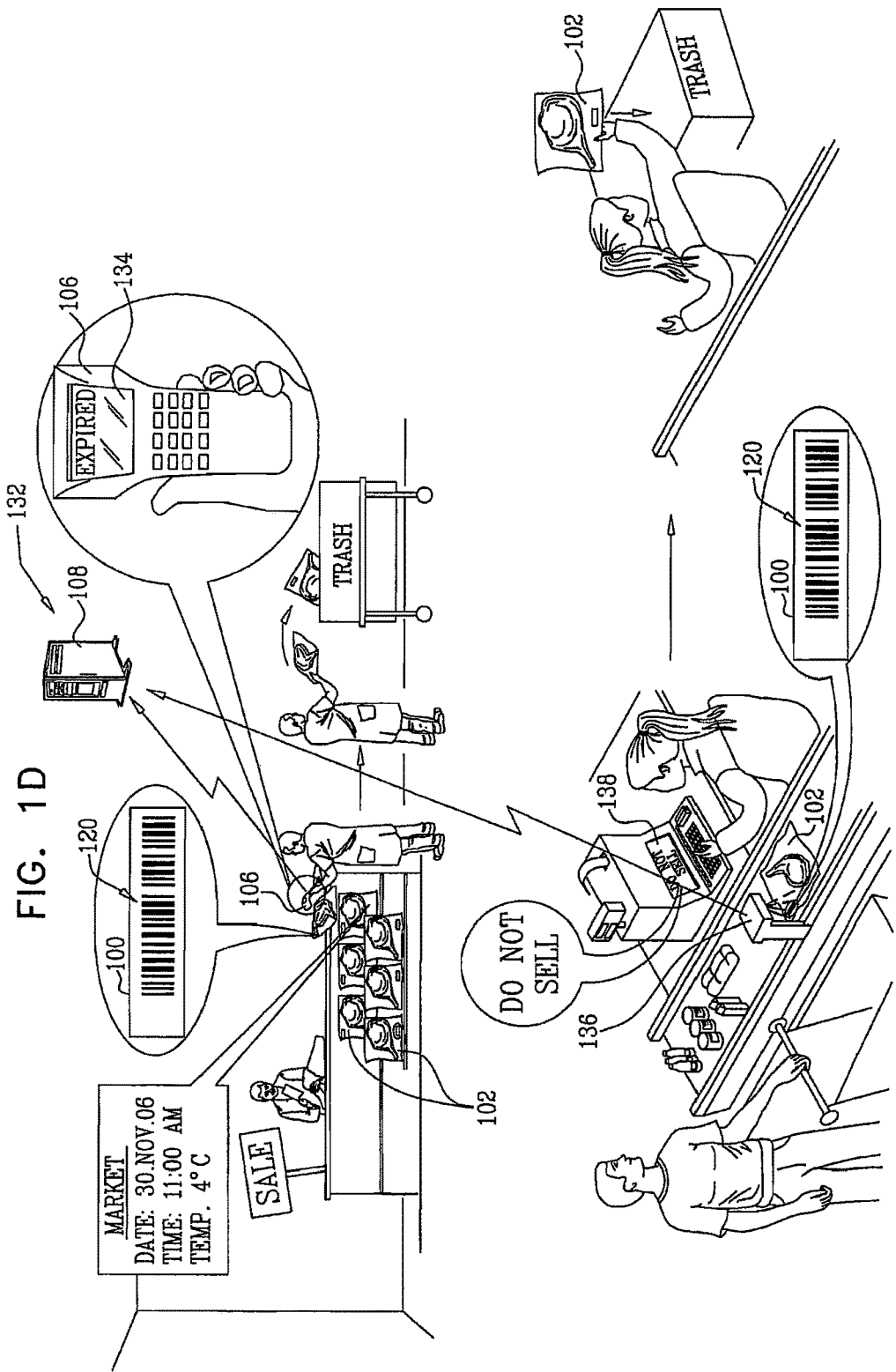

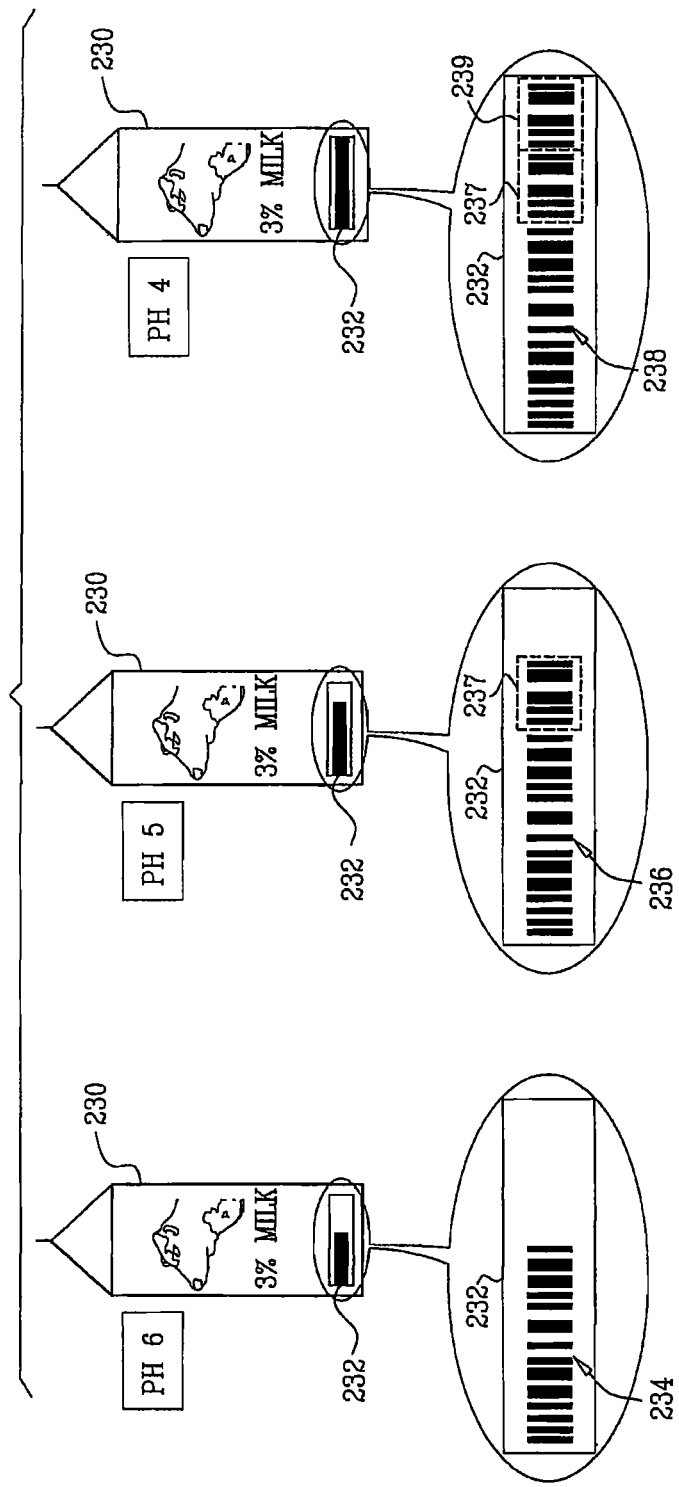

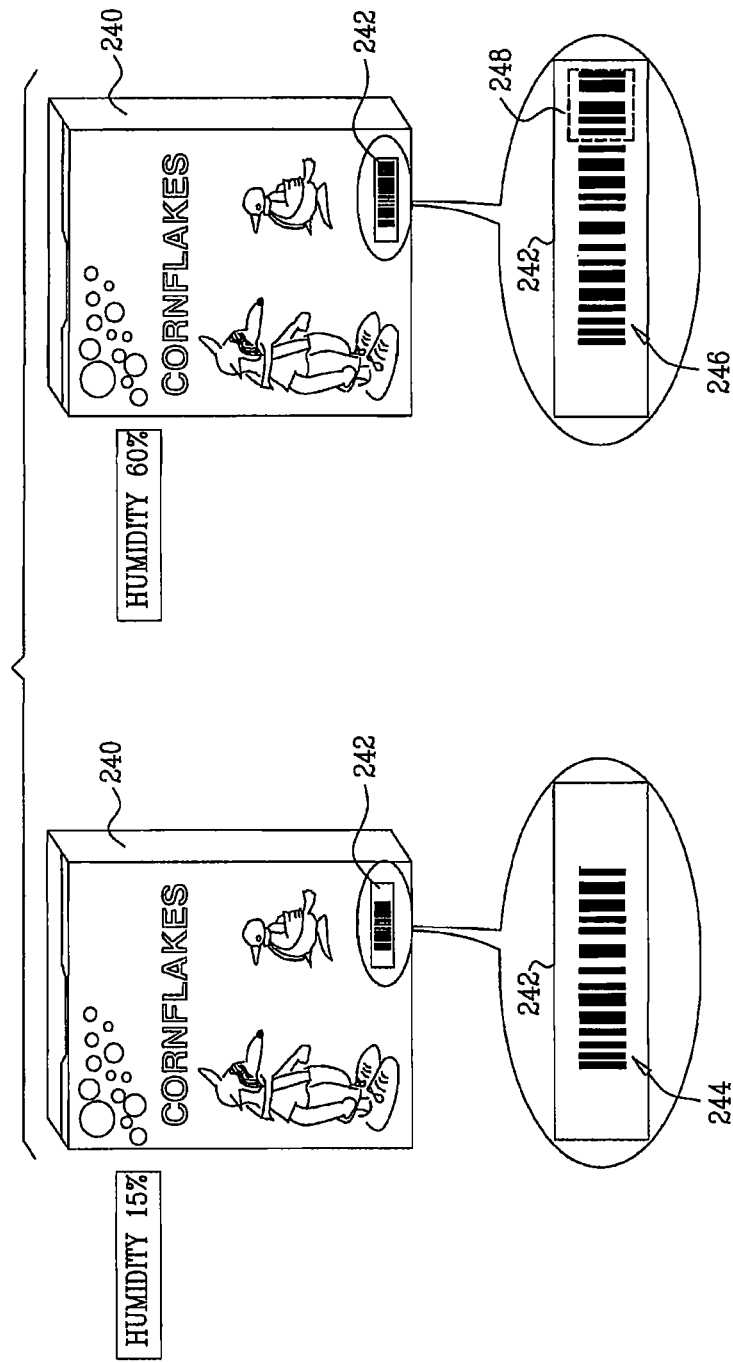

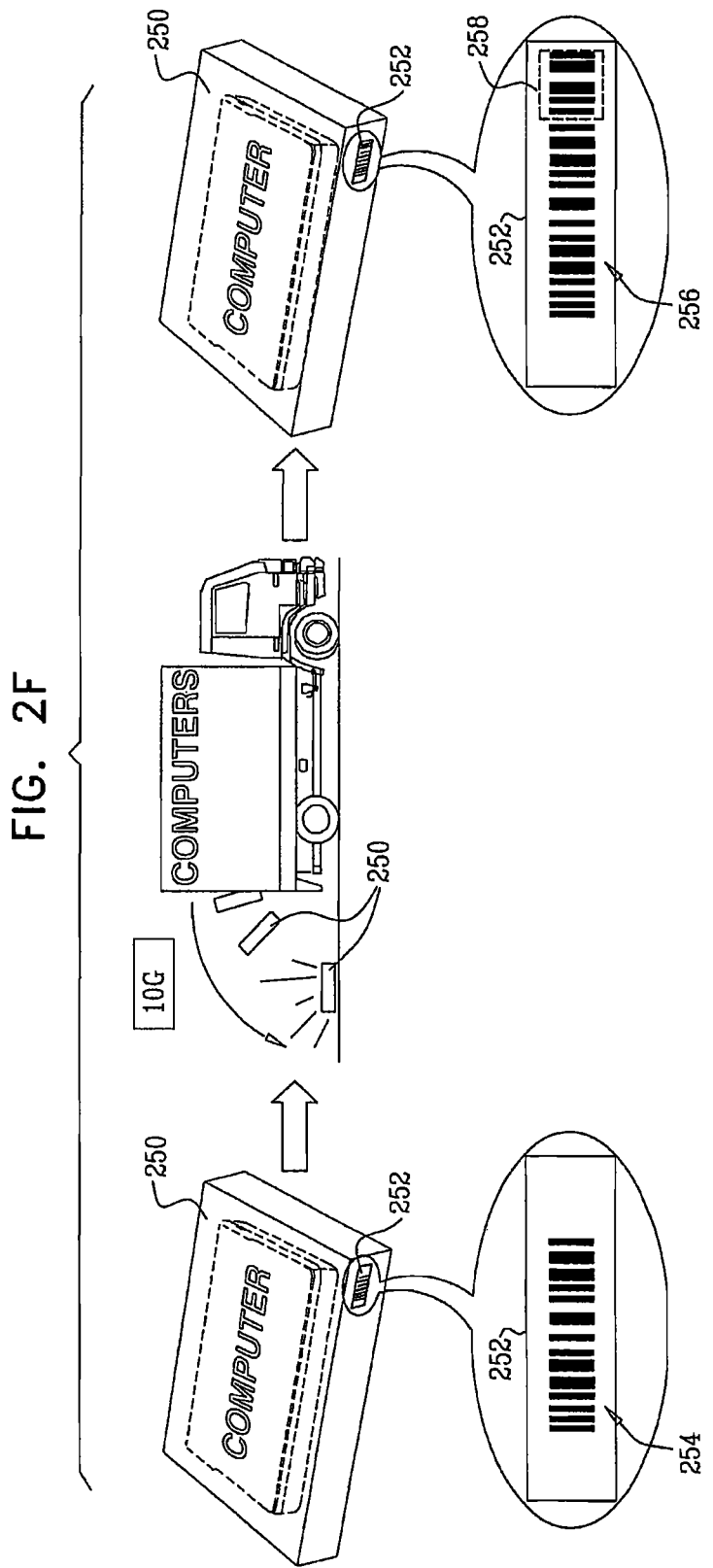

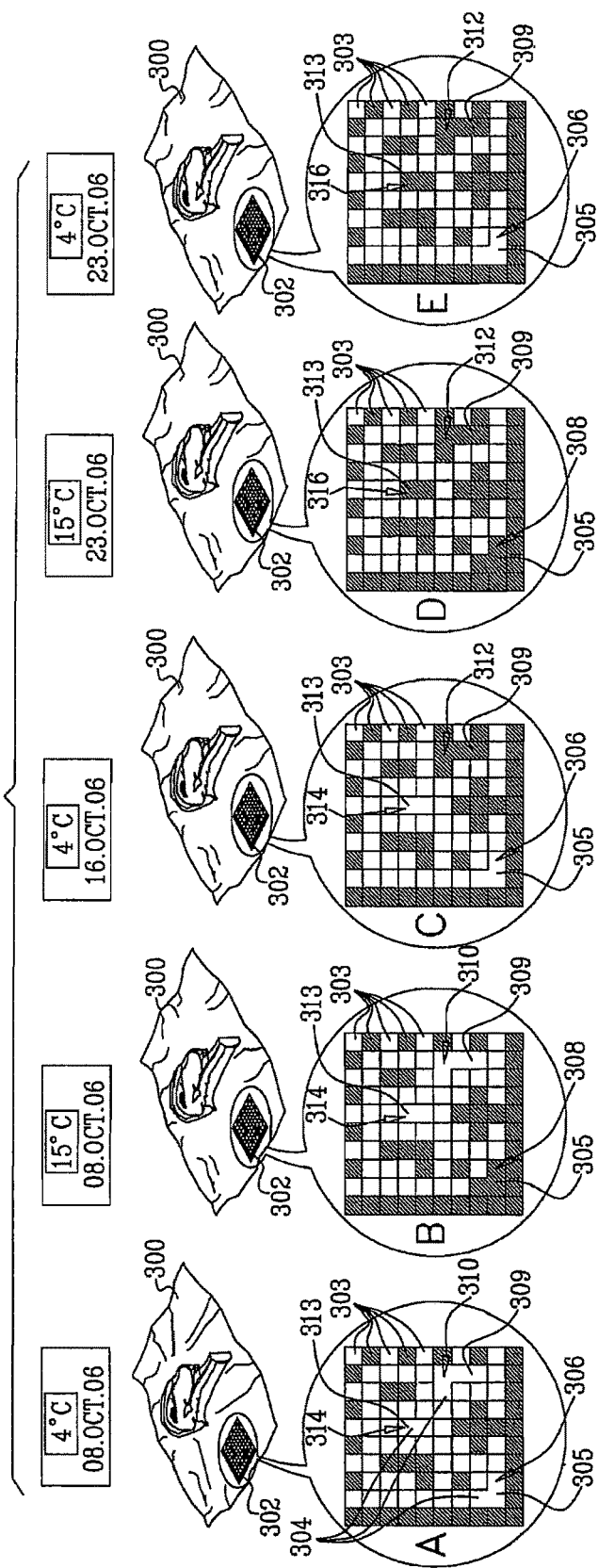

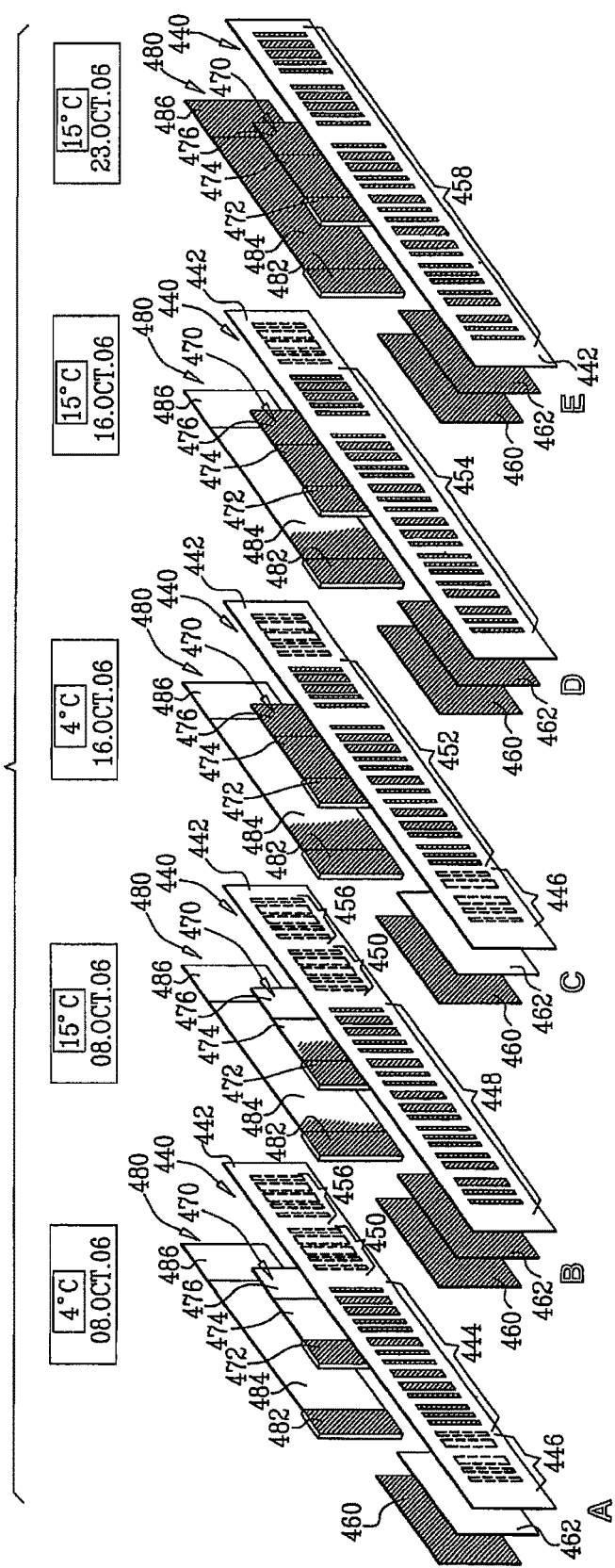

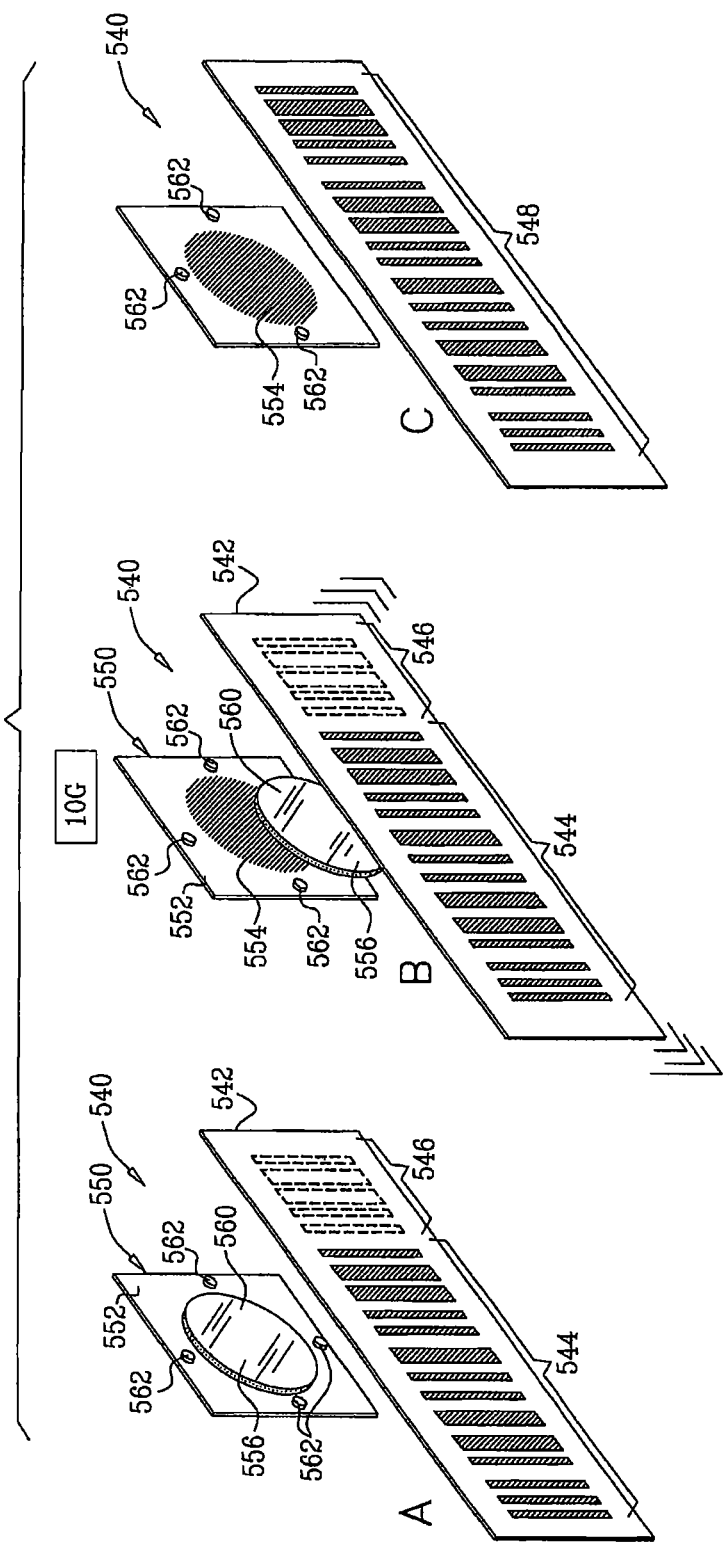

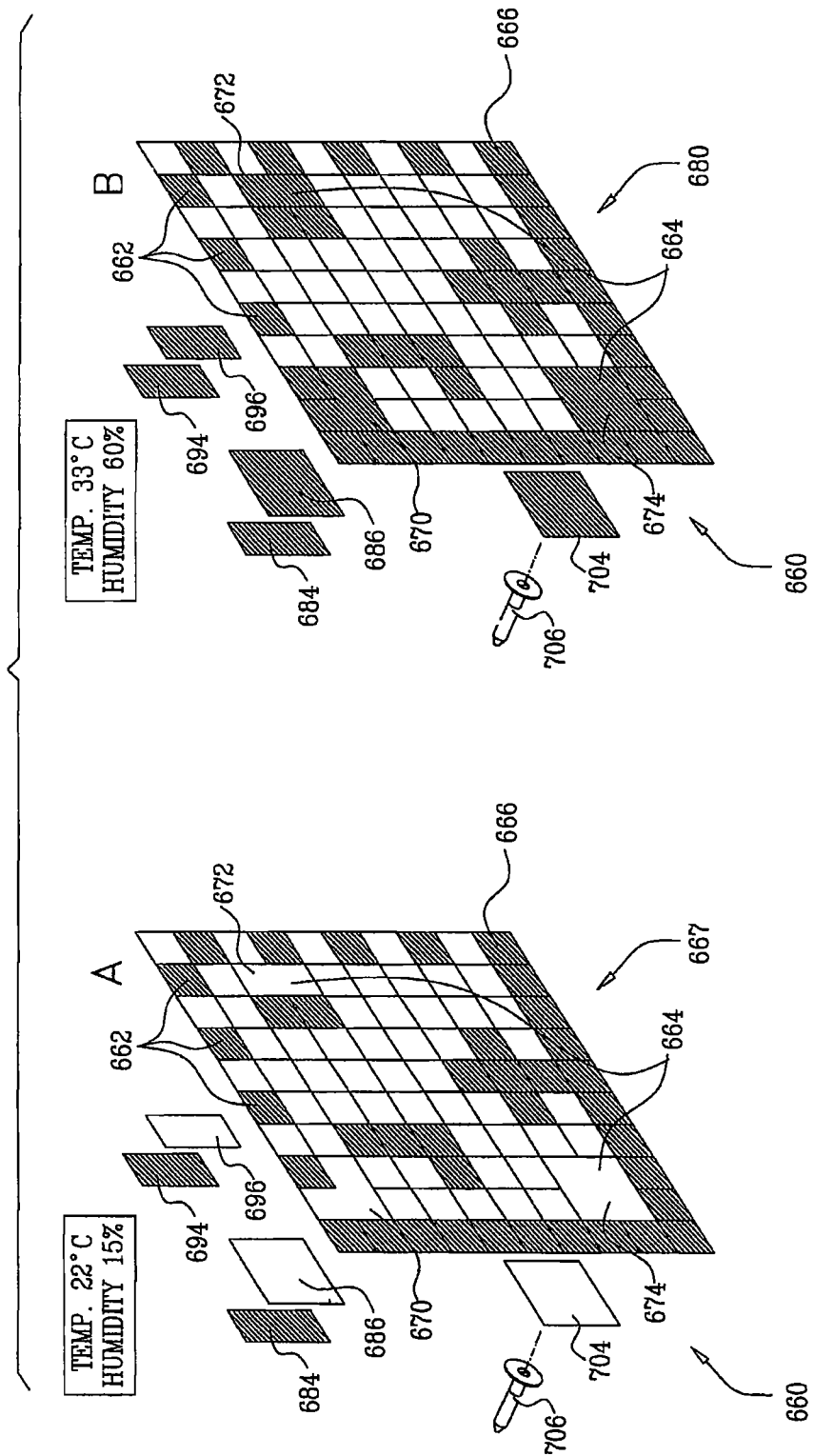

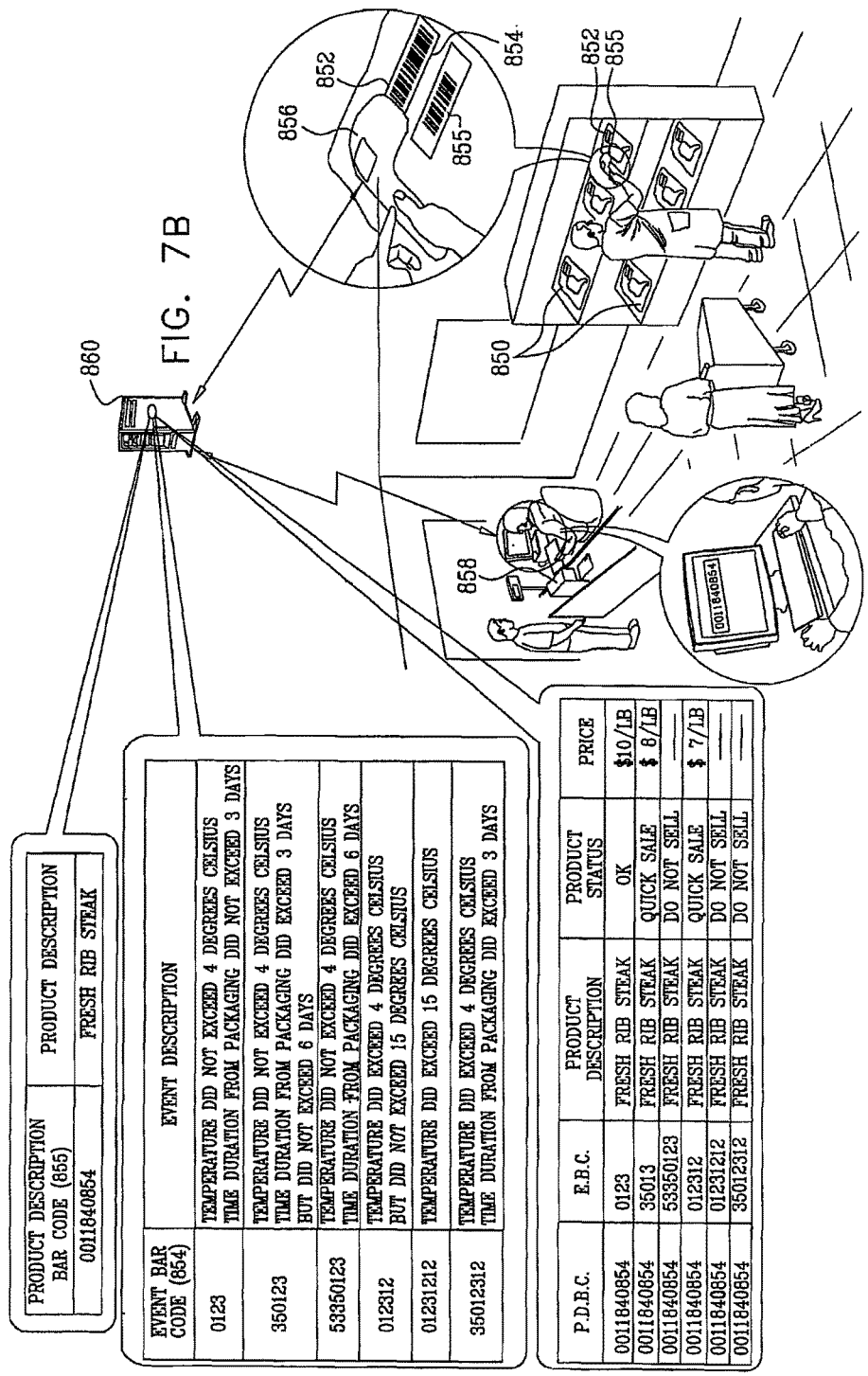

SYSTEM AND METHOD FOR IMPROVED QUALITY MANAGEMENT IN A PRODUCT LOGISTIC CHAIN

REFERENCE TO RELATED APPLICATIONS

This application is a continuation of U.S. patent application Ser. No. 15/137,316, filed Apr. 25, 2016, entitled "SYSTEM AND METHOD FOR IMPROVED QUALITY MANAGEMENT IN A PRODUCT LOGISTIC CHAIN", now U.S. Pat. No. 9,646,277, which is a continuation of U.S. patent application Ser. No. 14/595,395, filed Jan. 13, 2015, entitled "SYSTEM AND METHOD FOR IMPROVED QUALITY MANAGEMENT IN A PRODUCT LOGISTIC CHAIN", now U.S. Pat. No. 9,349,086, which is a continuation of U.S. patent application Ser. No. 13/490,705, filed Jun. 7, 2012, entitled "SYSTEM AND METHOD FOR IMPROVED QUALITY MANAGEMENT IN A PRODUCT LOGISTIC CHAIN", now U.S. Pat. No. 8,967,467, which is a continuation of U.S. patent application Ser. No. 12/471,798, filed May 26, 2009, entitled "SYSTEM AND METHOD FOR IMPROVED QUALITY MANAGEMENT IN A PRODUCT LOGISTIC CHAIN", now U.S. Pat. No. 8,196,821, which is a continuation of U.S. patent application Ser. No. 11/852,911, filed Sep. 10, 2007, entitled "SYSTEM AND METHOD FOR IMPROVED QUALITY MANAGEMENT IN A PRODUCT LOGISTIC CHAIN", now U.S. Pat. No. 7,562,811, which is a continuation of U.S. patent application Ser. No. 11/624,492, filed Jan. 18, 2007, entitled "SYSTEM AND METHOD FOR IMPROVED QUALITY MANAGEMENT IN A PRODUCT LOGISTIC CHAIN", now abandoned.

FIELD OF THE INVENTION

The present invention relates to quality management systems and methodologies and to indicators useful in such systems and methodologies.

BACKGROUND OF THE INVENTION

The following U.S. Patents relate generally to the subject matter of the present application: U.S. Pat. Nos. 6,758,397; 6,009,400 and RE 39,226.

SUMMARY OF THE INVENTION

The present invention seeks to provide improved quality management systems and methodologies as well as indicators useful in such systems and methodologies.

There is thus provided in accordance with a preferred embodiment of the present invention a quality management system for products including a multiplicity of product unit specific indicators, each operative to provide a machine-readable indication of exceedence of at least one threshold by at least one product quality determining parameter, an indicator reader operative to read the product unit specific indicators and to provide output indications and a product type specific indication interpreter operative to receive the output indications and to provide human sensible, product unit specific, product quality status outputs.

Preferably, the indicator reader is a bar code reader. Additionally or alternatively, the machine-readable indications are in the form of bar codes. Additionally, the bar codes are one-dimensional bar codes. Alternatively, the bar codes are two-dimensional bar codes.

Preferably, the at least one threshold includes at least a temperature threshold and an elapsed time threshold. Additionally or alternatively, the at least one threshold includes at least a pH threshold.

Preferably, the machine-readable indications each include a variable bar code having a first readable state including digital indicia and at least start and stop code indicia and at least a second readable state wherein at least one of the start and stop code indicia which appear in the first readable state form part of the digital indicia in the second readable state.

Preferably, the multiplicity of product unit specific indicators are each operative to provide machine-readable indications of exceedence of at least two thresholds by at least one product quality determining parameter.

In another preferred embodiment the machine-readable indications each include a variable bar code having at least three readable states including a first readable state including digital indicia and at least start and stop code indicia, and at least a second readable state wherein at least one of the start and stop code indicia which appear in the first readable state form part of the digital indicia in the second readable state.

There is also provided in accordance with another preferred embodiment of the present invention a product unit specific indicator operative to provide a machine-readable indication of exceedence of at least one threshold by at least one product quality determining parameter, the indicator including a variable bar code having a first readable state including digital indicia and at least start and stop code indicia and at least a second readable state wherein at least one of the start and stop code indicia which appear in the first readable state form part of the digital indicia in the second readable state.

There is further provided in accordance with yet another preferred embodiment of the present invention a product unit specific indicator operative to provide a machine-readable indication of exceedence of at least one threshold by at least one product quality determining parameter, the indicator including a variable bar code having a fixed bar code portion and at least one selectably appearing bar code portion, both the fixed bar code portion and the at least one selectably appearing bar code portion being readable by a bar code reader.

There is even further provided in accordance with still another preferred embodiment of the present invention a product unit specific indicator operative to provide a machine-readable indication of exceedence of at least one threshold by at least one product quality determining parameter, the indicator including a variable bar code having a fixed bar code portion representing a first number of digits and at least one selectably appearing bar code portion which appears alongside the fixed bar code portion, the at least one selectably appearing bar code portion representing at least one additional digit.

Preferably, the at least one selectably appearing bar code portion appears alongside the fixed bar code portion in response to exceedence of the at least one threshold. Alternatively, the at least one selectably appearing bar code portion disappears in response to exceedence of the at least one threshold.

There is also provided in accordance with another preferred embodiment of the present invention an event indicator operative to provide a machine-readable indication of occurrence of at least one event, the indicator including a variable bar code having a first readable state including digital indicia and at least start and stop code indicia and at least a second readable state wherein at least one of the start and stop code indicia which appear in the first readable state form part of the digital indicia in the second readable state.

There is still further provided in accordance with yet another preferred embodiment of the present invention an event indicator operative to provide a machine-readable indication of occurrence of at least one event, the indicator including a variable bar code having a fixed bar code portion and at least one selectably appearing bar code portion, both the fixed bar code portion and the at least one selectably appearing bar code portion being readable by a bar code reader.

There is even further provided in accordance with still another preferred embodiment of the present invention an event indicator operative to provide a machine-readable indication of occurrence of at least one event, the indicator including a variable bar code having a fixed bar code portion representing a first number of digits and at least one selectably appearing bar code portion which appears alongside the fixed bar code portion, the at least one selectably appearing bar code portion representing at least one additional digit.

There is also provided in accordance with yet another preferred embodiment of the present invention a method for quality management for products including employing a multiplicity of product unit specific indicators each to provide a machine-readable indication of exceedance of at least one threshold by at least one product quality determining parameter; reading the product unit specific indicators and providing output indications therefrom and interpreting the output indications to provide human sensible, product unit specific, product quality status outputs.

There is further provided in accordance with even a further preferred embodiment of the present invention a method for providing a machine-readable indication of exceedance of at least one threshold by at least one product quality determining parameter including employing an indicator which provides a variable bar code having a first readable state including digital indicia and at least start and stop code indicia and at least a second readable state wherein at least one of the start and stop code indicia which appear in the first readable state form part of the digital indicia in the second readable state.

There is also provided in accordance with still another preferred embodiment of the present invention a method for providing a machine-readable indication of exceedance of at least one threshold by at least one product quality determining parameter including employing an indicator which provides a variable bar code having a fixed bar code portion and at least one selectably appearing bar code portion and reading both the fixed bar code portion and the at least one selectably appearing bar code portion using a bar code reader.

There is further provided in accordance with yet another preferred embodiment of the present invention a method for providing a machine-readable indication of exceedance of at least one threshold by at least one product quality determining parameter including employing an indicator which provides a variable bar code having a fixed bar code portion representing a first number of digits and at least one selectably appearing bar code portion which appears alongside the fixed bar code portion, the at least one selectably appearing bar code portion representing at least one additional digit.

BRIEF DESCRIPTION OF THE DRAWINGS

The present invention will be understood and appreciated more fully from the following detailed description, taken in conjunction with the drawings in which:

FIGS. 1A, 1B, 1C and 1D together are a simplified illustration of a system and methodology for quality management constructed and operative in accordance with a preferred embodiment of the present invention;

FIG. 2D is a simplified illustration of a quality indicator constructed and operative in accordance with yet another preferred embodiment of the present invention for indicating pH history;

FIG. 2E is a simplified illustration of a quality indicator constructed and operative in accordance with still another preferred embodiment of the present invention for indicating humidity history;

FIG. 2F is a simplified illustration of a quality indicator constructed and operative in accordance with a further preferred embodiment of the present invention for indicating impact history;

FIG. 3A is a simplified illustration of a quality indicator constructed and operative in accordance with a preferred embodiment of the present invention for indicating elapsed time and temperature history;

FIG. 4C is a simplified illustration of the structure and operation of an example of the indicator of FIG. 2C, in accordance with a preferred embodiment of the present invention;

FIG. 4F is a simplified illustration of the structure and operation of an example of the indicator of FIG. 2F, in accordance with a preferred embodiment of the present invention;

FIG. 5B is a simplified illustration of the structure and operation of an example of the indicator of FIG. 3B in accordance with a preferred embodiment of the present invention;

FIG. 7B is a simplified illustration of the structure and operation of a quality management system constructed and operative in accordance with a preferred embodiment of the present invention in the context of a supermarket.

DETAILED DESCRIPTION OF PREFERRED EMBODIMENTS

Figure 1B:
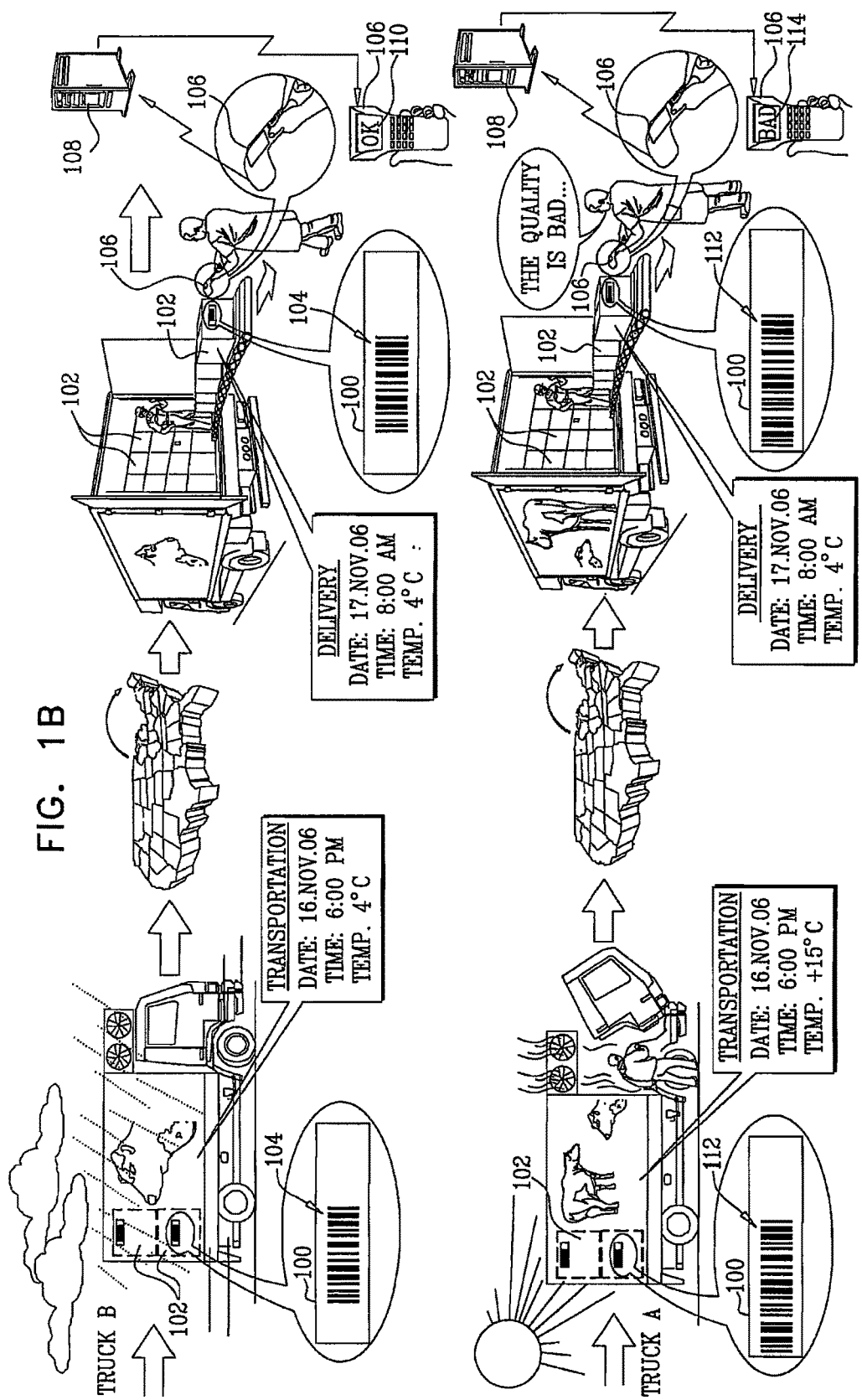

Reference is now made to FIGS. 1A, 1B, 1C and 1D, which together are a simplified illustration of a system and methodology for quality management constructed and operative in accordance with a preferred embodiment of the present invention. As seen in FIGS. 1A-1D, there is shown a quality management system and methodology for products including a multiplicity of product unit specific indicators, here shown in the form of changeable barcode indicators, each operative to provide a machine-readable indication of exceedence of at least one threshold by at least one product quality determining parameter, at least one indicator reader operative to read the product unit specific indicators and to provide output indications and a product type specific indication interpreter operative to receive the output indications and to provide human sensible, product unit specific, product quality status outputs.

The changeable barcode indicator may incorporate a product code such as a UPC code.

Preferably, the product unit specific indicator is operative to provide a machine-readable indication of exceedence of at least one threshold by at least one product quality determining parameter and in a preferred embodiment provides a variable bar code having a first readable state including digital indicia and at least start and stop code indicia and at least a second readable state wherein at least one of the start and stop code indicia which appear in the first readable state form part of the digital indicia in the second readable state.

Additionally or alternatively, the indicator provides a variable bar code having a fixed bar code portion and at least one selectably appearing bar code portion, both the fixed bar code portion and the at least one selectably appearing bar code portion being readable by a conventional bar code reader.

Additionally or alternatively, the indicator provides a variable bar code having a fixed bar code portion representing a first number of digits and at least one selectably appearing bar code portion which appears alongside the fixed bar code portion, the at least one selectably appearing bar code portion representing at least one additional digit.

Turning now to FIGS. 1A-1D, the present invention is illustrated in the context of a typical application, here a meat processing plant. A product unit specific indicator 100 is attached to or otherwise incorporated into each package 102 of processed meat. A package bearing a product unit specific indicator 100 may be an individual package suitable for retail sale and/or a carton containing a plurality of such individual packages. In the illustrated embodiment, packages 102 include both alternatives.

It is also a possibility that different types of indicators 100 may be employed for different types of packages. For example, the indicator used on a carton containing a plurality of individual packages may be more or less accurate or have a greater or lesser dynamic range of indications than the indictor used on an individual package. For example, the indicator on a carton may include an indicator capable of indicating exceedance of additional thresholds, not included on the indicators of individual packages contained therein, or fewer thresholds than the indicators of individual packages contained therein.

In accordance with a preferred embodiment of the present invention, the indicators 100 may be assembled and/or actuated at the same location or at a location adjacent that at which the indicators 100 are associated with packages 102. A suitable indicator assembler/actuator is indicated by reference numeral 103.

In the illustrated embodiment, the indicator includes a 2 of 5 interleaved bar code. The indicator is typically calibrated to remain in a first readable state as long as it remains at a temperature less than or equal to 4 degrees Celsius and not more than a predetermined time period, typically one week, has elapsed since manufacture or other actuation of the indicator. This first readable state is indicated by reference numeral 104. It is seen that so long as the temperature of the package 102 does not exceed 4 degrees Celsius and one week has not elapsed since manufacture or other actuation of the indicator, the indicator 100 remains in the first readable state 104. At any stage, such as upon delivery to the customer, the indicator 100 can be read with a conventional bar code reader 106, which preferably communicates with a remote quality indication server 108 and provides an immediate indication of a quality parameter, such as an OK indication 110, to an inspector.

If and when the temperature of the package 102 exceeds 4 degrees Celsius, such as when it reaches 15 degrees Celsius, the indicator assumes a second readable state, indicated by reference numeral 112. This second readable state does not change notwithstanding that the temperature of the package 102 subsequently returns to an acceptable temperature, such as 4 degrees Celsius. Accordingly, upon inspection, as upon delivery to the customer, upon reading the indicator 100 by an inspector using a conventional bar code reader 106, the bar code in its second readable state 112 preferably provides information to the quality indication server 108 which enables the server to provide an immediate indication of a quality parameter, such as a BAD indication 114. This BAD indication 114 indicates that at some time in the history of the indicator 100, the package 102 to which it was attached was at a temperature exceeding 4 degrees Celsius and that this event has rendered the specific product in package 102 unacceptable for sale.

It is appreciated that whereas machine reading of the indicator 100 provides an indication of whether or not a given event has occurred, the indication of a quality parameter by quality indication server 108 provides an indication of whether and to what extent that event has affected the quality of a given product with which the indicator 100 is associated. It is appreciated that there may be a great variation in the effect of a given event depending on the type of product. Thus, for example, exposure to 15 degrees Celsius may cause fresh meat to be rendered unfit for sale but may not appreciably affect the quality or saleability of oranges.

Figure 1C:
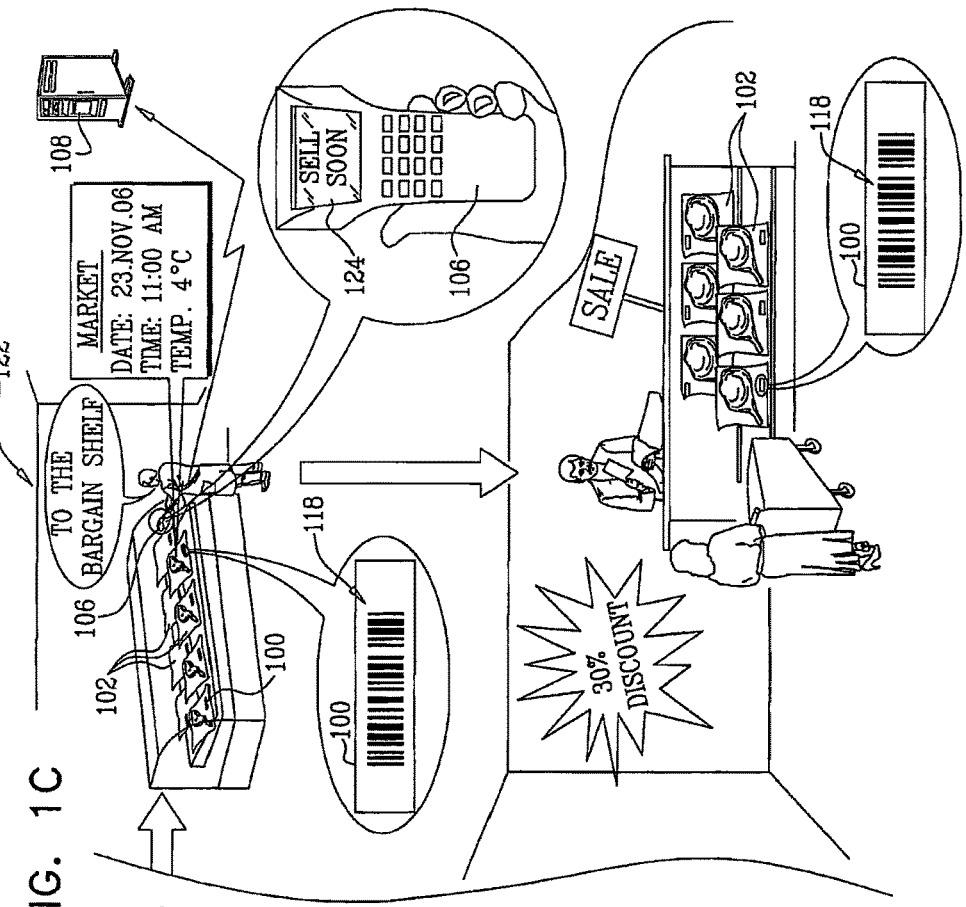
Figure 1C:
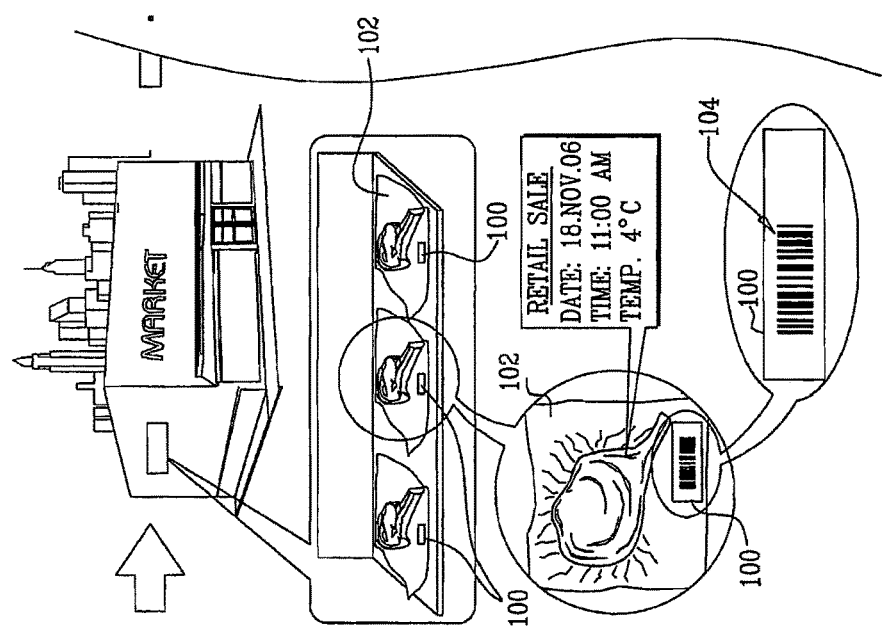

Turning now specifically to FIGS. 1C and 1D, it is seen that indicator 100 may additionally and independently serve to indicate elapsed time. Thus, upon exceedance of the predetermined time period following manufacture or other actuation of the indicator 100, the indicator 100 assumes a third readable state 118 which indicates that a predetermined amount of time has elapsed. Upon elapse of a further predetermined amount of time, typically a second week, the indicator 100 may assume a fourth readable state 120.

Accordingly, upon inspection, as indicated by reference numeral 122, as upon periodic stock inspection at a retail site, upon reading the indicator 100 by an inspector using a conventional bar code reader 106, the bar code in its third readable state 118 provides information to the quality indication server 108 which enables the server to provide an immediate indication of a quality parameter, such as a SELL SOON indication 124. This SELL SOON indication 124 indicates that, since the predetermined time interval has elapsed, the package 102 to which it was attached should be positioned and/or priced for immediate sale.

Turning now to FIG. 1D, it is seen that upon further inspection, as indicated by reference numeral 132, as upon periodic stock inspection at the retail site, upon reading the indicator 100 by an inspector using a conventional bar code reader 106, the bar code in its fourth readable state 120 provides information to the quality indication server 108 which enables the server to provide an immediate indication of a quality parameter, such as an EXPIRED indication 134. This EXPIRED indication 134 indicates that the package 102 to which it was attached should be discarded, since the further predetermined time period has elapsed.

Additionally or alternatively, the further inspection may take place automatically at the checkout, where the indicator 100 is read by a checkout scanner 136. In such a case, the bar code in its fourth readable state 120 provides information to the quality indication server 108 which enables the server to provide an immediate indication of a quality parameter, such as a DO NOT SELL indication 138, to the checkout clerk. This DO NOT SELL indication 138 indicates that the package 102 to which it was attached may not be sold since the further predetermined time period has elapsed. It is appreciated that the DO NOT SELL indication functionality described above provides a high level of control in implementing package-specific shelf-life restrictions and thus, by eliminating uncertainty regarding the shelf life of a given product, may enable packaged products which have been maintained under optimal conditions to have longer shelf lives than would otherwise be possible.

Reference is now made to FIGS. 2A-2G, which are simplified illustrations of event indicators constructed and operative in accordance with a preferred embodiment of the present invention, respectively, for indicating temperature history, elapsed time and temperature history, pH history, humidity history, impact history and orientation history.

Figure 2A:
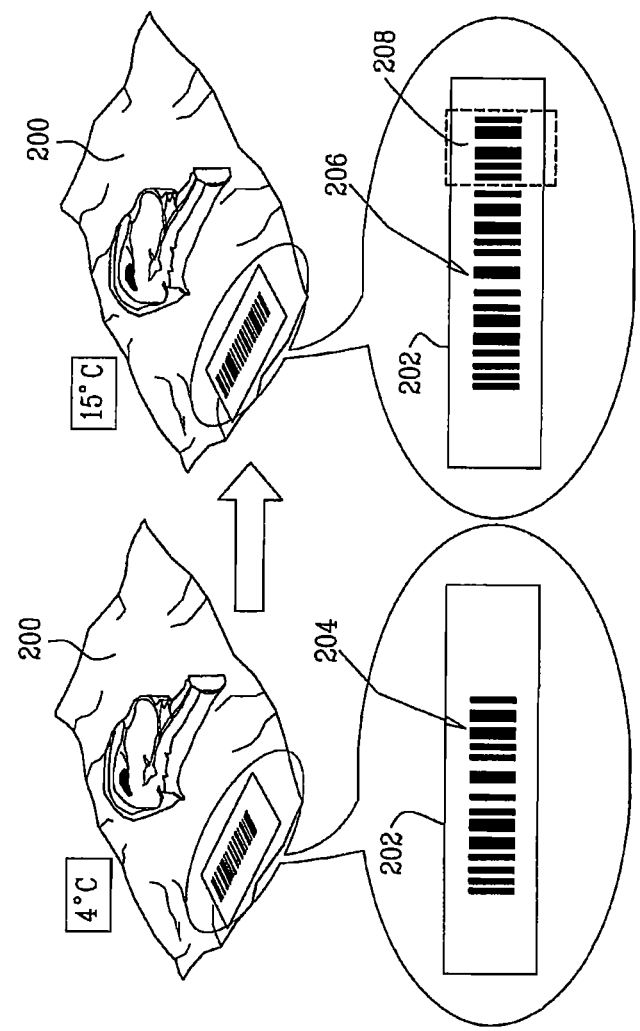
FIG. 2A is a simplified illustration of a quality indicator constructed and operative in accordance with a preferred embodiment of the present invention for indicating temperature history.

FIG. 2A illustrates a package of meat 200 including a temperature event indicator 202 constructed and operative in accordance with a preferred embodiment of the present invention. As illustrated in FIG. 2A, indicator 202 includes a bar code which is in a first readable state 204, typically 0123, when the temperature of the package 200 is less than 5 degrees Celsius and is in a second readable state 206, typically 012312, including an additional portion 208, when the temperature of the package 200 is more than 5 degrees Celsius, such as 15 degrees Celsius. In the illustrated embodiment once the second readable state 206 is reached, the indicator preferably does not thereafter revert to the first readable state 204 notwithstanding that the temperature of the package 200 subsequently returns to 4 degrees Celsius.

Figure 2B:
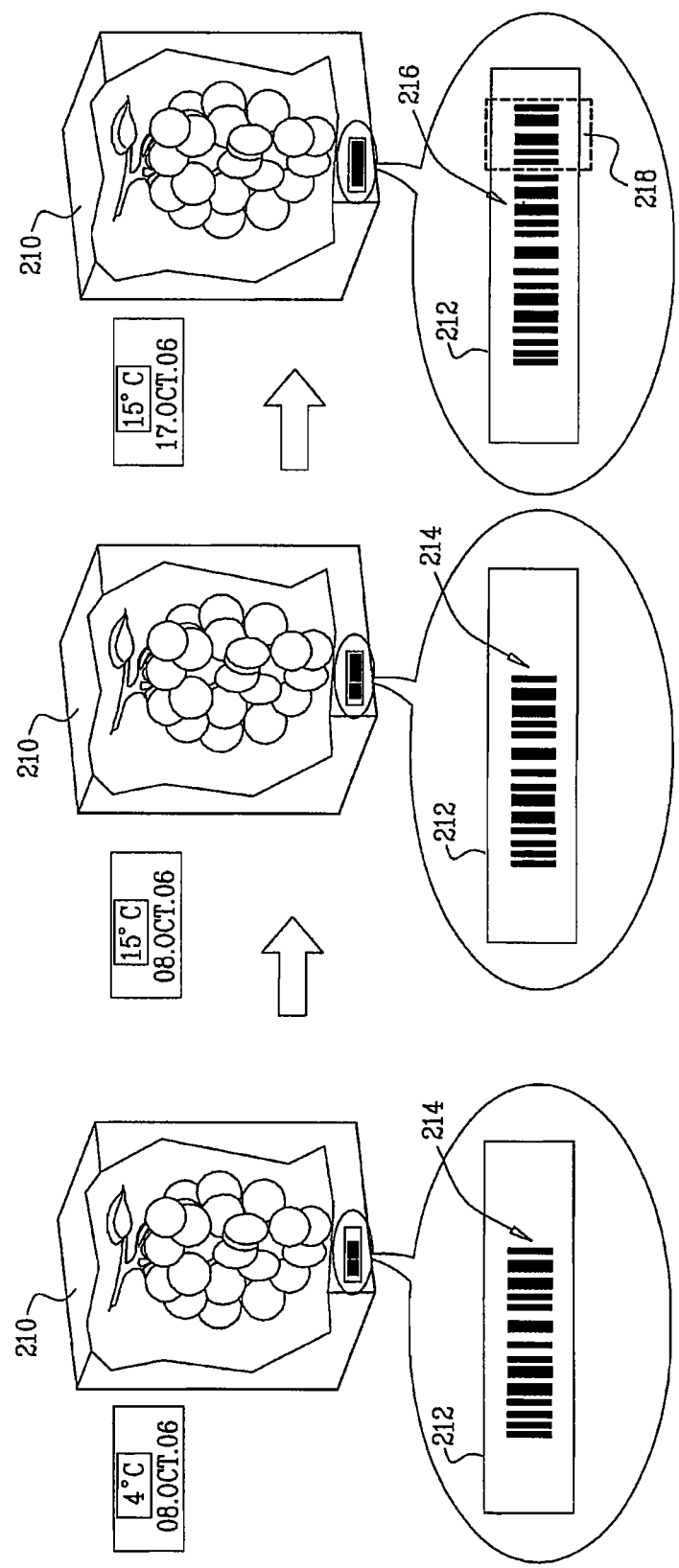
FIG. 2B is a simplified illustration of a quality indicator constructed and operative in accordance with another preferred embodiment of the present invention for indicating elapsed time and temperature history.

FIG. 2B illustrates a package of grapes 210 including a combination elapsed time and temperature indicator 212 constructed and operative in accordance with a preferred embodiment of the present invention. As illustrated in FIG. 2B, indicator 212 includes a bar code which is in a first readable state 214, typically 0123, when the temperature of the package 210 has not exceeded 4 degrees Celsius for a cumulative period of more than 48 hours and is in a second readable state 216, typically 012312, including an additional portion 218, when the temperature of the package 210 has been more than 4 degrees Celsius, such as 15 degrees Celsius, for at least a cumulative period of 48 hours. In the illustrated embodiment once the second readable state 216 is reached, the indicator does not revert to the first readable state 214 notwithstanding that the temperature of the package 210 subsequently returns to 4 degrees Celsius.

Figure 2C:
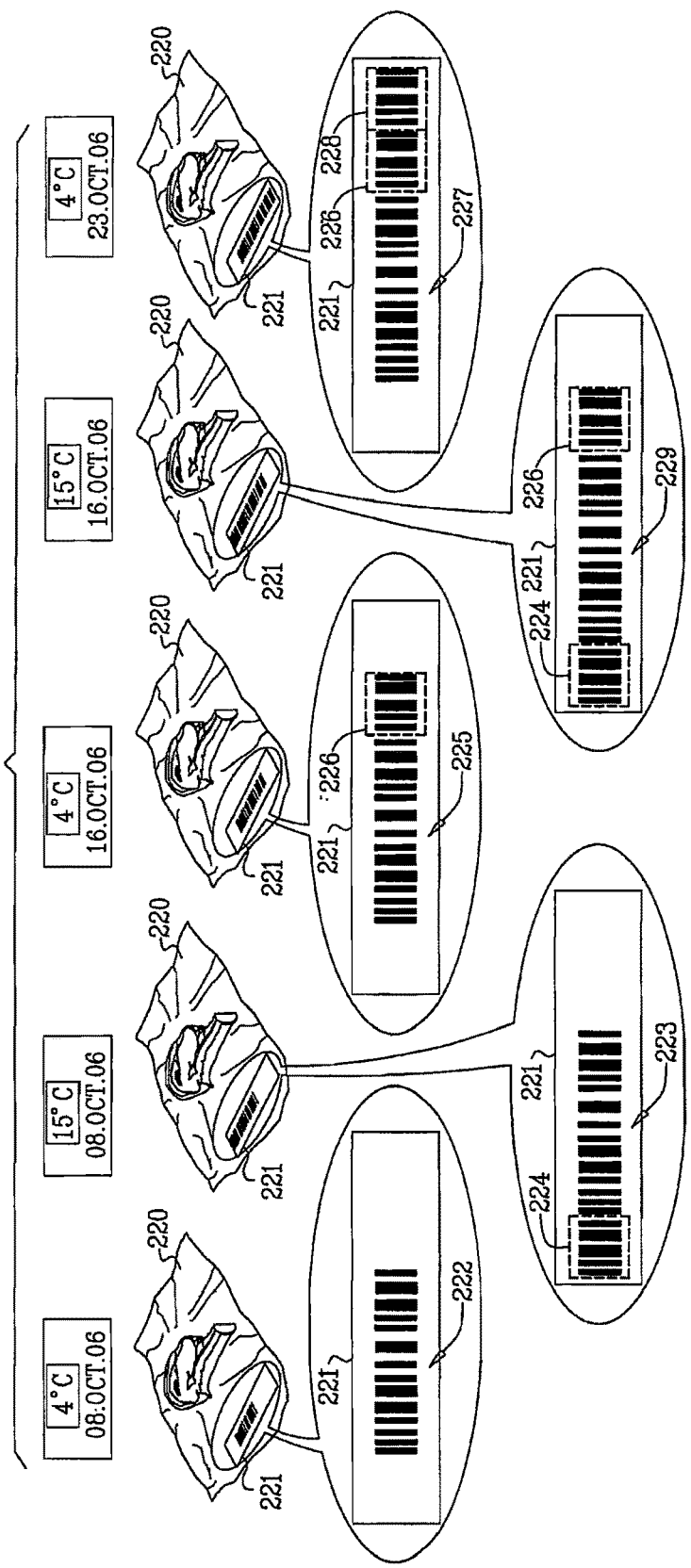
FIG. 2C is a simplified illustration of a quality indicator constructed and operative in accordance with another preferred embodiment of the present invention for separately indicating elapsed time and temperature history.

FIG. 2C illustrates a package of meat 220 including an indicator 221 for separately indicating elapsed time and temperature, constructed and operative in accordance with a preferred embodiment of the present invention. As illustrated in FIG. 2C, indicator 221 includes a bar code which is in a first readable state 222, typically 0123, when the temperature of the package 220 has not exceeded a temperature threshold, typically 4 degrees Celsius, and no more than a first predetermined time period, typically one week, has elapsed since packaging. The indicator 221 shifts to a second readable state 223, typically 350123, including a first additional portion 224, when the temperature of the package 220 exceeds the temperature threshold, such as 15 degrees Celsius, and no more than the first predetermined time period has elapsed since packaging. The indicator 221 shifts to a third readable state 225, typically 012312, including a second additional portion 226, when the first predetermined time period has elapsed since packaging but the temperature of the package 220 has not exceeded the temperature threshold and shifts to a fourth readable state 227, typically 01231212, including second additional portion 226 and a third additional portion 228, when a second predetermined time period, typically two weeks, has elapsed since packaging, if the temperature has not exceeded the temperature threshold. If the temperature of package 220 has exceeded the temperature threshold and the first predetermined time period has elapsed since packaging, the indicator shifts to a fifth readable state 229, typically 35012312, including first additional portion 224 and second additional portion 226.

FIG. 2D illustrates a container of milk 230 including a pH event indicator 232 constructed and operative in accordance with a preferred embodiment of the present invention. As illustrated in FIG. 2D, indicator 232 includes a bar code which is in a first readable state 234, typically 0123, when the pH of the milk is more than 5 and is in a second readable state 236, typically 012312, including a first additional portion 237, when the pH of the milk is between 4 and 5. When the pH of the milk reaches a lower level, such as 4 or below, the indicator 232 reaches a third readable state 238, typically 01231212, including first additional portion 237 and a second additional portion 239.

FIG. 2E illustrates a container of cereal 240 including a humidity event indicator 242 constructed and operative in accordance with a preferred embodiment of the present invention. As illustrated in FIG. 2E, indicator 242 includes a bar code which is in a first readable state 244, typically 0123, when the relative humidity of the cereal does not exceed a predetermined humidity threshold, typically 15%, and is in a second readable state 246, typically 012312, including an additional portion 248, when the relative humidity of the cereal is greater than the predetermined humidity threshold, such as 60%.

FIG. 2F illustrates a packaged impact sensitive product 250, such as a computer, including an impact event indicator 252 constructed and operative in accordance with a preferred embodiment of the present invention. As illustrated in FIG. 2F, indicator 252 includes a bar code which is in a first readable state 254, typically 0123, when no impact exceeding an impact threshold, typically 10 G, has occurred and is in a second readable state 256, typically 012312, including an additional portion 258, when an impact exceeding the impact threshold has occurred.

Figure 2G:
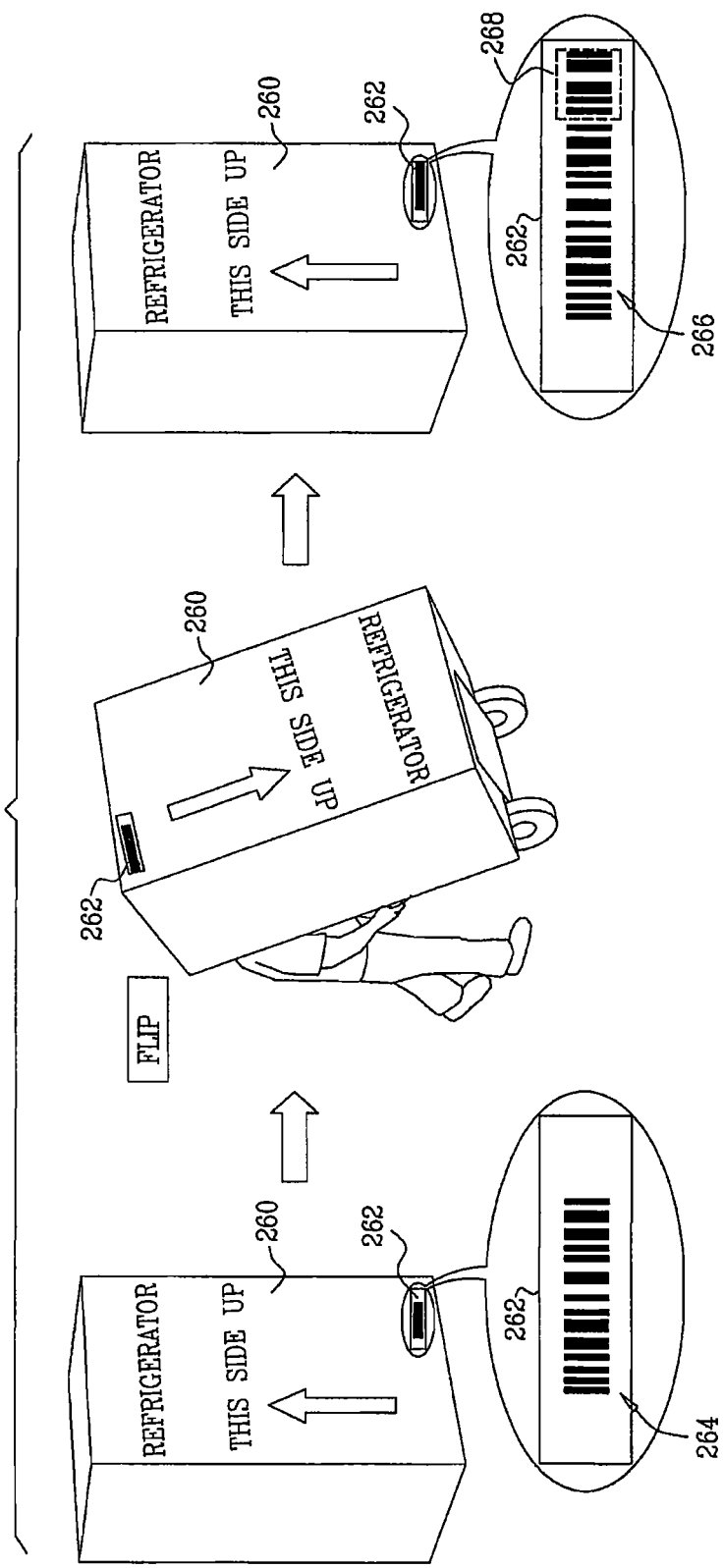
FIG. 2G is a simplified illustration of a quality indicator constructed and operative in accordance with a still further preferred embodiment of the present invention for indicating orientation history.

FIG. 2G illustrates a packaged orientation sensitive product 260, such as a refrigerator, including an orientation event indicator 262 constructed and operative in accordance with a preferred embodiment of the present invention. As illustrated in FIG. 2G, indicator 262 includes a bar code which is in a first readable state 264, typically 0123, when the product has not changed its angular orientation by more than 170 degrees from its original upright orientation and is in a second readable state 266, typically 012312, including an additional portion 268, when a change of orientation of more than 170 degrees has occurred, even if subsequently the product 260 has been returned to its original upright orientation.

It is appreciated that the present invention also encompasses indicators wherein the first readable state has more digits than the second readable state and similarly where each subsequent readable state has fewer digits than the preceding readable state. This may readily be achieved in accordance with the present invention, for example, by initially locating a black background behind transparent areas, similar to the transparent areas described hereinbelow with reference to FIGS. 4A-5C, and then, as the result of a change in an environmental parameter, changing that black background to white. Alternatively, this may be achieved by employing white on black background bar codes instead of black on white background bar codes as shown in the examples above.

Reference is now made to FIG. 3A, which is a simplified illustration of a package of meat 300 including an indicator 302 for separately indicating elapsed time and temperature, constructed and operative in accordance with a preferred embodiment of the present invention. The indicator 302 of FIG. 3A is a two-dimensional indicator which includes a plurality of fixed cells 303 and a plurality of variable cells 304, each of which is capable of providing a machine-readable indication of an event. It is appreciated that at a basic level, the indicator 302 of FIG. 3A provides similar information to the indicator 221 of FIG. 2C. However, due to the fact that indicator 302 contains a plurality of variable cells 304, it may readily be employed to indicate a plurality of temperature levels or extents of elapsed time.

As seen in FIG. 3A, indicator 302 includes at least a first variable area 305, typically including 3 variable cells 304, which is in a first readable state, such as a white state 306, when the temperature of the package 220 has not exceeded a temperature threshold, typically 4 degrees Celsius. The at least first variable area 305 shifts to a second readable state, such as a black state 308, when the temperature of the package 300 exceeds the temperature threshold, such as 15 degrees Celsius. An at least second variable area 309, typically including 4 variable cells 304, is in a first readable state, such as a white state 310, prior to elapse of a first predetermined time period, such as one week, since packaging and shifts to a second readable state, such as a black state 312, once the first predetermined time period has elapsed since packaging.

An at least third variable area 313, typically including 2 variable cells 304, is in a first readable state, such as a white state 314, prior to elapse of a second predetermined time period, greater than the first predetermined time period, such as two weeks, since packaging and shifts to a second readable state, such as a black state 316, once the second predetermined time period has elapsed since packaging.

Thus, it may be appreciated that when package 300 is in the state designated by the letter A, the first, second and third variable areas 305, 309 and 313 are all in their first readable state, indicating that the temperature of the package has not exceeded the temperature threshold and the elapsed time since packaging has not exceeded the first predetermined time period.

When package 300 is in the state designated by the letter B, second and third variable areas 309 and 313 are both in their first readable state, while the first variable area 305 is in its second readable state indicating that the temperature of the package has exceeded the temperature threshold and the elapsed time since packaging has not exceeded the first predetermined time period.

When package 300 is in the state designated by the letter C, the first and third variable areas 305 and 313 are in their first readable state, while the second variable area 309 is in its second readable state, indicating that the temperature of the package has not exceeded the temperature threshold and the elapsed time since packaging has exceeded the first predetermined time period but not the second predetermined time period.

When package 300 is in the state designated by the letter D, the first, second and third variable areas 305, 309 and 313 are all in their second readable state, indicating that the temperature of the package has exceeded the temperature threshold and the elapsed time since packaging has exceeded the first and second predetermined time periods.

When package 300 is in the state designated by the letter E, the first variable area 305 is in its first readable state, while the second and third variable areas 309 and 313 are in their second readable state, indicating that the temperature of the package has not exceeded the temperature threshold and the elapsed time since packaging has exceeded the first and second predetermined time periods.

Figure 3B:
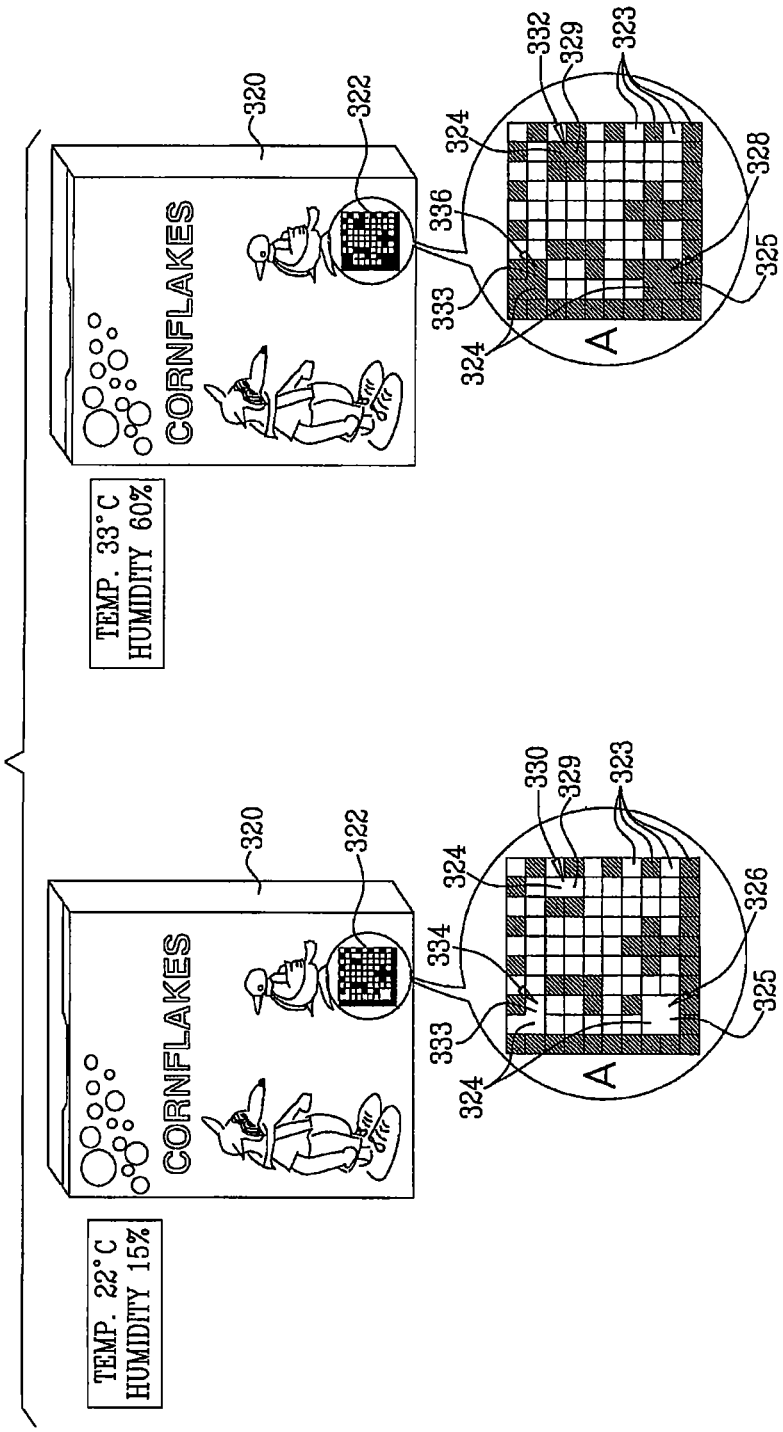
FIG. 3B is a simplified illustration of a quality indicator constructed and operative in accordance with another preferred embodiment of the present invention for indicating temperature and humidity history.

Reference is now made to FIG. 3B, which is a simplified illustration of a package of cereal 320 including an indicator 322 for separately indicating humidity and temperature, constructed and operative in accordance with a preferred embodiment of the present invention. The indicator 322 of FIG. 3B is a two-dimensional indicator which includes a plurality of fixed cells 323 and a plurality of variable cells 324, each of which is capable of providing a machine-readable indication of an event. Due to the fact that indicator 322 contains a plurality of variable cells 324, it may readily be employed to indicate a plurality of temperature levels and humidity levels.

As seen in FIG. 3B, indicator 322 includes at least a first variable area 325, typically including 4 variable cells 324, which is in a first readable state, such as a white state 326, when the humidity of the package 320 is less than a humidity threshold, such as 30%. The at least first variable area 325 shifts to a second readable state, such as a black state 328, when the humidity of package 320 exceeds the humidity threshold, such as 60%. It is appreciated that depending on the construction of the indicator, the humidity that is indicated by first variable area 325 is either the ambient relative humidity or alternatively the humidity of the contents of the package.

An at least second variable area 329, typically including 2 variable cells 324, is in a first readable state, such as a white state 330, when the temperature of the package 320 has not exceeded a temperature threshold, such as 25 degrees Celsius, and shifts to a second readable state, such as a black state 332, if temperature of the package 320 exceeds the temperature threshold, such as 33 degrees Celsius. An at least third variable area 333, typically including 3 variable cells 324, is also in a first readable state, such as a white state 334, when the temperature of the package 320 has not exceeded the temperature threshold, and also shifts to a second readable state, such as a black state 336, when the temperature of the package 320 exceeds the temperature threshold.

Thus, it may be appreciated that when package 320 is in the state designated by the letter A, the first, second and third variable areas 325, 329 and 333 are all in their first readable state, indicating that the temperature of the package has not exceeded the temperature threshold and the humidity has not exceeded the humidity threshold.

When package 300 is in the state designated by the letter B, first, second and third variable areas 325, 329 and 333 are all in their second readable state, indicating that the temperature of the package has exceeded the temperature threshold and the humidity has exceeded the humidity threshold.

It is appreciated that in the illustrated embodiment of FIG. 3B variable areas 329 and 333 provide identical temperature information. It is appreciated that multiple variable areas may alternatively be used to indicate multiple temperature levels, similar to the indicator illustrated in FIG. 3C.

Figure 3C:
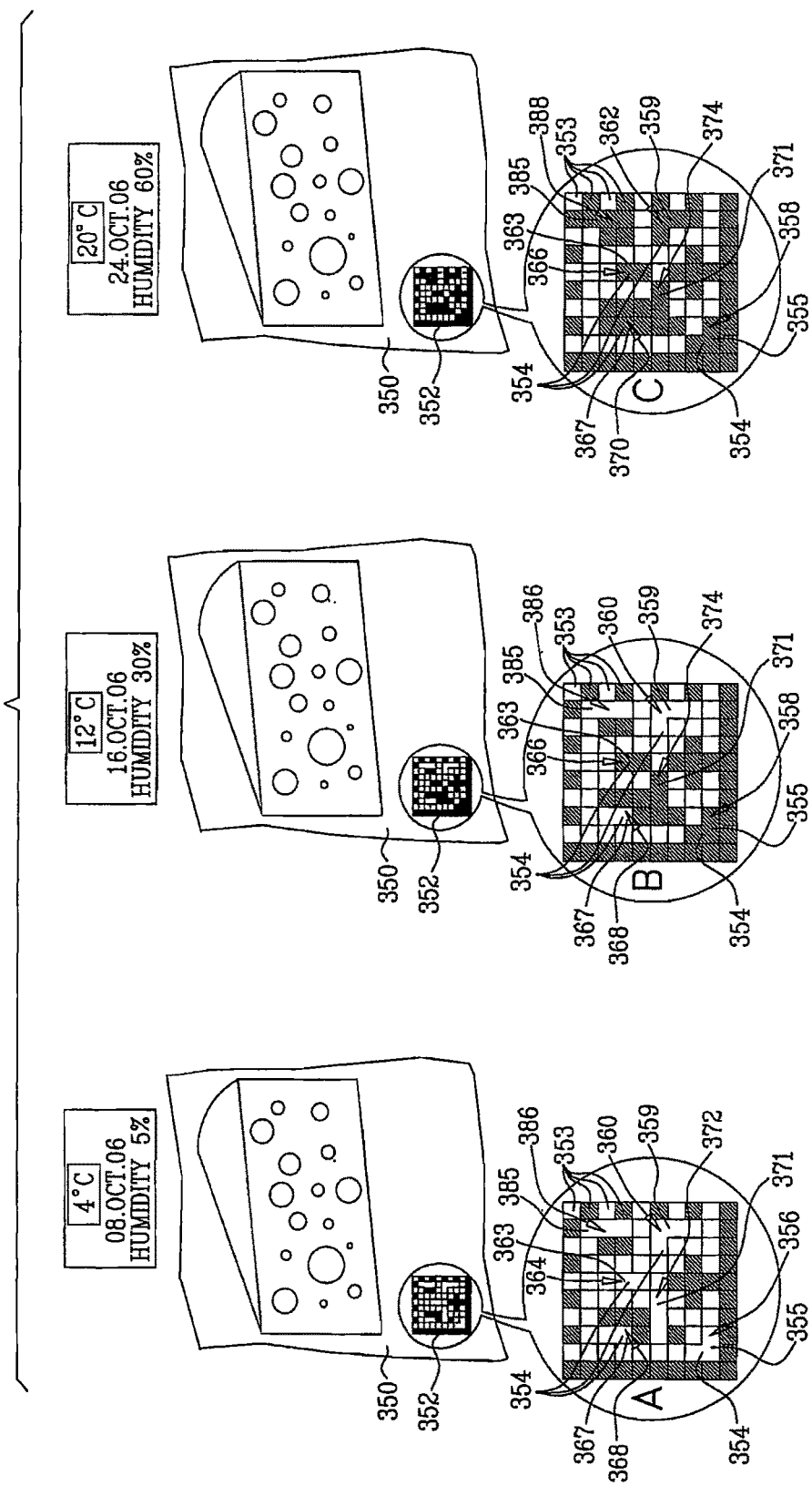
FIG. 3C is a simplified illustration of a quality indicator constructed and operative in accordance with another preferred embodiment of the present invention for indicating elapsed time, temperature and humidity history.

Reference is now made to FIG. 3C, which is a simplified illustration of a package of cheese 350 including an indicator 352 for separately indicating elapsed time, humidity and temperature, constructed and operative in accordance with a preferred embodiment of the present invention. The indicator 352 of FIG. 3C is a two-dimensional indicator which includes a plurality of fixed cells 353 and a plurality of variable cells 354, each of which is capable of providing a machine-readable indication of an event. Due to the fact that indicator 352 contains a plurality of variable cells 354, it may readily be employed to indicate a plurality of temperature levels, extents of elapsed time and humidity levels.

As seen in FIG. 3C, indicator 352 includes at least a first variable area 355, typically including 3 variable cells 354, which is in a first readable state, such as a white state 356, prior to elapse of a first time period, typically one week, since packaging and shifts to a second state, such as a black state 358, once the first time period has elapsed since packaging. An at least second variable area 359, typically including 4 variable cells 354, is in a first state, such as a white state 360, prior to elapse of a second time period, greater than the first time period, typically two weeks, since packaging and shifts to a second state, such as a black state 362, once the second time period has elapsed since packaging.

An at least third variable area 363, typically including 2 variable cells 354, is in a first readable state, such as white state 364, when the humidity is less than a first humidity threshold, typically 10%, and shifts to a second state, such as a black state 366, if the humidity exceeds the first humidity threshold, such as 30%. An at least fourth variable area 367, typically including 2 variable cells 354, is in a first state, such as a white state 368, when the humidity is less than a second humidity threshold, greater than the first humidity threshold, typically 40%, and shifts to a second state, such as a black state 370, if the humidity exceeds the second humidity threshold, such as 60%.

An at least fifth variable area 371, typically including 3 variable cells 354, is in a first state, such as white state 372, when the temperature of the package 350 has not exceeded a first temperature threshold, typically 5 degrees Celsius. The at least first variable area 355 shifts to a second readable state, such as a black state 374, when the temperature of the package 350 exceeds the first temperature threshold, such as 12 degrees Celsius. An at least sixth variable area 385, typically including 3 variable cells 354, is in a first readable state, such as white state 386, when the temperature of the package 350 has not exceeded a second temperature threshold, greater than the first temperature threshold, typically 12 degrees Celsius. The at least second variable area 385 shifts to a second readable state, such as a black state 388, when the temperature of the package 350 exceeds the second temperature threshold, such as 20 degrees Celsius.

It is appreciated that depending on the construction of the indicator, the humidity that is indicated by variable areas 363 and 367 is the ambient relative humidity or alternatively the humidity of the contents of the package.

Thus it may be appreciated that when package 350 is in the state designated by the letter A, the first to sixth variable areas 355, 359, 363, 367, 371 and 385 are all in their first readable state, indicating that less than the first time period has elapsed since packaging, the humidity has not exceeded the first humidity threshold and the temperature of the package has not exceeded the first temperature threshold.

When package 350 is in the state designated by the letter B, first, third and fifth variable areas 355, 363 and 371 are all in their second state, and second, fourth and sixth variable areas 359, 367 and 385 are all in their first state, indicating that the time duration from packaging has exceeded the first time period but has not exceeded the second time period, the humidity has exceeded the first humidity threshold but has not exceeded the second humidity threshold and the temperature of the package has exceeded the first temperature threshold but has not exceeded the second temperature threshold.

When package 350 is in the state designated by the letter C, the first to sixth variable areas 355, 359, 363, 367, 371 and 385 are all in their second state, indicating that the time duration from packaging has exceeded the first and second time periods, the humidity has exceeded the first and second humidity thresholds and the temperature of the package has exceeded the first and second temperature thresholds.

It is appreciated that while the illustrated embodiments of FIGS. 3A-3C include variable areas including multiple variable cells, each of the variable areas may include a single variable cell or multiple variable cells. Typically, variable areas include multiple variable cells to enhance readability of the variable areas.

Figure 4A:
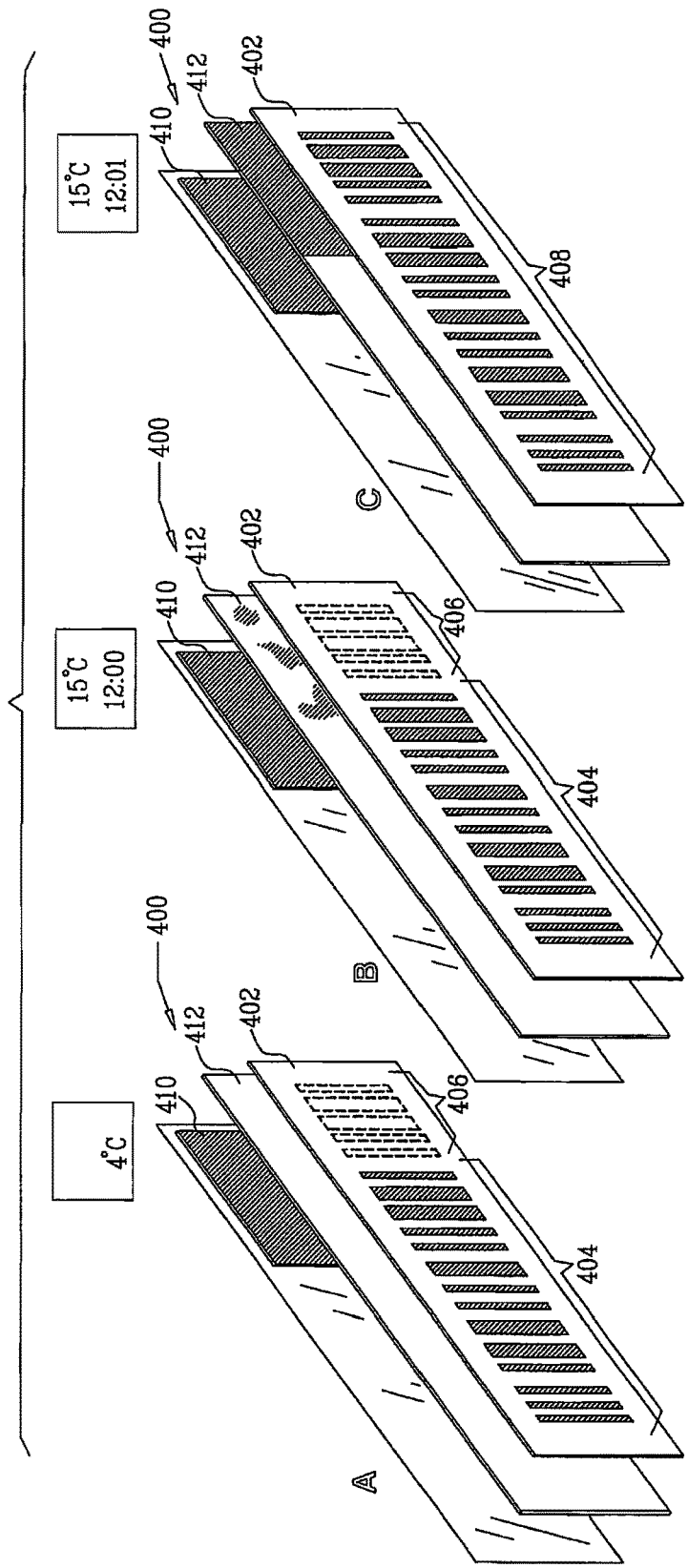
FIG. 4A is a simplified illustration of the structure and operation of an example of the indicator of FIG. 2A, in accordance with a preferred embodiment of the present invention.

Reference is now made to FIG. 4A, which is a simplified illustration of the construction and operation of one embodiment of the indicator 202 of FIG. 2A for indicating temperature history. As seen in FIG. 4A, the indicator, here designated by reference numeral 400, preferably includes a bar code defining layer 402, which is preferably printed on a transparent substrate. The printing on the transparent substrate preferably defines a bar code in a first readable state 404 and alongside it a plurality of transparent areas 406, which, if colored and read together with the bar code in the first readable state 404, provide a bar code in a second readable state 408. It is appreciated that the remainder of the bar code defining layer 402, other than the bar code in a first readable state 404 and the transparent areas 406, is preferably printed in a white color or a color defining high contrast with respect to the bar code in the first readable state 404.

Disposed behind transparent areas 406 there is preferably provided a temperature responsive coloring element 410, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 410 and bar code defining layer 402 is an opaque layer 412 of a color which defines high contrast with respect to the bar code in a first readable state 404.

When the indicator 400 is maintained at 4 degrees Celsius, the indicator is in the state designated by A in FIG. 4A.

When the temperature at the indicator rises above 4 degrees Celsius, the coloring agent on coloring element 410 begins to melt and be released from coloring element 410 and begins to diffuse through the opaque layer 412, as designated by B in FIG. 4A. Thus, when the temperature exceeds 4 degrees Celsius for at least a minimum time, such as one minute, the coloring agent rapidly diffuses through opaque layer 412, such that the portions of the opaque layer 412 which are readable through the transparent areas 406 appear similarly to the bar code in the first readable state 404 and can be read together therewith as a single bar code as in the state designated by C in FIG. 4A.

Figure 4B:
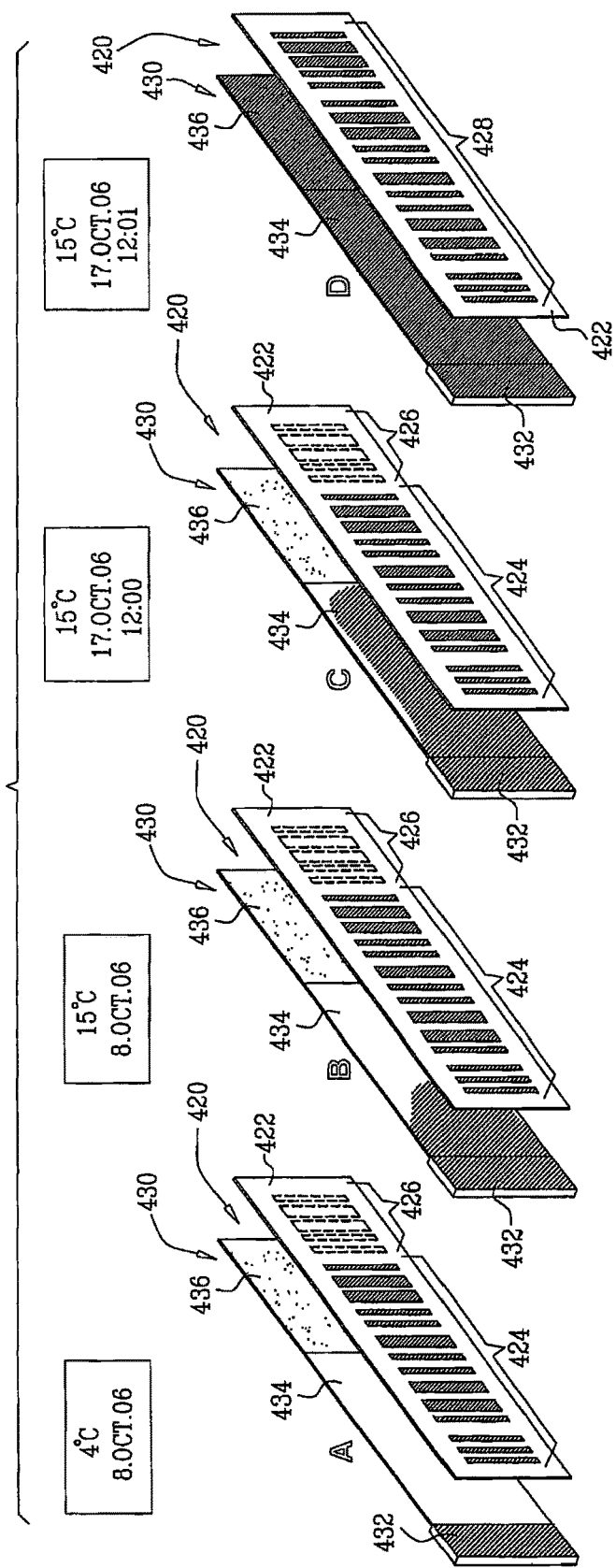
FIG. 4B is a simplified illustration of the structure and operation of an example of the indicator of FIG. 2B, in accordance with a preferred embodiment of the present invention.

Reference is now made to FIG. 4B, which is a simplified illustration of the construction and operation of one embodiment of the indicator 212 of FIG. 2B for indicating temperature/time history. As seen in FIG. 4B, the indicator, here designated by reference numeral 420, preferably includes a bar code defining layer 422, which is preferably printed on a transparent substrate. The printing on the transparent substrate preferably defines a bar code in a first readable state 424 and alongside it a plurality of transparent areas 426, which, if colored and read together with the bar code in the first readable state 424, provide a bar code in a second readable state 428. It is appreciated that the remainder of the bar code defining layer 422, other than the bar code in a first readable state 424 and the transparent areas 426, is preferably printed in a white color or a color defining high contrast with respect to the bar code in the first readable state 424.

Disposed behind bar code defining layer 422 is a temperature/time responsive coloring assembly 430, including a temperature responsive release coloring element 432, a relatively long-term coloring agent diffusion pathway defining element 434 and a relatively quick coloring agent diffusion region defining element 436. The temperature responsive release coloring element 432 preferably comprises a substrate, such as paper or a non-woven fabric impregnated with a coloring agent, such as Nigrosine, Alcohol soluble, a black color dye [CAS: 11099-03-9] (commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 434 preferably comprises a strip of paper, such as Grade 3 qualitative filter paper commercially available from Whatman plc of the UK, one end of which lies adjacent coloring element 432 and an opposite end of which extends to element 436. Relatively quick coloring agent diffusion region defining element 436 preferably comprises a strip of paper, such as Grade 4 qualitative filter paper commercially available from Whatman plc of the UK, which has a much higher speed of diffusion for the coloring agent than does element 434, thus ensuring that a time when the bar code is between its first and second readable states is minimized. It is appreciated that alternatively element 436 may be obviated and element 434 extends under all of transparent areas 426.

When the indicator 420 is maintained at 4 degrees Celsius, the indicator is in the state shown designated by A in FIG. 4B.

When the temperature at the indicator rises above 4 degrees Celsius, the coloring agent on coloring element 432 begins to melt and be released from coloring element 432 and begins to diffuse through the relatively long-term coloring agent diffusion pathway defining element 434, as designated by B in FIG. 4B. Thus, when the temperature exceeds 4 degrees Celsius for at least a minimum time, such as eight days, the coloring agent progresses towards the end of the pathway defined by the relatively long-term coloring agent diffusion pathway defining element 434, as designated by C in FIG. 4B. When the coloring agent reaches relatively quick coloring agent diffusion region defining element 436, it rapidly impregnates the portions of the element 436 which are readable through the transparent areas 426 so that they appear similarly to the bar code in the first readable state 424 and can be read together therewith as a single bar code as in the state designated by D in FIG. 4B.

Reference is now made to FIG. 4C, which is a simplified illustration of the construction and operation of one embodiment of the indicator 221 of FIG. 2C for separately indicating elapse of time and temperature history. As seen in FIG. 4C, the indicator, here designated by reference numeral 440, preferably includes a bar code defining layer 442, which is preferably printed on a transparent substrate. The printing on the transparent substrate preferably defines a bar code in a first readable state 444 and alongside it, at a first end thereof, a first plurality of transparent areas 446, which, if colored and read together with the bar code in the first readable state 444, provide a bar code in a second readable state 448.

The printing on the transparent substrate also preferably defines alongside the bar code in a first readable state 444, at a second end thereof, a second plurality of transparent areas 450, which, if colored and read together with the bar code in the first readable state 444, provide a bar code in a third readable state 452. It is appreciated that if both the first and second pluralities of transparent areas are colored and read together with the bar code in the first readable state, there is provided a bar code in a fourth readable state 454.

The printing on the transparent substrate also preferably defines alongside the second plurality of transparent areas 450, a third plurality of transparent areas 456, which, if colored and read together with the bar code in the first readable state 444 and the colored second plurality of transparent areas 450, provide a bar code in a fifth readable state (not shown). It is appreciated that if the first, second and third pluralities of transparent areas 446, 450 and 456 are all colored and read together with the bar code in the first readable state 444, there is provided a bar code in a sixth readable state 458.

It is appreciated that the remainder of the bar code defining layer 442, other than the bar code in a first readable state 444 and the transparent areas 446, 450 and 456, is preferably printed in a white color or a color defining high contrast with respect to the bar code in the first readable state 444.

Disposed behind transparent areas 446 of bar code defining layer 442, there is preferably provided a temperature responsive coloring element 460, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 460 and bar code defining layer 442 at transparent areas 446 is an opaque layer 462 of a color which defines high contrast with respect to the bar code in a first readable state 444.

Disposed behind transparent areas 450 of bar code defining layer 442 is a first elapsed time responsive coloring assembly 470, including a temperature responsive release coloring element 472, a relatively long-term coloring agent diffusion pathway defining element 474 and a relatively quick coloring agent diffusion region defining element 476. The temperature responsive release coloring element 472 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 474 preferably comprises a strip of paper, such as Grade 3 qualitative filter paper commercially available from Whatman plc of the UK, one end of which lies adjacent coloring element 472 and an opposite end of which extends to element 476. Relatively quick coloring agent diffusion region defining element 476 preferably comprises a strip of paper, such as Grade 4 qualitative filter paper commercially available from Whatman plc of the UK, which has a much higher speed of diffusion for the coloring agent than does element 474, thus ensuring that a time when the bar code is between its first and second readable states is minimized. It is appreciated that alternatively element 476 may be obviated and element 474 extends under all of transparent areas 450.

Disposed behind transparent areas 456 of bar code defining layer 442 and behind first elapsed time responsive coloring assembly 470 is a second elapsed time responsive coloring assembly 480, including a temperature responsive release coloring element 482, a relatively long-term coloring agent diffusion pathway defining element 484 and a relatively quick coloring agent diffusion region defining element 486. The temperature responsive release coloring element 482 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 484 preferably comprises a strip of paper, such as Grade 3 qualitative filter paper commercially available from Whatman plc of the UK, one end of which lies adjacent coloring element 482 and an opposite end of which extends to element 486. Relatively quick coloring agent diffusion region defining element 486 preferably comprises a strip of paper, such as Grade 4 qualitative filter paper commercially available from Whatman plc of the UK, which has a much higher speed of diffusion for the coloring agent than does element 484, thus ensuring that a time when the bar code is between its first and second readable states is minimized. It is appreciated that alternatively element 486 may be obviated and element 484 extends under all of transparent areas 456. It is also appreciated that the first and second elapsed time responsive coloring assemblies 470 and 480 are constructed, positioned and operative so that they do not interfere with each other.

When the indicator 440 is maintained at 4 degrees Celsius, and substantially no time has elapsed since actuation of the indicator, the indicator is in the state shown designated by A in FIG. 4C.

When the temperature at the indicator rises above 4 degrees Celsius, the coloring agent on coloring element 460 begins to melt and be released from coloring element 460 and begins to diffuse through the opaque layer 462. When the temperature exceeds 4 degrees Celsius for at least a minimum time, such as five minutes, the coloring agent rapidly diffuses through opaque layer 462, such that the portions of the opaque layer 462 which are readable through the transparent areas 446 appear similarly to the bar code in the first readable state 444 and can be read together therewith as a single bar code as in the state designated by B in FIG. 4C.

The coloring agent on coloring element 472 begins to melt generally immediately and be released from coloring element 472 and begins to diffuse through relatively long-term coloring agent diffusion pathway defining element 474. When the elapsed time is greater than a first predetermined time, such as one week, the coloring agent progresses towards the end of the pathway defined by the relatively long-term coloring agent diffusion pathway defining element 474 and reaches relatively quick coloring agent diffusion region defining element 476, where it rapidly impregnates the portions of the element 476 which are readable through the transparent areas 450 so that they appear similarly to the bar code in the first readable state 444 and can be read together therewith as a single bar code as in the state designated by C in FIG. 4C.

When the elapsed time is greater than the first predetermined time and the temperature has exceeded 4 degrees Celsius, such as 15 degrees Celsius, both transparent areas 446 and 450 are colored and can be read together with the bar code in the first readable state 444 as a single bar code as in the state designated by D in FIG. 4C.

The coloring agent on coloring element 482 begins to melt generally immediately and be released from coloring element 482 and begins to diffuse through relatively long-term coloring agent diffusion pathway defining element 484. When the elapsed time is greater than a second predetermined time, such as two weeks, the coloring agent progresses towards the end of the pathway defined by the relatively long-term coloring agent diffusion pathway defining element 484 and reaches relatively quick coloring agent diffusion region defining element 486, where it rapidly impregnates the portions of the element 486 which are readable through the transparent areas 456 so that they appear similarly to the bar code in the first readable state 444 and can be read together therewith and with the colored transparent areas 450 as a single bar code.

When the elapsed time is greater than the second predetermined time and the temperature has exceeded 4 degrees Celsius, such as 15 degrees Celsius, transparent areas 446, 450 and 456 are all colored and can be read together with the bar code in the first readable state 444 as a single bar code as in the state designated by E in FIG. 4C.

Figure 4D:
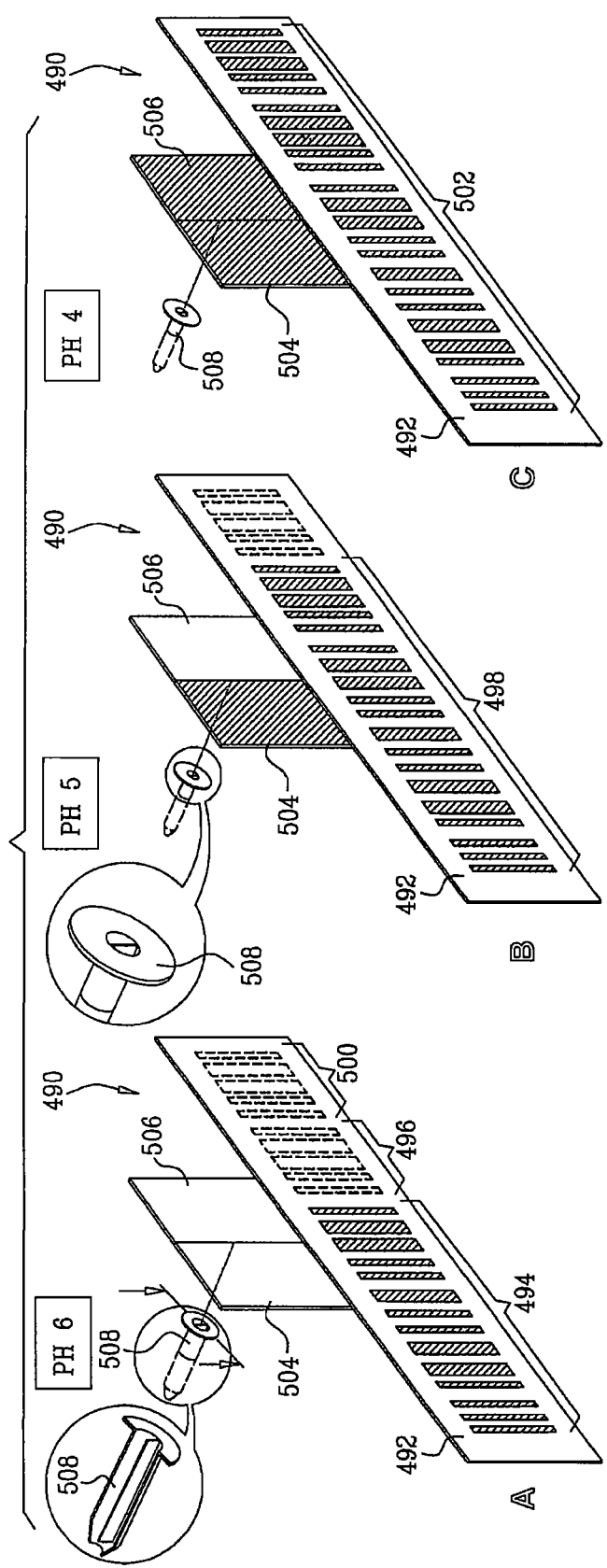
FIG. 4D is a simplified illustration of the structure and operation of an example of the indicator of FIG. 2D, in accordance with a preferred embodiment of the present invention.

Reference is now made to FIG. 4D, which is a simplified illustration of the construction and operation of one embodiment of the indicator 232 of FIG. 2D for indicating two different levels of pH. As seen in FIG. 4D, the indicator, here designated by reference numeral 490, preferably includes a bar code defining layer 492, which is preferably printed on a transparent substrate. The printing on the transparent substrate preferably defines a bar code in a first readable state 494 and alongside it, at an end thereof, a first plurality of transparent areas 496, which, if colored and read together with the bar code in the first readable state 494, provide a bar code in a second readable state 498.

The printing on the transparent substrate also preferably defines alongside the first plurality of transparent areas 496, a second plurality of transparent areas 500, which, if colored and read together with the bar code in the first readable state 494 and the colored first plurality of transparent areas 496, provide a bar code in a third readable state 502.

It is appreciated that the remainder of the bar code defining layer 492, other than the bar code in a first readable state 494 and the transparent areas 496 and 500, is preferably printed in a white color or a color defining high contrast with respect to the bar code in the first readable state 494.

Disposed behind transparent areas 496 of bar code defining layer 492, there is preferably provided a pH responsive coloring element 504, such as a piece of litmus type paper which normally appears in a white color or a color defining high contrast with respect to the bar code in the first readable state 494. Element 504 preferably is responsive to exposure to a fluid of pH less than 6 to change its color to a color defining high contrast with the remainder of the bar code defining layer 492, preferably a color similar to that of the bar code in the first readable state 494.

Disposed behind transparent areas 500 of bar code defining layer 442, there is preferably provided a pH responsive coloring element 506, such as a piece of litmus type paper which normally appears in a white color or a color defining high contrast with respect to the bar code in the first readable state 494. Element 506 preferably is responsive to exposure to a fluid of pH less than 5 to change its color to a color defining high contrast with the remainder of the bar code defining layer 492, preferably a color similar to that of the bar code in the first readable state 494.

A fluid conduit, such as a hollow pin 508, supplies a sample of the contents of the container 230 of FIG. 2D, such as milk, to coloring elements 504 and 506.

When the contents of container 230 are maintained at a pH at or above 6, the indicator 490 is in the state designated by A in FIG. 4D.

When the contents of container 230 reach a pH below 6, the pH responsive coloring element 504 changes color, such that the portions of the coloring element 504 which are readable through the transparent areas 496 appear similarly to the bar code in the first readable state 494 and can be read together therewith as a single bar code in second readable state 498, as designated by B in FIG. 4D.

When the contents of container 230 reach a pH below 5, the pH responsive coloring element 506 changes color, such that the portions of the coloring element 506 which are readable through the transparent areas 500 appear similarly to the bar code in the first readable state 494 and can be read together therewith and with the colored portions of the bar code which are readable through the transparent areas 496 as a single bar code in third readable state 502, as designated by C in FIG. 4D.

It is appreciated that as an alternative to the structure described hereinabove with reference to FIG. 4D, the entire indicator may be located within container 230 such that coloring elements 504 and 506 are in communication with the fluid therein and pin 508 may be obviated. In such a case, the indicator 490 may be viewed through a transparent window formed in a wall of the container 230.

Figure 4E:
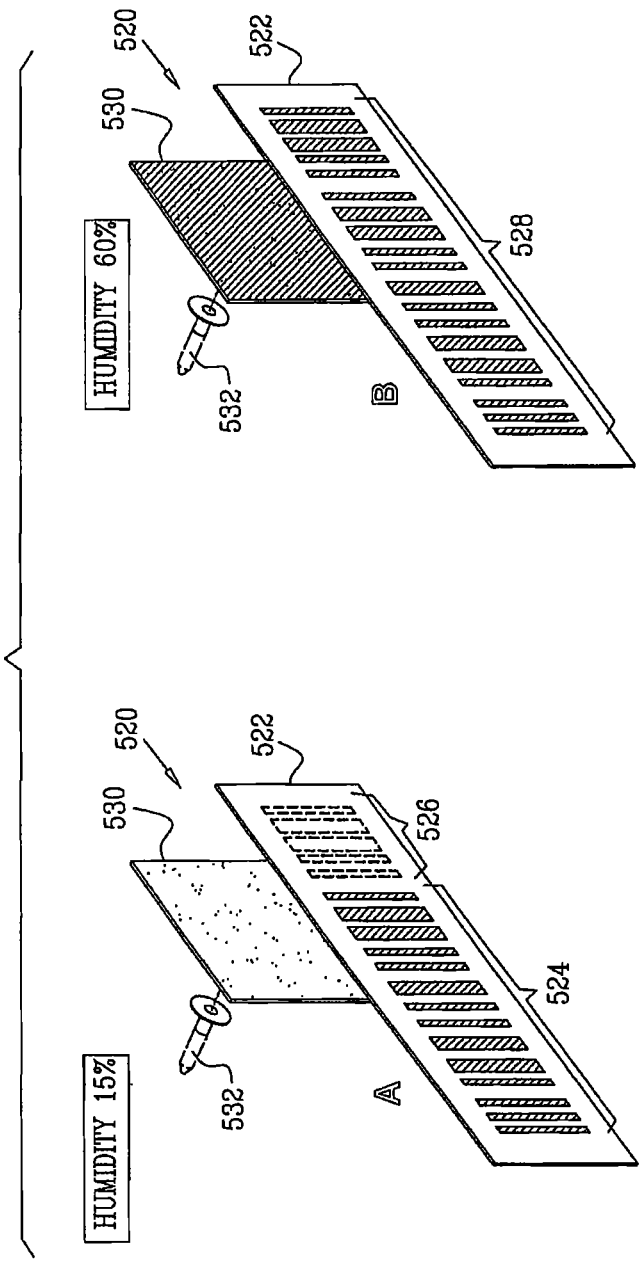
FIG. 4E is a simplified illustration of the structure and operation of an example of the indicator of FIG. 2E, in accordance with a preferred embodiment of the present invention.

Reference is now made to FIG. 4E, which is a simplified illustration of the construction and operation of one embodiment of the indicator 242 of FIG. 2E for indicating humidity history. As seen in FIG. 4E, the indicator, here designated by reference numeral 520, preferably includes a bar code defining layer 522, which is preferably printed on a transparent substrate. The printing on the transparent substrate preferably defines a bar code in a first readable state 524 and alongside it, at an end thereof, a plurality of transparent areas 526, which, if colored and read together with the bar code in the first readable state 524, provide a bar code in a second readable state 528.

It is appreciated that the remainder of the bar code defining layer 522, other than the bar code in a first readable state 524 and the transparent areas 526, is preferably printed in a white color or a color defining high contrast with respect to the bar code in the first readable state 524.

Disposed behind transparent areas 526 of bar code defining layer 522, there is preferably provided a humidity responsive coloring element 530, such as a substrate coated with silica gel which normally appears in a first color or a color defining high contrast with respect to the bar code in the first readable state 524. Element 530 preferably is responsive to exposure to relative humidity of more than 50% to change its color to a color defining high contrast with the remainder of the bar code defining layer 522, preferably a color similar to that of the bar code in the first readable state 524.

A fluid conduit, such as a hollow pin 532, supplies a sample of the fluid inside the container 240 of FIG. 2E, such as air, to coloring element 530.

When the contents of container 240 are maintained at a relative humidity of less than 50%, such as 15%, the indicator 520 is in the state designated by A in FIG. 4E.

When the contents of container 240 reach a relative humidity in excess of 50%, such as 60%, the coloring element 530 changes color, such that the portions of the coloring element 530 which are readable through the transparent areas 526 appear similarly to the bar code in the first readable state 524 and can be read together therewith as a single bar code in second readable state 528, as designated by B in FIG. 4E.

It is appreciated that as an alternative to the structure described hereinabove with reference to FIG. 4E, the entire indicator may be located within the container such that coloring element 530 is in communication with the fluid therein and pin 532 may be obviated. In such a case, the indicator 520 may be viewed through a transparent window formed in a wall of the container 240 or the indicator 520 may measure the relative humidity outside the container 240 rather than interiorly thereof.

Reference is now made to FIG. 4F, which is a simplified illustration of the construction and operation of one embodiment of the indicator 252 of FIG. 2F for indicating impact history. As seen in FIG. 4F, the indicator, here designated by reference numeral 540, preferably includes a bar code defining layer 542, which is preferably printed on a transparent substrate. The printing on the transparent substrate preferably defines a bar code in a first readable state 544 and alongside it, at an end thereof, a plurality of transparent areas 546, which, if colored and read together with the bar code in the first readable state 544, provide a bar code in a second readable state 548.

It is appreciated that the remainder of the bar code defining layer 542, other than the bar code in a first readable state 544 and the transparent areas 546, is preferably printed in a white color or a color defining high contrast with respect to the bar code in the first readable state 544.

Disposed behind transparent areas 546 of bar code defining layer 542, there is preferably provided an impact responsive coloring assembly element 550, such as a substrate 552 including a surface portion 554 facing the bar code defining layer 542, which has a color defining high contrast with the remainder of the bar code defining layer 542, preferably a color similar to that of the bar code in the first readable state 544. Mounted, in a impact sensitive manner, over surface portion 554 and intermediate surface portion 554 and transparent areas 546 is a cover assembly 556, having a surface portion 560, facing the bar code defining layer 542, which has a color defining high contrast with respect to the bar code in the first readable state 544. Upon application of at least a predetermined impact force, such as 10 G, one or more pins 562, which, when intact, prevent displacement of cover assembly 556 from blocking surface portion 554, are broken or removed, allowing cover assembly 556 to be displaced and thus allow surface portion 554 to be seen through transparent areas 546.

When the package 250 of FIG. 2F has not experienced an impact force greater than the predetermined impact force, the indicator 540 displays a bar code in first readable state 544 as designated by A in FIG. 4F.

When an impact force of at least the predetermined impact force is applied to the package 250, breakage or removal of one or more pins 562 results, as indicated at B in FIG. 4F.

Thereafter, as indicated at C in FIG. 4F, colored surface portion 554 is readable through transparent areas 546, thus providing a bar code in second readable state 548.

Figure 4G:
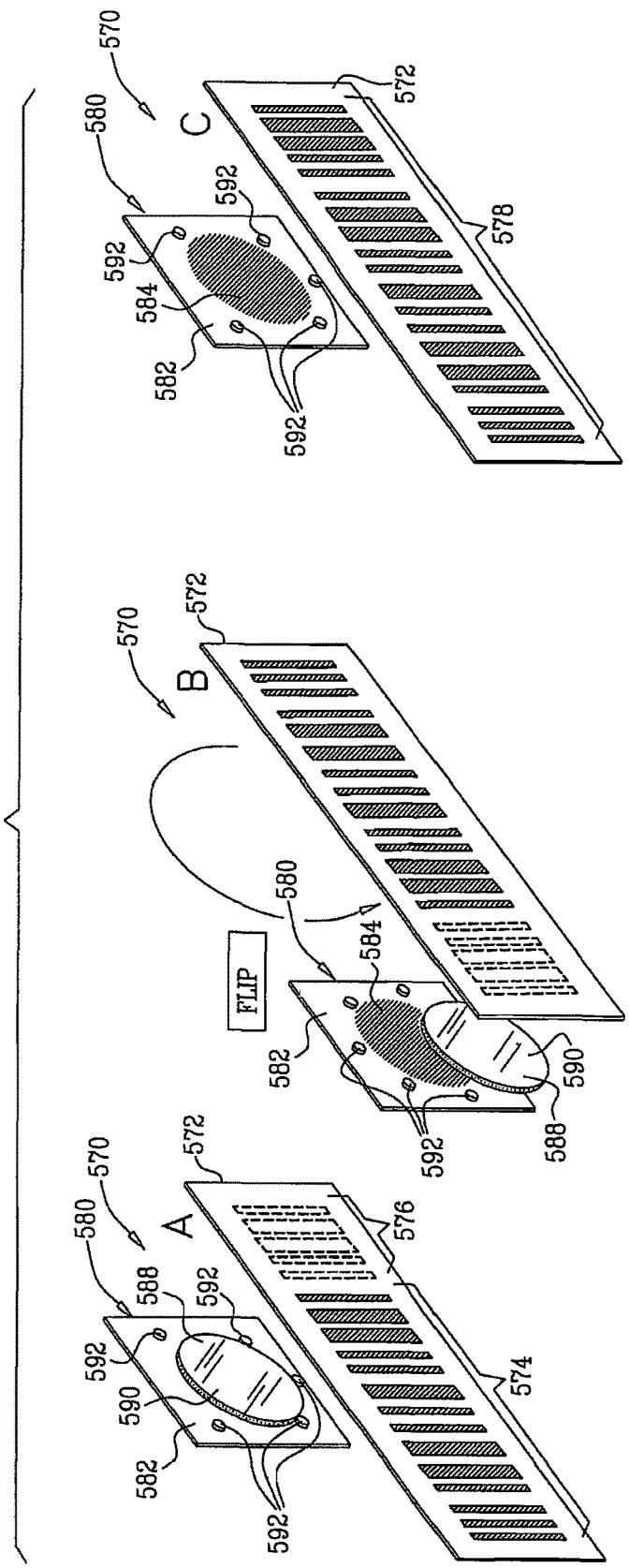
FIG. 4G is a simplified illustration of the structure and operation of an example of the indicator of FIG. 2G, in accordance with a preferred embodiment of the present invention.

Reference is now made to FIG. 4G, which is a simplified illustration of the construction and operation of one embodiment of the indicator 262 of FIG. 2G for indicating orientation history. As seen in FIG. 4G, the indicator, here designated by reference numeral 570, preferably includes a bar code defining layer 572, which is preferably printed on a transparent substrate. The printing on the transparent substrate preferably defines a bar code in a first readable state 574 and alongside it, at an end thereof, a plurality of transparent areas 576, which, if colored and read together with the bar code in the first readable state 574, provide a bar code in a second readable state 578.

It is appreciated that the remainder of the bar code defining layer 572, other than the bar code in a first readable state 574 and the transparent areas 576, is preferably printed in a white color or a color defining high contrast with respect to the bar code in the first readable state 574.

Disposed behind transparent areas 576 of bar code defining layer 572, there is preferably provided an orientation responsive coloring assembly element 580, such as a substrate 582 including a surface portion 584 facing the bar code defining layer 572, which has a color defining high contrast with the remainder of the bar code defining layer 572, preferably a color similar to that of the bar code in the first readable state 574. Mounted, in an orientation sensitive manner, over surface portion 584 and intermediate surface portion 584 and transparent areas 576 is a cover assembly 588, having a surface portion 590, facing the bar code defining layer 572, which has a color defining high contrast with respect to the bar code in the first readable state 574. The cover assembly 588 is normally kept in place over surface portion 584 by a plurality of pins 592 arranged so as to allow displacement of the cover assembly 588 only when the orientation of the indicator is changed by at least 170 degrees. Upon a change of orientation of at least 170 degrees, the cover assembly 588 is displaced and thus allows surface portion 584 to be seen through transparent areas 576.

When the package 260 of FIG. 2G has not experienced a change in orientation typically of at least 170 degrees, the indicator 570 displays a bar code in first readable state 574 as designated by A in FIG. 4G.

When a change of orientation of at least 170 degrees is applied to the package 260, displacement of cover assembly 588 results, as indicated at B in FIG. 4G.

Thereafter, as indicated at C in FIG. 4G, colored surface portion 584 is readable through transparent areas 576, thus providing a bar code in second readable state 578.

Figure 5A:
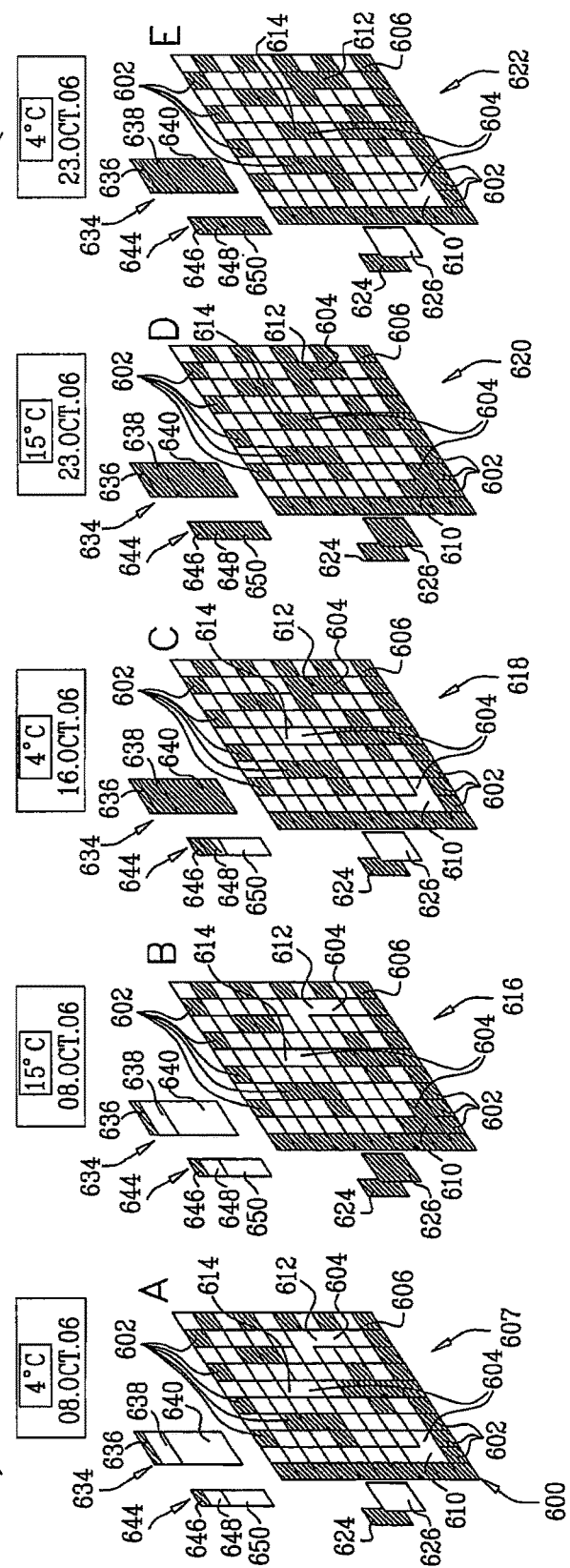
FIG. 5A is a simplified illustration of the structure and operation of an example of the indicator of FIG. 3A in accordance with a preferred embodiment of the present invention.

Reference is now made to FIG. 5A, which is a simplified illustration of the construction and operation of one example of an indicator suitable for use as the indicator 302 of FIG. 3A, for separately indicating elapsed time and temperature in accordance with a preferred embodiment of the present invention. The indicator, here designated by reference numeral 600, is a two-dimensional indicator which includes a plurality of fixed machine-readable cells 602, mainly arranged along the periphery of the indicator to provide an indication of orientation and registration, and a plurality of variable machine-readable cells 604, which separately indicate elapsed time and temperature.

As seen in FIG. 5A, indicator 600 preferably includes a machine-readable code defining layer 606, which is preferably printed on a transparent substrate. The printing on the transparent substrate preferably defines a two-dimensional machine-readable code in a first readable state 607, which includes the fixed machine-readable cells 602, and a plurality of transparent areas which include one or more variable machine-readable cells 604. In the illustrated embodiment, the transparent areas are three in number and designated by reference numerals 610, 612 and 614.

If transparent area 610 is colored and read together with the two-dimensional machine-readable code in a first readable state 607 it provides a machine-readable code in a second readable state 616.

If transparent area 612 is colored and read together with the two-dimensional machine-readable code in a first readable state 607 it provides a machine-readable code in a third readable state 618.

If transparent areas 610, 612 and 614 are all colored and read together with the two-dimensional machine-readable code in a first readable state 607 they provide a machine readable code in a fourth readable state 620.

If transparent areas 612 and 614 are both colored and read together with the two-dimensional machine-readable code in a first readable state 607 they provide a machine readable code in a fifth readable state 622.

It is appreciated that the remainder of the machine-readable code defining layer 602, other than the machine-readable code in a first readable state 607 and the transparent areas 610, 612 and 614, is preferably printed in a white color or a color defining high contrast with respect to the machine-readable code in the first readable state 607.

Disposed behind transparent area 610 of machine-readable code defining layer 606 there is preferably provided a temperature responsive coloring element 624, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 624 and machine-readable code defining layer 606 at transparent areas 610 is an opaque layer 626 of a color which defines high contrast with respect to the machine-readable code in a first readable state 607.

Disposed behind transparent area 612 of machine-readable code defining layer 606 is a first elapsed time responsive coloring assembly 634, including a coloring element 636, a relatively long-term coloring agent diffusion pathway defining element 638 and a relatively quick coloring agent diffusion region defining element 640. The coloring element 636 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 638 preferably comprises a strip of paper, such as Grade 3 qualitative filter paper commercially available from Whatman plc of the UK, one end of which lies adjacent coloring element 636 and an opposite end of which extends to element 640. Relatively quick coloring agent diffusion region defining element 640 preferably comprises a strip of paper, such as Grade 4 qualitative filter paper commercially available from Whatman plc of the UK, which has a much higher speed of diffusion for the coloring agent than does element 638, thus ensuring that a time when the machine-readable code is between its first and second readable states is minimized. It is appreciated that alternatively element 640 may be obviated and element 638 extends under all of transparent area 612.

Disposed behind transparent area 614 of machine-readable code defining layer 606 is a second elapsed time responsive coloring assembly 644, including a coloring element 646, a relatively long-term coloring agent diffusion pathway defining element 648 and a relatively quick coloring agent diffusion region defining element 650. The coloring element 646 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 648 preferably comprises a strip of paper, such as Grade 3 qualitative filter paper commercially available from Whatman plc of the UK, one end of which lies adjacent coloring element 646 and an opposite end of which extends to element 650. Relatively quick coloring agent diffusion region defining element 650 preferably comprises a strip of paper, such as Grade 4 qualitative filter paper commercially available from Whatman plc of the UK, which has a much higher speed of diffusion for the coloring agent than does element 648, thus ensuring that a time when the machine-readable code is between readable states is minimized. It is appreciated that alternatively element 650 may be obviated and element 648 extends under all of transparent area 614.

When the indicator 600 is maintained at 4 degrees Celsius, and substantially no time has elapsed since actuation of the indicator, the indicator is in the state designated by A in FIG. 5A.

When the temperature at the indicator 600 rises above 4 degrees Celsius, the coloring agent on coloring element 624 begins to melt and be released from coloring element 624 and begins to diffuse through the opaque layer 626. When the temperature exceeds 4 degrees Celsius for at least a minimum time, such as five minutes, the coloring agent rapidly diffuses through opaque layer 626, such that the portions of the opaque layer 626 which are readable through the transparent area 610 appears similarly to the machine-readable code in the first readable state 607 and can be read together therewith as a single bar code in the second readable state 616 as designated by B in FIG. 5A.

The coloring agent on coloring element 636 begins to melt generally immediately and be released from coloring element 636 and begins to diffuse through relatively long-term coloring agent diffusion pathway defining element 638. When the elapsed time is greater than a first predetermined time, such as one week, the coloring agent progresses towards the end of the pathway defined by the relatively long-term coloring agent diffusion pathway defining element 638 and reaches relatively quick coloring agent diffusion region defining element 640, where it rapidly impregnates the portion of the element 640 which is readable through the transparent area 612 so that it appears similarly to the machine-readable code in the first readable state 607 and can be read together therewith as a single bar code in the third readable state 618 as designated by C in FIG. 5A.

The coloring agent on coloring element 646 begins to melt generally immediately and be released from coloring element 646 and begins to diffuse through relatively long-term coloring agent diffusion pathway defining element 648. When the elapsed time is greater than a second predetermined time, such as two weeks, the coloring agent progresses towards the end of the pathway defined by the relatively long-term coloring agent diffusion pathway defining element 648 and reaches relatively quick coloring agent diffusion region defining element 650, where it rapidly impregnates the portions of the element 650 which are readable through the transparent area 614 so that they appear similarly to the machine-readable code in the first readable state 607 and can be read together therewith and with the colored transparent area 612 as a single machine-readable code.

When the elapsed time is greater than the second predetermined time and the temperature has exceeded 4 degrees Celsius, such as 15 degrees Celsius, transparent areas 610, 612 and 614 are all colored and can be read together with the machine-readable code in the first readable state 607 as a single machine-readable code in the fourth readable state 620 as designated by D in FIG. 5A.

When the elapsed time is greater than the second predetermined time and the temperature has not exceeded 4 degrees Celsius, transparent areas 612 and 614 are both colored and can be read together with the machine-readable code in the first readable state 607 as a single machine-readable code in the fifth readable state 622 as designated by E in FIG. 5A.

Reference is now made to FIG. 5B, which is a simplified illustration of the construction and operation of one example of an indicator suitable for use as the indicator 322 of FIG. 3B, for separately indicating humidity and temperature in accordance with a preferred embodiment of the present invention. The indicator, here designated by reference numeral 660, is a two-dimensional indicator which includes a plurality of fixed machine-readable cells 662, mainly arranged along the periphery of the indicator to provide an indication of orientation and registration, and a plurality of variable machine-readable cells 664, which separately indicate humidity and temperature.

As seen in FIG. 5B, indicator 660 preferably includes a machine-readable code defining layer 666, which is preferably printed on a transparent substrate. The printing on the transparent substrate preferably defines a two-dimensional machine-readable code in a first readable state 667, which includes the fixed machine-readable cells 662, and a plurality of transparent areas which include variable machine-readable cells 664. In the illustrated embodiment, the transparent areas are three in number and designated by reference numerals 670, 672 and 674.

If transparent areas 670 and 672 are both colored and read together with the two-dimensional machine-readable code in a first readable state 667 they provide a machine readable code in a second readable state (not shown).

If transparent areas 670, 672 and 674 are all colored and read together with the two-dimensional machine-readable code in a first readable state 667 they provide a machine readable code in a third readable state 680.

It is appreciated that the remainder of the machine-readable code defining layer 666, other than the machine-readable code in a first readable state 667 and the transparent areas 670, 672 and 674, is preferably printed in a white color or a color defining high contrast with respect to the machine-readable code in the first readable state 667.

Disposed behind transparent area 670 of machine-readable code defining layer 666 there is preferably provided a first temperature responsive coloring element 684, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 684 and machine-readable code defining layer 666 at transparent area 670 is an opaque layer 686 of a color which defines high contrast with respect to the machine-readable code in a first readable state 667.

Disposed behind transparent area 672 of machine-readable code defining layer 666 there is preferably provided a second temperature responsive coloring element 694, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 694 and machine-readable code defining layer 666 at transparent area 672 is an opaque layer 696 of a color which defines high contrast with respect to the machine-readable code in a first readable state 667.

Disposed behind transparent area 674 of machine-readable code defining layer 666 there is preferably provided a humidity responsive coloring element 704, such as a substrate coated with silica gel which normally appears in a first color or a color defining high contrast with respect to the machine-readable code in the first readable state 667. Element 704 preferably is responsive to exposure to relative humidity of more than 50% to change its color to a color defining high contrast with the remainder of the machine-readable code defining layer 666, preferably a color similar to that of the machine-readable code in the first readable state 667.

A fluid conduit, such as a hollow pin 706, supplies a sample of the fluid inside the container 320 of FIG. 3B, such as air, to coloring element 704.

When the contents of container 320 are maintained at a relative humidity of less than 50%, such as 15%, and at a temperature of less than 30 degrees Celsius, the indicator 660 is in the first readable state 667 designated by A in FIG. 5B.

When the contents of container 320 reach a temperature of more than 30 degrees Celsius, such as 33 degrees Celsius, the coloring agent on coloring element 684 begins to melt and be released from coloring element 684 and begins to diffuse through the opaque layer 686. When the temperature exceeds 30 degrees Celsius for at least a minimum time, such as five minutes, the coloring agent rapidly diffuses through opaque layer 686, such that the portion of the opaque layer 686 which is readable through the transparent area 670 appears similarly to the machine-readable code in the first readable state 667.

When the contents of container 320 reach a temperature of more than 30 degrees Celsius, such as 33 degrees Celsius, the coloring agent on coloring element 694 also begins to melt and be released from coloring element 694 and begins to diffuse through the opaque layer 696. When the temperature exceeds 30 degrees Celsius for at least a minimum time, such as five minutes, the coloring agent rapidly diffuses through opaque layer 696, such that the portion of the opaque layer 696 which is readable through the transparent area 672 appears similarly to the machine-readable code in the first readable state 667.

When the contents of container 320 reach a relative humidity in excess of 50%, such as 60%, the coloring element 704 changes color, such that the portion of the coloring element 704 which is readable through the transparent area 674 appears similarly to the machine-readable code in the first readable state 667 and can be read together therewith and with the colored transparent areas 670 and 672 as a single bar code in second readable state 676, as designated by B in FIG. 5B.

It is appreciated that as an alternative to the structure described hereinabove with reference to FIG. 5B, the entire indicator may be located within the container such that coloring element 704 is in communication with the fluid therein and pin 706 may be obviated. In such a case, the indicator 660 may be viewed through a transparent window formed in a wall of the container 320 or the indicator 660 may measure the relative humidity outside the container 320 rather than interiorly thereof.

It is appreciated that in this embodiment multiple areas provide temperature information. It is appreciated that multiple areas may be used to indicate multiple temperature levels and/or to provide redundancy in indicating the same temperature level.

Figure 5C:
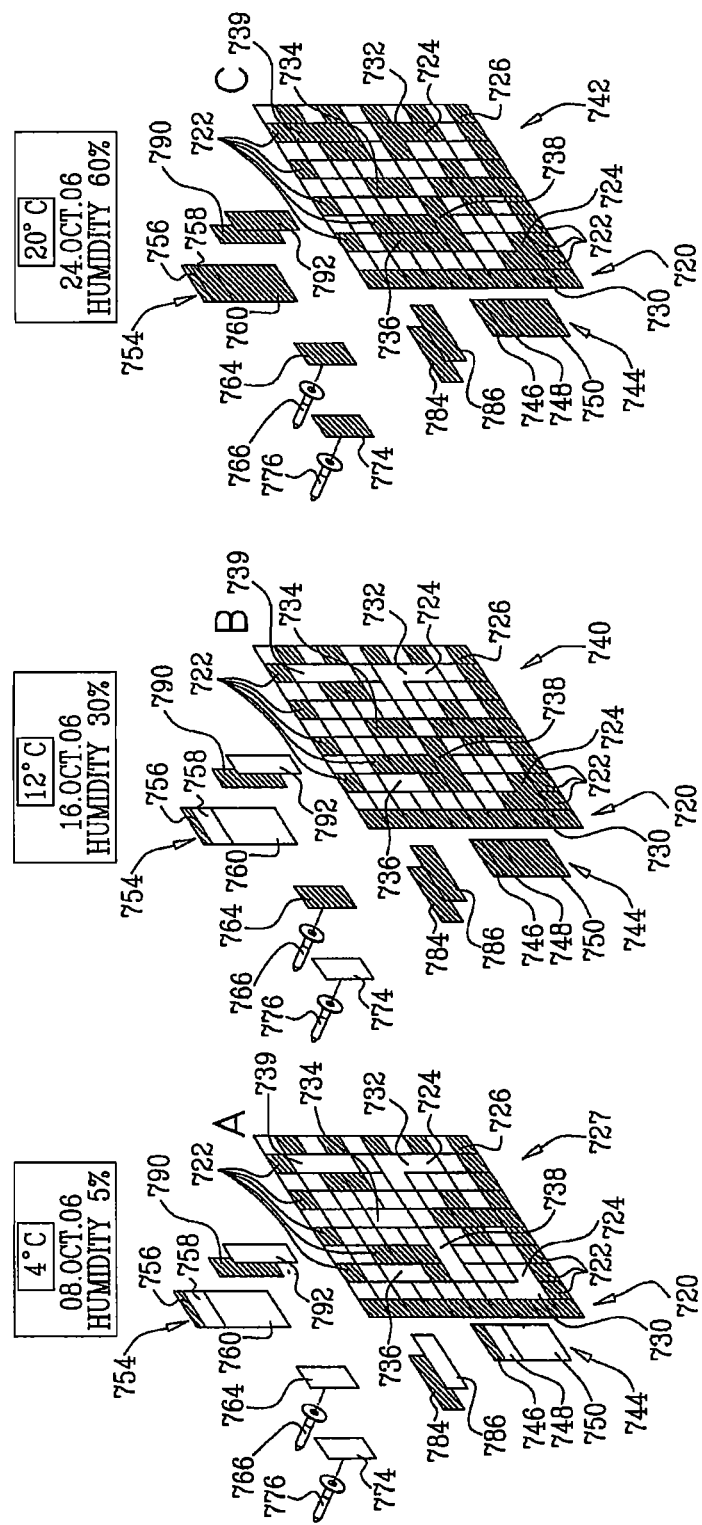
FIG. 5C is a simplified illustration of the structure and operation of an example of the indicator of FIG. 3C in accordance with a preferred embodiment of the present invention.

Reference is now made to FIG. 5C, which is a simplified illustration of the construction and operation of one example of an indicator suitable for use as the indicator 352 of FIG. 3C, for separately indicating elapsed time, humidity and temperature in accordance with a preferred embodiment of the present invention. The indicator, here designated by reference numeral 720, is a two-dimensional indicator which includes a plurality of fixed machine-readable cells 722, mainly arranged along the periphery of the indicator to provide an indication of orientation and registration, and a plurality of variable machine-readable cells 724 which separately indicate elapsed time, humidity and temperature.

As seen in FIG. 5C, indicator 720 preferably includes a machine-readable code defining layer 726, which is preferably printed on a transparent substrate. The printing on the transparent substrate preferably defines a two-dimensional machine-readable code in a first readable state 727, which includes the fixed machine-readable cells 722, and a plurality of transparent areas which include variable machine-readable cells 724. In the illustrated embodiment, the transparent areas are six in number and designated by reference numerals 730, 732, 734, 736, 738 and 739.

If transparent areas 730, 734 and 738 are colored and read together with the two-dimensional machine-readable code in a first readable state 727 they provides a machine readable code in a second readable state 740.

If transparent areas 730, 732, 734, 736, 738 and 739 are all colored and read together with the two-dimensional machine-readable code in a first readable state 727 they provide a machine readable code in a third readable state 742.

It is appreciated that the remainder of the machine-readable code defining layer 726, other than the machine-readable code in a first readable state 727 and the transparent areas 730, 732, 734, 736, 738 and 739, is preferably printed in a white color or a color defining high contrast with respect to the machine-readable code in the first readable state 727.

Disposed behind transparent area 730 of machine-readable code defining layer 726 there is preferably provided a first elapsed time responsive coloring assembly 744, including a coloring element 746, a relatively long-term coloring agent diffusion pathway defining element 748 and a relatively quick coloring agent diffusion region defining element 750. The coloring element 746 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 748 preferably comprises a strip of paper, such as Grade 3 qualitative filter paper commercially available from Whatman plc of the UK, one end of which lies adjacent coloring element 746 and an opposite end of which extends to element 750. Relatively quick coloring agent diffusion region defining element 750 preferably comprises a strip of paper, such as Grade 4 qualitative filter paper commercially available from Whatman plc of the UK, which has a much higher speed of diffusion for the coloring agent than does element 748, thus ensuring that a time when the machine-readable code is between its first and second readable states is minimized. It is appreciated that alternatively element 750 may be obviated and element 748 extends under all of transparent area 730.

Disposed behind transparent area 732 of machine-readable code defining layer 726 is a second elapsed time responsive coloring assembly 754, including a coloring element 756, a relatively long-term coloring agent diffusion pathway defining element 758 and a relatively quick coloring agent diffusion region defining element 760. The coloring element 756 preferably comprises a substrate, such as paper or a non-woven fabric impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium.

The relatively long-term coloring agent diffusion pathway defining element 758 preferably comprises a strip of paper, such as Grade 3 qualitative filter paper commercially available from Whatman plc of the UK, one end of which lies adjacent coloring element 756 and an opposite end of which extends to element 760. Relatively quick coloring agent diffusion region defining element 760 preferably comprises a strip of paper, such as Grade 4 qualitative filter paper commercially available from Whatman plc of the UK, which has a much higher speed of diffusion for the coloring agent than does element 758, thus ensuring that a time when the machine-readable code is between readable states is minimized. It is appreciated that alternatively element 760 may be obviated and element 758 extends under all of transparent area 732.

Disposed behind transparent area 734 of machine-readable code defining layer 726 there is preferably provided a first humidity responsive coloring element 764, such as a substrate coated with silica gel which normally appears in a first color or a color defining high contrast with respect to the machine-readable code in the first readable state 727. Element 764 preferably is responsive to exposure to relative humidity of more than 10% to change its color to a color defining high contrast with the remainder of the machine-readable code defining layer 726, preferably a color similar to that of the machine-readable code in the first readable state 727.

A first fluid conduit, such as a first hollow pin 766, supplies a sample of the fluid inside the package 350 of FIG. 3C, such as air, to coloring element 764.

Disposed behind transparent area 736 of machine-readable code defining layer 726 there is preferably provided a second humidity responsive coloring element 774, such as a substrate coated with silica gel which normally appears in a first color or a color defining high contrast with respect to the machine-readable code in the first readable state 727. Element 774 preferably is responsive to exposure to relative humidity of more than 40% to change its color to a color defining high contrast with the remainder of the machine-readable code defining layer 726, preferably a color similar to that of the machine-readable code in the first readable state 727.

A second fluid conduit, such as a second hollow pin 776, supplies a sample of the fluid inside the package 350, such as air, to coloring element 774. Alternatively, a single fluid conduit may communicate with multiple color elements.

Disposed behind transparent area 738 of machine-readable code defining layer 726 there is preferably provided a first temperature responsive coloring element 784, such as a piece of paper impregnated with a coloring agent, such as Nigrosine, Alcohol soluble, a black color dye [CAS: 11099-03-9], commercially available from Acros Organics of Geel, Belgium, dissolved in 2'-Hydroxyacetophenone 99.9% solvent [CAS: 118-93-4], commercially available from Acros Organics of Geel, Belgium. Disposed intermediate temperature responsive color element 784 and machine-readable code defining layer 726 at transparent area 738 is an opaque layer 786 of a color which defines high contrast with respect to the machine-readable code in a first readable state 727.

Disposed behind transparent area 739 of machine-readable code defining layer 726 there is preferably provided a second temperature responsive coloring element 790, such as a piece of paper impregnated with a coloring agent, such as Sudan Black B, a black color dye [CAS: 4197-25-5], commercially available from Acros Organics of Geel, Belgium, dissolved in DiMethyl Sulfoxide [CAS: 67-68-5], commercially available from Acros Organics of Geel, Belgium. Disposed intermediate temperature responsive color element 790 and machine-readable code defining layer 726 at transparent area 739 is an opaque layer 792 of a color which defines high contrast with respect to the machine-readable code in a first readable state 727.

When the contents of package 350 are maintained at a relative humidity of less than 10%, such as 5%, and at a temperature of less than 5 degrees Celsius and when less than one week has elapsed since packaging, the indicator 720 is in the first readable state 727 as designated by A in FIG. 5C.

When the contents of package 350 reach a temperature of more than 4 degrees Celsius, such as 12 degrees Celsius, the coloring agent on coloring element 784 begins to melt and be released from coloring element 784 and begins to diffuse through the opaque layer 786. When the temperature exceeds 4 degrees Celsius for at least a minimum time, such as five minutes, the coloring agent rapidly diffuses through opaque layer 786, such that the portion of the opaque layer 786 which is readable through the transparent area 730 appears similarly to the machine-readable code in the first readable state 727.

When the contents of package 350 reach a relative humidity in excess of 10%, such as 30%, the coloring element 764 changes color, such that the portion of the coloring element 764 which is readable through the transparent area 734 appears similarly to the machine-readable code in the first readable state 727.

The coloring agent on coloring element 746 begins to melt generally immediately and be released from coloring element 746 and begins to diffuse through relatively long-term coloring agent diffusion pathway defining element 748. When the elapsed time is greater than a first predetermined time, such as one week, the coloring agent progresses towards the end of the pathway defined by the relatively long-term coloring agent diffusion pathway defining element 748 and reaches relatively quick coloring agent diffusion region defining element 750, where it rapidly impregnates the portion of the element 750 which is readable through the transparent area 730 so that it appears similarly to the machine-readable code in the first readable state 727.

The colored transparent areas 730, 734 and 738 can be read together with the machine-readable code in the first readable state 727 as a single machine-readable code in second readable state 740 as designated by B in FIG. 5C.

When the contents of package 350 reach a temperature of more than 12 degrees Celsius, such as 20 degrees Celsius, the coloring agent on coloring element 790 begins to melt and be released from coloring element 790 and begins to diffuse through the opaque layer 792. When the temperature exceeds 12 degrees Celsius for at least a minimum time, such as five minutes, the coloring agent rapidly diffuses through the opaque layer 792, such that the portion of the opaque layer 792 which is readable through the transparent area 730 appears similarly to the machine-readable code in the first readable state 727.

When the contents of package 350 reach a relative humidity in excess of 40%, such as 60%, the coloring element 774 changes color, such that the portion of the coloring element 774 which is readable through the transparent area 736 appears similarly to the machine-readable code in the first readable state 727.

The coloring agent on coloring element 756 begins to melt generally immediately and be released from coloring element 756 and begins to diffuse through relatively long-term coloring agent diffusion pathway defining element 758. When the elapsed time is greater than a second predetermined time, such as two weeks, the coloring agent progresses towards the end of the pathway defined by the relatively long-term coloring agent diffusion pathway defining element 758 and reaches relatively quick coloring agent diffusion region defining element 760, where it rapidly impregnates the portion of the element 760 which is readable through the transparent area 732 so that it appears similarly to the machine-readable code in the first readable state 727.

The colored transparent areas 730, 732, 734, 736, 738 and 739 can be read together with the machine-readable code in the first readable state 727 as a single machine-readable code in third readable state 742 as designated by C in FIG. 5C.

It is appreciated that while the illustrated embodiments of FIGS. 5A-5C include transparent areas including multiple variable machine-readable cells, each of the transparent areas may include a single variable machine-readable cell or multiple variable machine-readable cells. Typically, transparent areas include multiple variable machine-readable cells to enhance readability.

Figure 6:
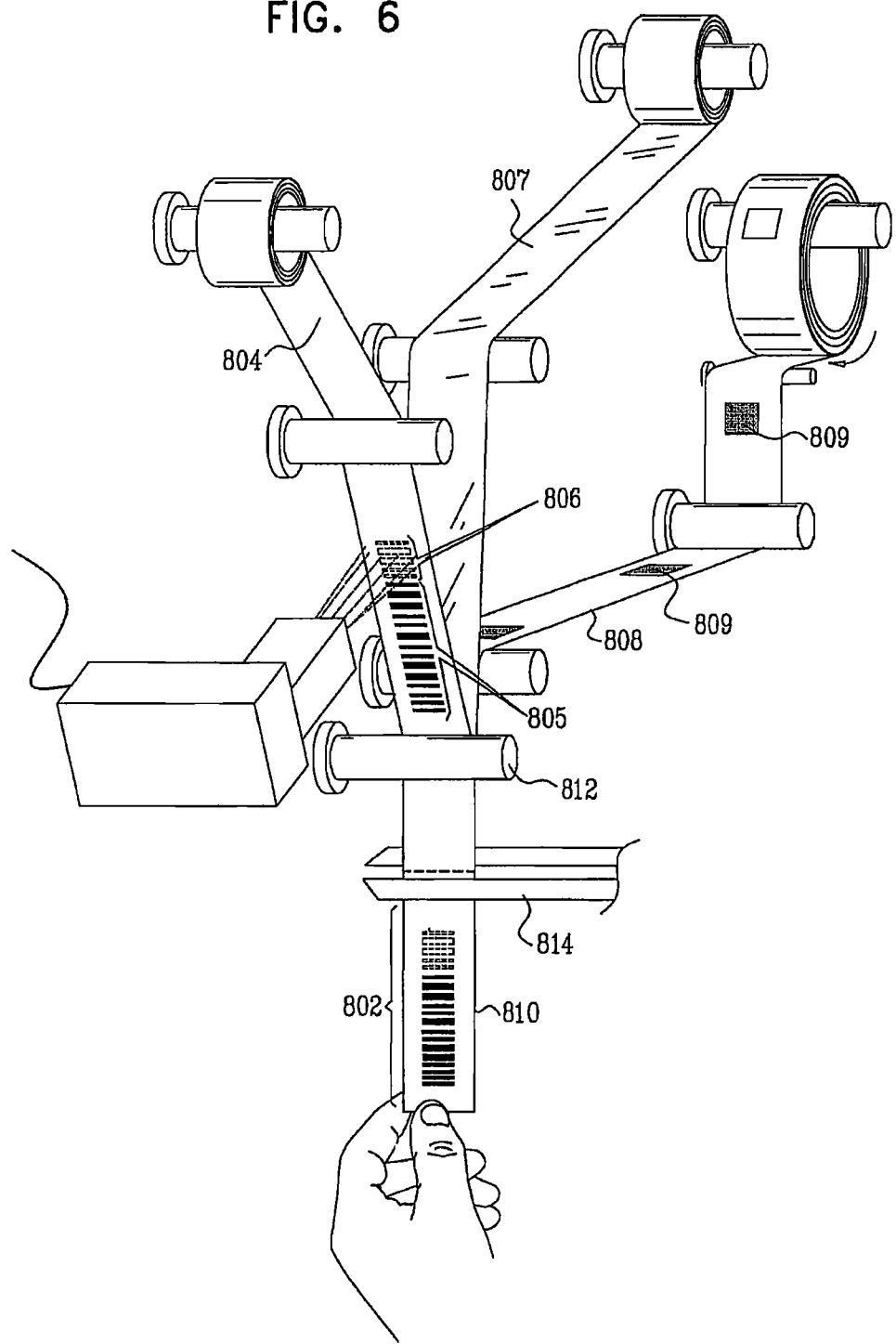
FIG. 6 is a simplified illustration of a method and apparatus for producing indicators constructed and operative in accordance with the present invention.

Reference is now made to FIG. 6, which illustrates a method and apparatus for producing indicators 802 constructed and operative in accordance with the present invention, such as the indicators described hereinabove with reference to FIG. 4A, preferably on a "just in time" basis. As seen in FIG. 6, three continuous substrate strips are provided: a strip 804 of a transparent material, such as plastic, on which appears a bar code in a first readable state 805 and alongside it a plurality of transparent areas 806, a strip 807 of an opaque material, corresponding to opaque layer 412 in the embodiment of FIG. 4A, and a strip 808 having formed thereon at predetermined locations therealong a plurality of ink impregnated regions 809, corresponding to temperature responsive color elements 410 in the embodiment of FIG. 4A. Strip 808 is preferably maintained under strict temperature conditions prior to use, so that the temperature thereat does not exceed 4 degrees Celsius.

Preferably strips 804 and 807 are joined to each other, as by an adhesive. This may be done at a roller or, alternatively, strips 804 and 807 may be supplied already joined together.

A series of bar code defining layers 810, each corresponding to bar code defining layer 402 in the embodiment of FIG. 4A, is formed on strip 804 by conventional printing techniques, preferably digital printing techniques. The printing preferably takes place "just in time" so as to ensure that each indicator 802 corresponds to a correct package. The printing on the transparent substrate preferably defines the bar code in a first readable state 805 and alongside it the plurality of transparent areas 806. It is appreciated that the remainder of the transparent substrate 804, other than the bar code in a first readable state 805 and the transparent areas 806, is preferably printed in a white color or a color defining high contrast with respect to the bar code in the first readable state 805.

Strips 804, 807 and 808 are laminated together in suitable registration as shown generally at roller 812 by any suitable technique, such as the use of heat or adhesive. Preferably a perforator 814 forms a perforation line between adjacent indicators 802 in order to enhance the ease of separating individual indicators.

It is appreciated that similar manufacturing techniques may be employed, as appropriate for other indicators.

Figure 7A:
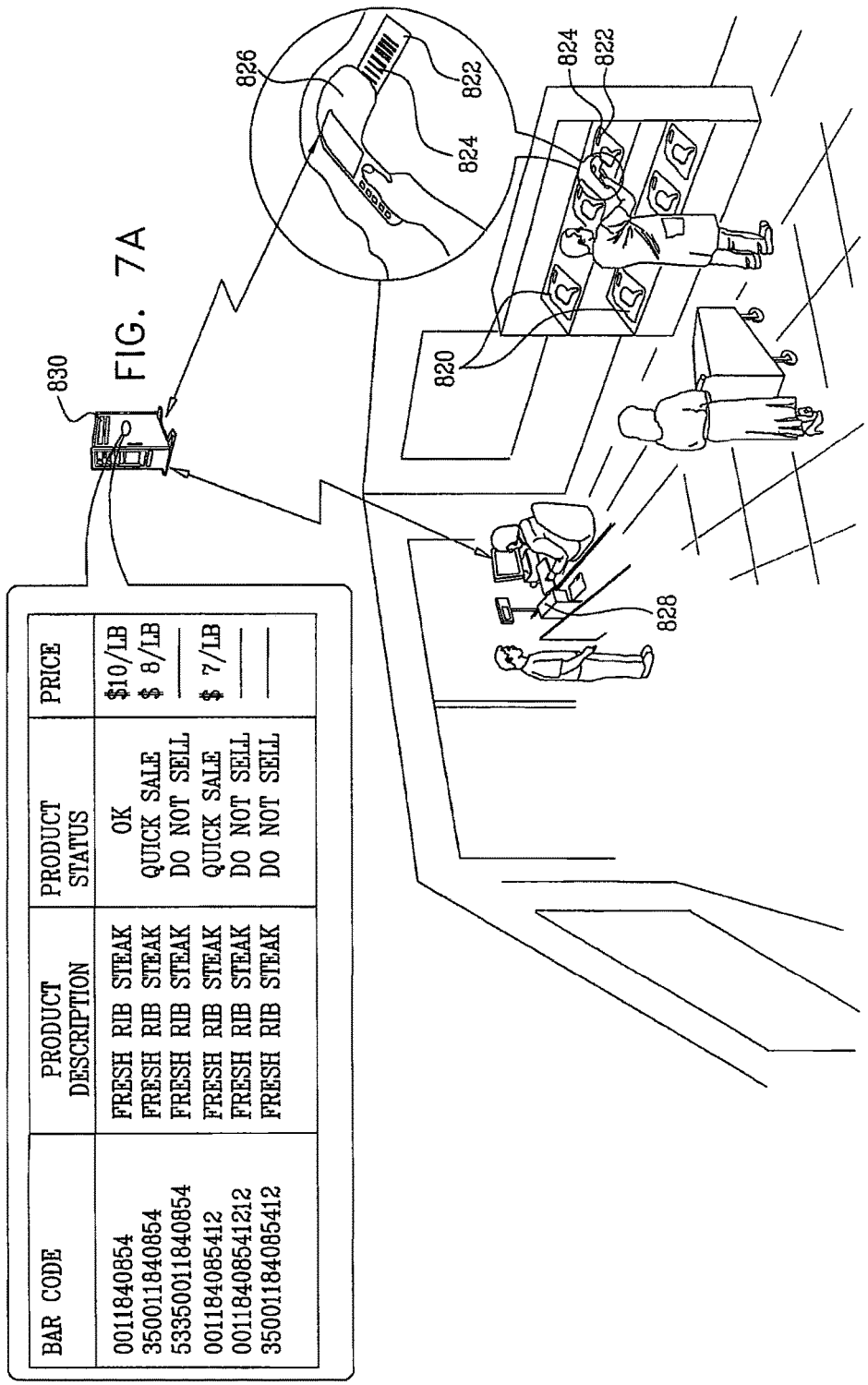
FIG. 7A is a simplified illustration of the structure and operation of a quality management system constructed and operative in accordance with a preferred embodiment of the present invention in the context of a supermarket.

Reference is now made to FIG. 7A, which illustrates the structure and operation of a quality management system constructed and operative in accordance with a preferred embodiment of the present invention in the context of a supermarket. In the embodiment of FIG. 7A, packaged products 820 each bear an event indicator 822 of the general type described hereinabove and illustrated in FIGS. 1-5C and including one or more of the operational and structural features described hereinabove.

In the illustrated embodiment, indicator 822 preferably presents a variable bar code 824 which includes a product designator. Such a bar code may, but need not necessarily, include a UPC code. When this code is read, as by a conventional bar code reader 826 used by a stock checker or by a conventional checkout scanner 828, it provides product identification information to a product management server 830.

As described hereinabove, the bar code 824 is preferably a variable bar code which, depending on the product, may provide bar code readable indications of one or more event parameters, such as temperature and elapsed time, and for each such parameter may indicate multiple levels. For example, where the packaged product 820 is fresh rib steak, as shown, the bar code 824 may have multiple readable states such as:

FIRST READABLE STATE 0011840854-FRESH RIB STEAK TEMPERATURE DID NOT EXCEED 4 DEGREES CELSIUS TIME DURATION FROM PACKAGING DID NOT EXCEED 3 DAYS

SECOND READABLE STATE 350011840854-FRESH RIB STEAK TEMPERATURE DID NOT EXCEED 4 DEGREES CELSIUS TIME DURATION FROM PACKAGING DID EXCEED 3 DAYS BUT DID NOT EXCEED 6 DAYS

THIRD READABLE STATE 53350011840854-FRESH RIB STEAK TEMPERATURE DID NOT EXCEED 4 DEGREES CELSIUS TIME DURATION FROM PACKAGING DID EXCEED 6 DAYS

FOURTH READABLE STATE 001184085412-FRESH RIB STEAK TEMPERATURE DID EXCEED 4 DEGREES CELSIUS BUT DID NOT EXCEED 15 DEGREES CELSIUS

FIFTH READABLE STATE 00118408541212-FRESH RIB STEAK TEMPERATURE DID EXCEED 15 DEGREES CELSIUS

SIXTH READABLE STATE 35001184085412-FRESH RIB STEAK TEMPERATURE DID EXCEED 4 DEGREES CELSIUS TIME DURATION FROM PACKAGING DID EXCEED 3 DAYS

In the illustrated embodiment, the product management server 830 maintains a database which preferably contains at least the following information:

| BAR CODE | PRODUCT DESCRIPTION | PRODUCT STATUS | PRICE |
|---|---|---|---|
| 0011840854 | FRESH RIB STEAK | OK | $10/LB |
| 350011840854 | FRESH RIB STEAK | QUICK SALE | $8/LB |
| 53350011840854 | FRESH RIB STEAK | DO NOT SELL | |
| 001184085412 | FRESH RIB STEAK | QUICK SALE | $7/LB |

-continued

| BAR CODE | PRODUCT DESCRIPTION | PRODUCT STATUS | PRICE |
|---|---|---|---|
| 00118408541212 | FRESH RIB STEAK | DO NOT SELL | |
| 35001184085412 | FRESH RIB STEAK | DO NOT SELL | |

Based on the scanned bar code, the product management server 830 provides both product status information and price information as appropriate to management as well as points of sale.

Reference is now made to FIG. 7B, which illustrates the structure and operation of a quality management system constructed and operative in accordance with another preferred embodiment of the present invention in the context of a supermarket. In the embodiment of FIG. 7B, packaged products 850 each bear an event indicator 852 of the general type described hereinabove and illustrated in FIGS. 1-5C and including one or more of the operational and structural features described hereinabove.

In the illustrated embodiment, indicator 852 preferably presents a variable bar code 854 which does not include a product designator. A separate bar code bearing indicator 855, including, for example, a UPC code, may appear on each packaged product 850 or alternatively, a product designation may be entered manually when scanning bar code 854.

When bar code 854 is read, as by a conventional bar code reader 856, used by a stock checker or by a conventional checkout scanner 858, it provides event information but it does not provide product identification information to a product management server 860. Product identification information may be entered by scanning bar code bearing indicator 855 or manually.

As described hereinabove, with reference to FIGS. 1-5C, the bar code 854 is preferably a variable bar code which, depending on the product, may provide bar code readable indications of one or more event parameters, such as temperature and elapsed time, and for each such parameter may indicate multiple levels. In the illustrated example, the packaged product 850, as shown in a Product Description Table, is fresh rib steak, and the variable bar code 854 may have multiple readable states corresponding to multiple events, such as shown below in an Event Description Table.

In the illustrated embodiment of FIG. 7B, the variable bar code 854 includes a first readable state 0123, a second readable state 350123, a third readable state 53350123, a fourth readable state 012312, a fifth readable state 01231212 and a sixth readable state 35012312.

As seen in the illustrated embodiment, the product management server 860 maintains a database which preferably includes at least a product description table, such as Table 1, and an event report table, such as Table 2.

TABLE 1

| PRODUCT DESCRIPTION BAR CODE (855) | PRODUCT DESCRIPTION |
|---|---|
| 0011840854 | FRESH RIB STEAK |

TABLE 2

| EVENT BAR CODE (854) | EVENT DESCRIPTION |
|---|---|
| 0123 | TEMPERATURE DID NOT EXCEED 4 DEGREES CELSIUS TIME DURATION FROM PACKAGING DID NOT EXCEED 3 DAYS |
| 350123 | TEMPERATURE DID NOT EXCEED 4 DEGREES CELSIUS TIME DURATION FROM PACKAGING DID EXCEED 3 DAYS BUT DID NOT EXCEED 6 DAYS |
| 53350123 | TEMPERATURE DID NOT EXCEED 4 DEGREES CELSIUS TIME DURATION FROM PACKAGING DID EXCEED 6 DAYS |
| 012312 | TEMPERATURE DID EXCEED 4 DEGREES CELSIUS BUT DID NOT EXCEED 15 DEGREES CELSIUS |
| 01231212 | TEMPERATURE DID EXCEED 15 DEGREES CELSIUS |
| 35012312 | TEMPERATURE DID EXCEED 4 DEGREES CELSIUS TIME DURATION FROM PACKAGING DID EXCEED 3 DAYS |

Upon receipt of inputs identifying a product in Table 1 and indicating an event description in Table 2 corresponding to the same product, the product management server 860 is operative to provide a product status table, such as Table 3, typically including a product description bar code (P.D.B.C.), an event bar code (E.B.C.), a product description, a product status and a price, as follows:

TABLE 3

| P.D.B.C. | E.B.C. | PRODUCT DESCRIPTION | PRODUCT STATUS | PRICE |
|---|---|---|---|---|
| 0011840854 | 0123 | FRESH RIB STEAK | OK | $10/LB |
| 0011840854 | 35013 | FRESH RIB STEAK | QUICK SALE | $8/LB |
| 0011840854 | 53350123 | FRESH RIB STEAK | DO NOT SELL | |
| 0011840854 | 012312 | FRESH RIB STEAK | QUICK SALE | $7/LB |
| 0011840854 | 01231212 | FRESH RIB STEAK | DO NOT SELL | |
| 0011840854 | 35012312 | FRESH RIB STEAK | DO NOT SELL | |

The product management server 860 provides both product status information and price information from Table 3 to management as well as to points of sale as appropriate.

It will be appreciated by persons skilled in the art that the present invention is not limited by what has been particularly shown and described hereinabove. Rather the scope of the present invention includes both combinations and subcombinations of various feature of the invention and modifications thereof which may occur to persons skilled in the art upon reading the foregoing description and which are not in the prior art.

The invention claimed is:

1. A product container operative to provide a machine-readable indication of exceedence of at least one threshold by at least one product quality determining parameter, said product container comprising:
   a machine-readable indicator located within said product container, said machine-readable indicator having a first machine-readable state, prior to exceedence of said at least one threshold, and at least one second machine-readable state, following exceedence of said at least one threshold, said machine-readable indicator including:
   a machine-readable code defining layer, defining a machine-readable indicator in said first readable state;
   a plurality of transparent areas, which, when colored, define, together with said machine-readable code defining layer, said at least one second machine-readable state;
   at least one coloring element;
   an opaque layer disposed intermediate said machine-readable code defining layer and said at least one coloring element; and
   at least one coloring agent located on said at least one coloring element, said at least one coloring agent operative to diffuse through said opaque layer following exceedance of said at least one threshold; and
   a transparent portion formed in said product container for viewing said machine-readable indicator.

2. A product container according to claim 1 and wherein said transparent portion is formed in a wall of said product container.

3. A product container according to claim 1 and wherein said machine-readable code defining layer is printed on a transparent substrate.

4. A quality management system for products comprising:
   a multiplicity of product containers each operative to provide a machine-readable indication of exceedence of at least one threshold by at least one product quality determining parameter, each of said product containers comprising:
   a machine-readable indicator located within said product container, said machine-readable indicator having a first machine-readable state, prior to exceedence of said at least one threshold, and at least one second machine-readable state, following exceedence of said at least one threshold, said machine-readable indicator including:
   a machine-readable code defining layer, defining a machine-readable indicator in said first readable state;
   a plurality of transparent areas, which, when colored, define, together with said machine-readable code defining layer, said at least one second machine-readable state;
   at least one coloring element;
   an opaque layer disposed intermediate said machine-readable code defining layer and said at least one coloring element; and
   at least one coloring agent located on said at least one coloring element, said at least one coloring agent operative to diffuse through said opaque layer following exceedance of said at least one threshold; and a transparent portion formed in said product container for viewing said machine-readable indicator;

an indicator reader operative to read said machine-readable indicators and to provide output indications; and a product type specific indication interpreter operative to receive said output indications and to provide human sensible, product specific, product quality status outputs.

5. A method for quality management for products comprising:

employing a multiplicity of product containers, each operative to provide a machine-readable indication of exceedence of at least one threshold by at least one product quality determining parameter, each of said product containers comprising:

a machine-readable indicator located within said product container, said machine-readable indicator having a first machine-readable state, prior to exceedence of said at least one threshold, and at least one second machine-readable state, following exceedence of said at least one threshold, said machine-readable indicator including:

a machine-readable code defining layer, defining a machine-readable indicator in said first readable state;

a plurality of transparent areas, which, when colored, define, together with said machine-readable code defining layer, said at least one second machine-readable state;

at least one coloring element;

an opaque layer disposed intermediate said machine-readable code defining layer and said at least one coloring element; and at least one coloring agent located on said at least one coloring element, said at least one coloring agent operative to diffuse through said opaque layer following exceedance of said at least one threshold; and a transparent portion formed in said product container for viewing said machine-readable indicator;

reading said machine-readable indicators and providing output indications therefrom; and interpreting said output indications to provide human sensible, product unit specific, product quality status outputs.

\* \* \* \* \*